US007223789B2

(12) United States Patent
Gopalan et al.

(10) Patent No.: US 7,223,789 B2
(45) Date of Patent: May 29, 2007

(54) HETEROCYCLIC COMPOUNDS USEFUL FOR THE TREATMENT OF INFLAMMATORY AND ALLERGIC DISORDERS: PROCESS FOR THEIR PREPARATION AND PHARMACEUTICAL COMPOSITIONS CONTAINING THEM

(75) Inventors: Balasubramanian Gopalan, Mumbai (IN); Laxmikant Atmaram Gharat, Thane (IN); Aftab Dawoodbhai Lakdawala, Mumbai (IN); Usha Karaunakaran, Mumbai (IN)

(73) Assignee: Glenmark Pharmaceuticals S.A., La Chaux-De-Fonds (CH)

( * ) Notice: Subject to any disclaimer, the term of this patent is extended or adjusted under 35 U.S.C. 154(b) by 114 days.

(21) Appl. No.: 10/821,642

(22) Filed: Apr. 9, 2004

(65) Prior Publication Data

US 2005/0027129 A1 Feb. 3, 2005

Related U.S. Application Data

(63) Continuation-in-part of application No. PCT/IB04/00355, filed on Feb. 11, 2004.

(60) Provisional application No. 60/519,967, filed on Nov. 13, 2003.

(30) Foreign Application Priority Data

Apr. 11, 2003 (IN) .................... 363/MUM/2003

(51) Int. Cl.
  *A61K 31/38* (2006.01)
  *A61K 31/352* (2006.01)
  *C07D 307/91* (2006.01)
  *C07D 333/76* (2006.01)
  *C07D 405/12* (2006.01)
  *C07D 409/12* (2006.01)

(52) U.S. Cl. .................. 514/437; 514/455; 549/48; 549/461; 546/284.7; 546/281.1; 544/375; 544/153

(58) Field of Classification Search ............ 549/461, 549/43, 48; 548/444; 546/284.7, 281.1; 544/375, 153; 514/437, 455
See application file for complete search history.

(56) References Cited

U.S. PATENT DOCUMENTS

| | | | |
|---|---|---|---|
| 3,759,948 A | 9/1973 | Shen et al. | |
| 3,846,553 A | 11/1974 | Shen et al. | |
| 4,222,944 A | 9/1980 | Berger et al. | |
| 5,814,651 A | 9/1998 | Duplantier et al. | |
| 6,110,962 A | 8/2000 | Wrobel et al. | |

FOREIGN PATENT DOCUMENTS

| | | |
|---|---|---|
| EP | 62158253 | 7/1987 |
| EP | 0 497 564 A1 | 8/1992 |
| EP | 1 270 577 A1 | 1/2003 |
| GB | 1041861 | 2/1963 |
| GB | 1285398 | 8/1972 |
| JP | 63 014156 | 6/1988 |
| WO | WO 92/10476 A1 | 6/1992 |
| WO | WO 93/19747 A1 | 10/1993 |
| WO | WO 94/02465 A1 | 2/1994 |
| WO | WO 94/08995 A1 | 4/1994 |
| WO | WO 94/20446 A1 | 9/1994 |
| WO | WO 95/01338 A1 | 1/1995 |
| WO | WO 95/04046 A1 | 2/1995 |
| WO | WO 95/09837 A1 | 4/1995 |
| WO | WO 95/20578 A1 | 8/1995 |
| WO | WO 95/24381 A1 | 9/1995 |
| WO | WO 96/03377 | 2/1996 |
| WO | WO 98/09934 A1 | 3/1998 |
| WO | WO 99/47545 A2 | 9/1999 |
| WO | WO 99/58521 | 11/1999 |
| WO | WO 01/27107 A2 | 4/2001 |
| WO | WO 01/70673 A2 | 9/2001 |
| WO | WO 01/70746 A1 | 9/2001 |
| WO | WO 02/060867 A2 | 8/2002 |
| WO | WO 02/072567 A2 | 9/2002 |
| WO | WO 2004/016596 A1 | 2/2004 |
| WO | WO 2004/022536 A1 | 3/2004 |
| WO | WO 2004/037805 | 5/2004 |
| WO | WO 2004/037805 A1 | 5/2004 |

OTHER PUBLICATIONS

Koyama et al., Heterocycles 1981; 16(6):969-972.
Hulme et al., Bioorganic and Medicinal Chemistry Letters 1998; 8:175-178.
Silvestre et al., Drugs of the Future 1998; 23(6):607-615.
Fox et al., J. Med. Chem. 2002; 45(2):360-370.
U.S. Appl. No. 10/532,273, Balasubramanian et al.
Nielson, K.F. et al, Fungal metabolite screening: database of 474 mycotoxins and fungal metabolites for dereplication by standardised liquid chromatography-UV-mass spectrometry methodology. *Journal of Chromatography* 1002, 1-2:111-136.

*Primary Examiner*—Kamal A. Saeed
*Assistant Examiner*—Yong Chu
(74) *Attorney, Agent, or Firm*—Darby & Darby

(57) ABSTRACT

The present invention relates to novel heterocyclic compounds, their analogs, their tautomers, their regioisomers, their stereoisomers, their enantiomers, their diastereomers, their polymorphs, their pharmaceutically acceptable salts, their appropriate N-oxides, their pharmaceutically acceptable solvates and their pharmaceutical compositions containing them. The present invention more particularly relates to novel Phosphodiesterase type 4 (PDE4) inhibitors of the Formula (1), their analogs, tautomers, enantiomers, diastereomers, regioisomers, stereoisomers, polymorphs, pharmaceutically acceptable salts, appropriate N-oxide, pharmaceutically acceptable solvates and the pharmaceutical compositions containing them.

77 Claims, No Drawings

HETEROCYCLIC COMPOUNDS USEFUL FOR THE TREATMENT OF INFLAMMATORY AND ALLERGIC DISORDERS: PROCESS FOR THEIR PREPARATION AND PHARMACEUTICAL COMPOSITIONS CONTAINING THEM

FIELD OF THE INVENTION

This application claims the benefit of Indian Provisional Patent Application 363/MUM/2003, filed Apr. 11, 2003 and U.S. Provisional Patent Application 60/519,967, filed Nov. 13, 2003, and is a continuation-in-part of International Application No. PCT/IB2004/000355, filed Feb. 11, 2004. All of these priority applications are incorporated herein by reference in their entireties.

The present invention relates to novel heterocyclic compounds, their analogs, their tautomers, their regioisomers, their stereoisomers, their enantiomers, their diastereomers, their polymorphs, their pharmaceutically acceptable salts, their appropriate N-oxides, their pharmaceutically acceptable solvates and their pharmaceutical compositions containing them. The present invention more particularly relates to novel Phosphodiesterase type 4 (PDE4) inhibitors of the Formula (1), their analogs, their tautomers, their enantiomers, their diasteromers, their regioisomers, their stereoisomers, their polymorphs, their pharmaceutically acceptable salts, their appropriate N-oxide, their pharmaceutically acceptable solvates and the pharmaceutical compositions containing them.

The invention thus relates to compounds of the Formula (1)

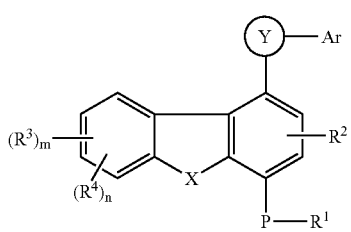

wherein:

$R^1$, $R^2$ and $R^3$ may be same or different and are independently selected for each occurrence from the groups consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, nitro, —OH, cyano, formyl, acetyl, halogen, protecting groups, —C(O)—$R^a$, —C(O)O—$R^a$, —C(O)N$R^aR^a$, —S(O)$_q$—$R^a$, —S(O)$_q$—N$R^aR^a$, —N$R^aR^a$, , —O$R^a$, —S$R^a$ or when two $R^3$ substitutents ortho to each other, may be joined to a form a saturated or unsaturated cyclic 3–7 membered ring, which may optionally include up to two heteroatoms which may be same or different selected from O, N$R^a$ or S;

wherein $R^4$ is —N$R^5R^6$; wherein $R^5$ and $R^6$ may be same or different and are independently selected from the groups consisting of hydrogen, substituted or unsubstituted alkyl, substituted or unsubstituted alkenyl, substituted or unsubstituted alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, nitro, —OH, cyano, halogen, —C(O)—$R^a$, —C(O)O—$R^a$, —C(O)N$R^aR^a$, —S(O)$_q$—$R^a$, —S(O)$_q$—N$R^aR^a$, —C(=N$R^a$)—$R^a$, —C(=N$R^a$)—N$R^aR^a$, —C(=S)—N$R^aR^a$, —C(=S)—$R^a$, N=C($R^aR^a$), —N$R^aR^a$, —O$R^a$, —S$R^a$, protecting groups or $R^5$ and $R^6$ to each other may be joined to a form a saturated or unsaturated 3–7 membered cyclic ring, which may optionally include up to two heteroatoms which may be same or different selected from O, N$R^a$ or S;

Ar is selected from the group consisting of substituted or unsubstituted aryl, substituted or unsubstituted arylalkyl, substituted or unsubstituted heterocyclic ring and substituted or unsubstituted heteroaryl ring;

Preferably Ar is optionally substituted phenyl, optionally substituted benzyl, optionally substituted pyrimidine, optionally substituted pyridyl selected from 4-pyridyl, 3-pyridyl and 2-pyridyl or optionally substituted pyridyl-N-oxide selected from 4-pyridyl-N-oxide, 3-pyridyl-N-oxide and 2-pyridyl-N-oxide in which optional substituents (one or more) may be same or different and are independently selected from the groups consisting of hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino X is selected from the group consisting of O, S(O)$_q$ and N$R^a$;

Y is selected from the group consisting of —C(O)N$R^7$, —N$R^7$S(O)$_q$, —S(O)$_q$N$R^7$ and —N$R^7$C(O);

$R^7$ is selected from the group consisting of hydrogen, substituted or unsubstituted alkyl, hydroxyl, —O$R^a$, substituted or unsubstituted aryl, and substituted or unsubstituted heterocyclic ring;

wherein P is chosen from the group consisting of O and S;

wherein m represents 0–3;

wherein n represents 1–4;

wherein q represents 0, 1 or 2;

with the proviso that $R^4$ is not $NH_2$ wherein $R^a$ is selected from the group consisting of hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, nitro, —OH, cyano, formyl, acetyl, halogen, protecting groups, —(O)—$R^a$, —C(O)O—$R^a$, —C(O)N$R^aR^a$, —S(O)$_q$—$R^a$, —S(O)$_q$—N$R^aR^a$, —N$R^aR^a$, —O$R^a$ and —S$R^a$;

and their analogs, their tautomers, their regioisomers, their stereoisomers, their enantiomers, their diastereomers, their polymorphs, their pharmaceutically acceptable salts, their N-oxides, their pharmaceutically acceptable solvates and their pharmaceutical compositions containing them or a pharmaceutical acceptable salts thereof.

The present invention also relates to a process for the preparation of the above said novel heterocyclic compounds of Formula 1 as defined above.

The compounds of general Formula (1) more particularly, down regulate or inhibit the production of TNF-α as they are PDE4 inhibitors and therefore are useful in the treatment of variety of allergic and inflammatory diseases including asthma, chronic bronchitis, atopic dermatitis, urticaria, allergic rhinitis, allergic conjunctivitis, vernal conjuctivitis, eosinophilic granuloma, psoriasis, rheumatoid arthritis, septic shock, ulcerative colitis, Crohn's disease, reperfusion injury of the myocardium and reperfusion injury of the brain, chronic glomerulonephritis, endotoxic shock and adult respiratory distress syndrome. The compounds of the present invention are particularly useful for the treatment of asthma or chronic obstructive pulmonary disease (COPD).

BACKGROUND OF THE INVENTION

Airway inflammation characterizes a number of severe lung diseases including asthma and chronic obstructive pulmonary disease (COPD). Events leading to airway obstruction include edema of airway walls, infiltration of inflammatory cells into the lung, production of various inflammatory mediators and increased mucous production. The airways of asthmatic patients are infiltrated by inflammatory leukocytes, of which the eosinophil is the most prominent component. The magnitude of asthmatic reactions is correlated with the number of eosinophils present in lungs.

The accumulation of eosinophils is found dramatically in the lungs of asthmatic patients although there are very few in the lungs of a normal individual. They are capable of lysing and activating cells and destroying tissues. When activated, they synthesize and release inflammatory cytokines such as IL-1, IL-3, TNF-α and inflammatory mediators such as PAF, LTD4 and related oxygen species that can produce edema and broncho-constriction. Tumor necrosis factor (TNF-α) was also known to be involved in the pathogenesis of a number of autoimmune and inflammatory diseases. Consequently, manipulation of the cytokine signaling or biosynthetic pathways associated with these proteins may provide therapeutic benefit in those disease states. It has been well demonstrated that TNF-α production in pro-inflammatory cells becomes attenuated by an elevation of intracellular cyclic adenosine 3',5'-monophosphate (cAMP). This second messenger is regulated by the phosphodiesterase (PDE) family of enzymes. The phosphodiesterase enzymes play an integral role in cell signaling mechanisms by hydrolyzing cAMP and cGP to their inactive 5' forms. Inhibition of PDE enzymes thus results in an elevation of cAMP and/or cGP levels and alters intracellular responses to extra cellular signals by affecting the processes mediated by cyclic nucleotides. Since eosinophilis are believed to be a critical proinflammatory target for asthma, identification of the expression of the PDE 4 gene family in eosinophils led to PDE 4 as potential therapeutic target for asthma [Rogers, D. F., Giembycz, M. A., *Trends Pharmacol. Sci.*, 19, 160–164(1998); Barnes, P. J., *Trends Pharmacol. Sci.*, 19, 415–423 (1998) herein incorporated by reference in their entirety].

The mammalian cyclic nucleotide phosphodiesterases (PDEs) are classified into ten families on the basis of their amino acid sequences and/or DNA sequence, substrate specificity and sensitivity to pharmacological agents [Soderling, S. H., Bayuga, S. J., and Beavo, J. A., *Proc. Natl. Acad. Sci., USA,* 96,7071–7076 (1999); Fujishige, K, Kotera, J., Michibata, H., Yuasa, K., Takebayashi, Si, Okamura, K. and Omori, K., *J. Biol. Chem.*, 274, 18438–18445 (1999) herein incorporated by reference in their entirety]. Many cell types express more than one PDE and distribution of isoenzymes between the cells varies markedly. Therefore development of highly isoenzyme selective PDE inhibitors provides a unique opportunity for selective manipulation of various pathophysiological processes.

Phosphodiesterase type 4 (PDE4) is an enzyme which regulates activities in cells which lead to inflammation in the lungs. PDE4, a cAMP-specific and $Ca^{+2}$-independent enzyme, is a key isozyme in the hydrolysis of cAMP in mast cells, basophils, eosinophils, monocytes and lymphocytes. The association between cAMP elevation in inflammatory cells with airway smooth muscle relaxation and inhibition of mediator release has led to widespread interest in the design of PDE4 inhibitors [Trophy,T. J., *Am. J. Respir. Crit. Care Med.*, 157, 351–370 (1998) herein incorporated by reference in their entirety]. Excessive or unregulated TNF-α production has been implicated in mediating or exacerbating a number of undesirable physiological conditions such as diseases including osteoarthritis, and other arthritic conditions; septic shock, endotoxic shock, respiratory distress syndrome and bone resorption diseases since TNF-α also participates in the onset and progress of autoimmune diseases, PDE4 inhibitors may find utility as therapeutic agents for rheumatoid arthritis, multiple sclerosis and Crohn's disease. [*Nature Medicine*, 1, 211–214 (1995) and *ibid.*, 244–248 herein incorporated by reference in their entirety].

Strong interest in drugs capable of selective inhibition of PDE 4 is due to several factors. Tissue distribution of PDE-4 suggests that pathologies related to the central nervous and immune systems could be treated with selective PDE-4 inhibitors. In addition, the increase in intracellular cAMP concentration, the obvious biochemical consequence of PDE-4 inhibition, has been well characterized in immunocompetent cells where it acts as a deactivating signal.

Recently the PDE4 family has grown to include four subtypes—PDE4A to PDE4D, each encoded by a distinct gene (*British Journal of Pharmacology;* 1999; v. 128; p. 1393–1398), herein incorporated by reference in its entirety.

It has been demonstrated that increasing cAMP levels within these cells results in suppression of cell activation, which in turn inhibits the production and release of pro-inflammatory cytokines such as TNF-α. Since eosinophilis are believed to be a critical pro-inflammatory target for asthma, identification of the expression of the PDE-4 gene family in eosinophils led to the PDE-4 as a potential therapeutic target for asthma.

The usefulness of several PDE-4 inhibitors, unfortunately, is limited due to their undesirable side effect profile which include nausea and emesis (due to action on PDE-4 in the central nervous system) and gastric acid secretion due to action on PDE-4 in parietal cells in the gut. Barnette, M. S., Grous, M., Cieslinsky, L. B., Burman, M., Christensen, S. B., Trophy, T J., *J. Pharmacol. Exp. Ther.*, 273,1396–1402 (1995) herein incorporated by reference in their entirety. One of the earliest PDE-4 inhibitors, Rolipram™, was withdrawn from clinical development because of its severe unacceptable side effect profile. Zeller E. et. al., *Pharmacopsychiatr,* 17, 188–190 (1984) herein incorporated by reference in its entirety. The cause of severe side effects of several PDE-4 inhibitor molecules in human clinical trials has recently become apparent.

There exist two binding sites on mammalian PDE-4 at which inhibitor molecules may bind. Also PDE-4 exists in two distinct forms which represent different conformations. They are designated as High affinity Rolipram binding site PDE-4H and Low affinity Rolipram binding site PDE-4L [Jacobitz, S., McLaughlin, M. M., Livi, G. P., Burman, M., Trophy, T. J., *Mol. Pharmaco,* 50, 891–899 (1996) herein incorporated by reference in their entirety]. It was shown that certain side effects (vomiting and gastric acid secretion) are associated with inhibition of PDE-4H whereas some beneficial actions are associated with PDE-4L inhibition. It was also found that human recombinant PDE-4 exists in 4 isoforms A, B, C and D [Muller, T., Engels, P., Fozard, J. R., *Trends Pharmacol. Sci.,* 17, 294–298 (1996) herein incorporated by reference in its entirety]. Accordingly, compounds displaying more PDE-4D isoenzyme selectivity over the A, B or C are found to have fewer side effects than Rolipram [Hughes. B et.al., *Br. J. Pharmacol.* 1996, 118) 1183–1191 herein incorporated by reference in their entirety]. Therefore, selective inhibitors of PDE-4 isozymes would have therapeutic effects in inflammatory diseases such as asthma and other respiratory diseases.

Although several research groups all over the world are working to find highly selective PDE-4 isozyme inhibitors, so far success has been limited. Various compounds have shown PDE-4 inhibition.

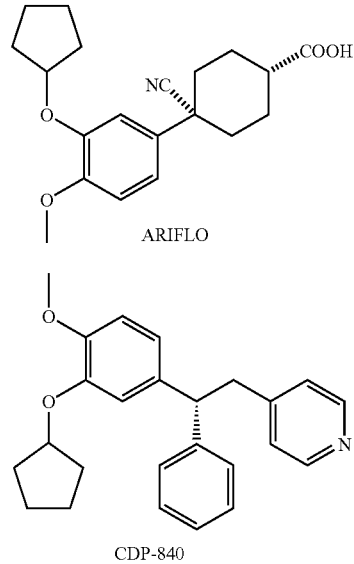

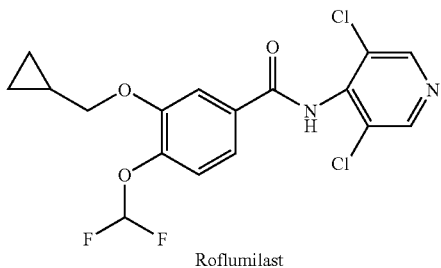

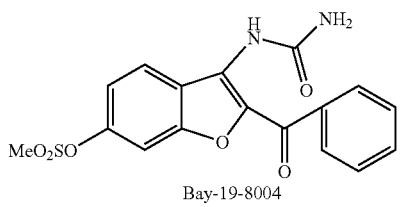

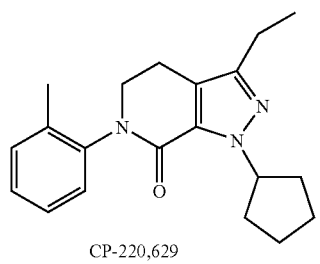

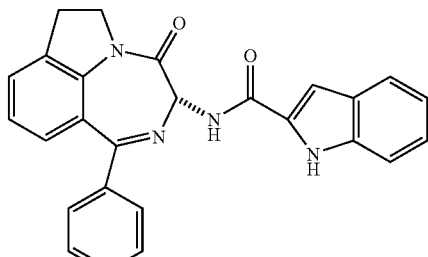

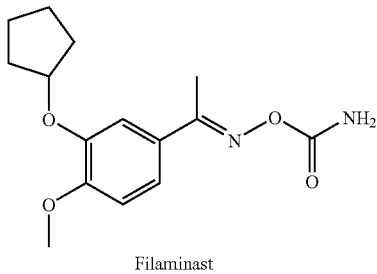

SmithKline Beecham's "Ariflo" which has the Formula A, Byk Gulden's Roflumilast which has the Formula D and Bayer's Bay-19-8004 which has the Formula E have reached advanced stage of human clinical trials. Other compounds which have shown potent PDE-4 inhibitory activity include Celltech's CDP-840 of the Formula B, Schering Plough's D-4418 of the Formula C, Pfizer's 5CP-220,629 which has the Formula F, Parke Davis's PD-168787 which has the Formula G and Wyeth's Filaminast which has the Formula H. However, recently due to efficacy and side effects problems, Ariflo, CDP-840 and Bay-19-8004 were discontinued from clinical trials as a treatment for asthma. Other compounds of the Formulae C and F are presently undergoing phase-1 clinical trials.

During the course of our research aimed at the development of novel anti-asthmatic compounds having potential PDE4 inhibitory activity, we have filed a WTO patent application in India bearing No. 922/MUM/2002 dated Oct. 23, 2002 and PCT application No. PCT/IB03/04442 dated Oct. 8, 2003 herein incorporated by reference in their entirety for a novel series of tricyclic compounds useful for the treatment of inflammatory and allergic disorders

SUMMARY OF THE INVENTION

Accordingly, the present invention provides novel heterocyclic compounds of the general Formula

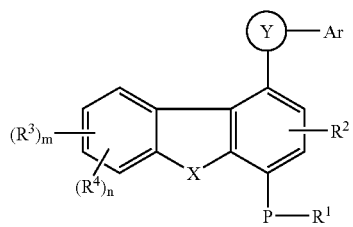

(1)

wherein:

$R^1$, $R^2$ and $R^3$ may be same or different and are independently selected for each occurrence from the groups consisting of hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, substituted or unsubstituted heteroarylalkyl, nitro, —OH, cyano, formyl, acetyl, halogen, protecting groups, —C(O)—$R^a$, —C(O)O—$R^a$, —C(O)NR$^a$R$^a$, —S(O)$_q$—R$^a$, —S(O)$_q$—NR$^a$R$^a$, —NR$^a$R$^a$, , —OR$^a$, —SR$^a$ or when two $R^3$ substitutents ortho to each other, may be joined to a form a saturated or unsaturated 3–7 membered cyclic ring which may optionally include up to two heteroatoms which may be same or different selected from O, NR$^a$ or S;

wherein $R^4$ is —NR$^5$R$^6$; wherein $R^5$ and $R^6$ may be same or different and are independently selected from the groups consisting of hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, nitro, —OH, cyano, halogen, —C(O)—R$^a$, —C(O)O—R$^a$, —C(O)NR$^a$R$^a$, —S(O)$_q$—R$^a$, —S(O)$_q$—NR$^a$R$^a$, —C(=NR$^a$)—R$^a$, —C(=NR$^a$)—NR$^a$R$^a$, —C(=S)—NR$^a$R$^a$, C(=S)—R$^a$, —N=C(R$^a$R$^a$), —NR$^a$R$^a$, —OR$^a$, —SR$^a$, protecting groups or R$^5$ and R$^6$ to each other may be joined to a form a saturated or unsaturated 3–7 membered cyclic ring, which may optionally include up to two heteroatoms which may be same or different selected from O, NR$^a$ or S;

Ar is selected from the group consisting of substituted or unsubstituted aryl, substituted or unsubstituted arylalkyl, substituted or unsubstituted heterocyclic ring and substituted or unsubstituted heteroaryl ring;

Preferably Ar is optionally substituted phenyl, optionally substituted benzyl, optionally substituted pyrimidine, optionally substituted pyridyl selected from 4-pyridyl, 3-pyridyl and 2-pyridyl or optionally substituted pyridyl-N-oxide selected from 4-pyridyl-N-oxide, 3-pyridyl-N-oxide and 2-pyridyl-N-oxide in which optional substituents (one or more) may be same or different and are independently selected from the groups consisting of hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino X is selected from the group consisting of O, S(O)$_q$ and NR$^a$;

Y is selected from the group consisting of —C(O)NR$^7$, —NR$^7$S(O)$_q$, —S(O)$_q$NR$^7$ and —NR$^7$C(O);

$R^7$ is selected from the group consisting of hydrogen, substituted or unsubstituted alkyl, hydroxyl, —OR$^a$, substituted or unsubstituted aryl, and substituted or unsubstituted heterocyclic ring;

wherein P is chosen from O and S;

wherein m represents 0–3;

wherein n represents 1–4;

wherein q represents 0, 1 or 2;

with the proviso that $R^4$ is not NH$_2$;

wherein R$^a$ is selected from the group consisting of hydrogen, substituted or unsubstituted alkyl, substituted or unsubstituted alkenyl, substituted or unsubstitued alkynyl, substituted or unsubstituted cycloalkyl, substituted or unsubstituted cycloalkylakyl, substituted or unsubstituted cycloalkenyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, substituted or unsubstituted heteroarylalkyl, nitro, —OH, cyano, formyl, acetyl, halogen, protecting groups, —C(O)—R$^a$, —C(O)O—R$^a$, —C(O)NR$^a$R$^a$, —S(O)$_q$—R$^a$, —S(O)$_q$—NR$^a$R$^a$, N$^a$R$^a$, —OR$^a$ or —SR$^a$;

and their analogs, their tautomers, their regioisomers, their stereoisomers, their enantiomers, their diastereomers, their polymorphs, their pharmaceutically acceptable salts, their N-oxides, their pharmaceutically acceptable solvates and their pharmaceutical compositions containing them or a pharmaceutical acceptable salts thereof.

The present invention also relates to a process for the preparation of the above said novel heterocyclic compounds of the Formula (1) as defined above. The compounds of general Formula (1) more particularly, down regulate or inhibit the production of TNF-α as they are PDE4 inhibitors and therefore are useful in the treatment of variety of allergic and inflammatory diseases including asthma, chronic bronchitis, atopic dermatitis, urticaria, allergic rhinitis, allergic conjunctivitis, vernal conjuctivitis, eosinophilic granuloma, psoriasis, rheumatoid arthritis, septic shock, diabetes, ulcerative colitis, Crohn's disease, reperfusion injury of the myocardium and brain, chronic glomerulonephritis, endotoxic shock and adult respiratory distress syndrome. The compounds of the present invention are particularly useful for the treatment of asthma and chronic obstructive pulmonary disease (COPD).

Further prefered are when the substituents in the 'substituted alkyl', 'substituted alkoxy' 'substituted alkenyl' 'substituted alkynyl' 'substituted cycloalkyl' 'substituted cycloalkylalkyl' 'substituted cycloalkenyl' 'substituted arylalkyl' 'substituted aryl' 'substituted heterocyclic ring', 'substituted heteroaryl ring,' 'substituted heteroarylalkyl', 'substituted heterocyclylalkyl ring', 'substituted amino', 'substituted alkoxycarbonyl', 'substituted cyclic ring' 'substituted alkylcarbonyl', 'substituted alkylcarbonyloxy' and may be the same or different which one or more are selected from the groups such as hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted heteroaryl, 'substituted heterocyclylalkyl ring' substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$ —NR$^x$C(S)NR$^y$R$^z$, —SONR$^x$R$^y$—, —SO$_2$NR$^x$R$^y$, —OR$^x$, —OR$^x$C(O)NR$^x$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, —ONO$_2$, wherein R$^x$, R$^y$ and R$^z$ in each of the above groups can be hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted heteroaryl, 'substituted heterocyclylalkyl ring' substituted or unsubstituted heteroarylalkyl, substituted or unsubstituted heterocyclic ring, Further prefered is where R$^1$ is unsubstituted alkyl.

Further prefered is where R$^1$ is methyl.
Further prefered is where R$^1$ is substituted alkyl.
Further prefered is where R$^1$ is —CHF$_2$.
Further prefered is where P is 0.
Further prefered is where X is O, N—CH$_3$, S.
Further prefered is where Y is —C(O)NH.
Further prefered is where Ar is selected from the group consisting of substituted or unsubstituted 4-pyridyl; substituted or unsubstituted 4-pyridyl-N-oxide; substituted or unsubstituted 3-pyridyl.
Further prefered is where said Ar substituent is halogen.
Further prefered is where said Ar substituent is chloro.
Further prefered is where Ar is selected from the group consisting of

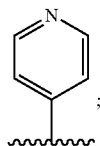 ; 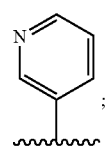 ; 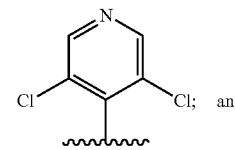 ; and

-continued

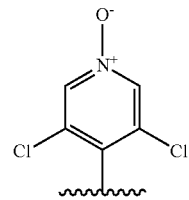

Further prefered is where Ar is

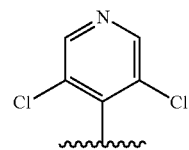

Further prefered is when m=0, n=1 and R$^4$ is selected from the group consisting of

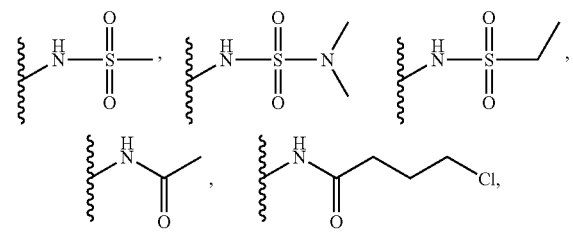

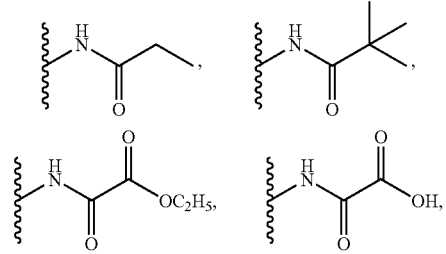

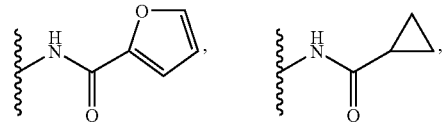

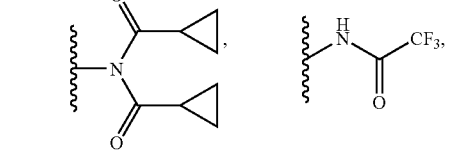

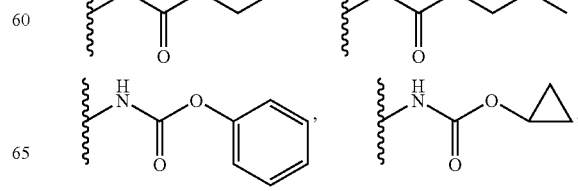

-continued

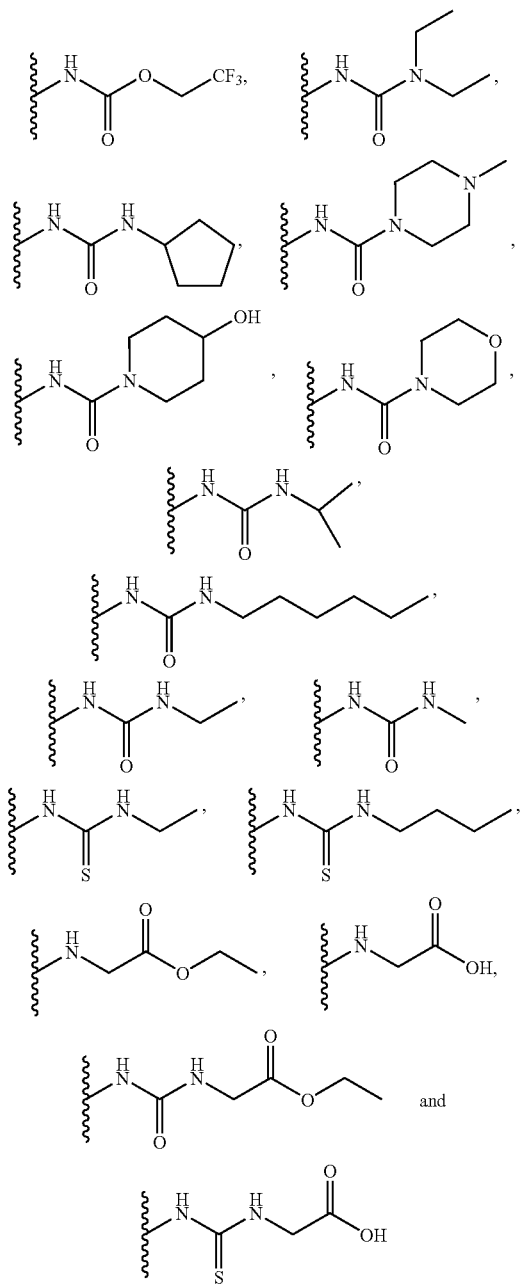

Further prefered is when m=0, n=1 and where $R^4$ is selected from the group consisting of

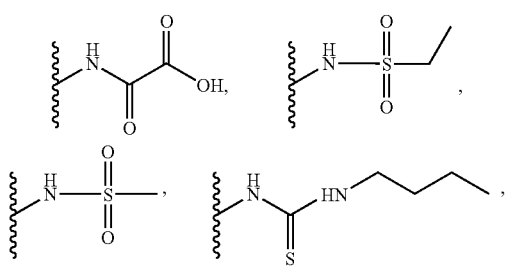

-continued

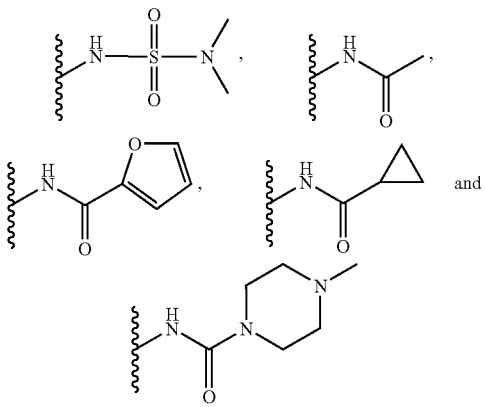

The present invention specifically excludes the following compound:

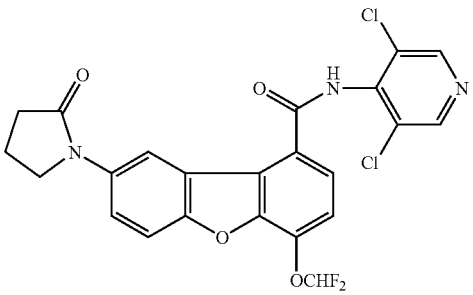

DETAILED DESCRIPTION OF THE INVENTION

The term 'alkyl' refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like.

The term "alkenyl" refers to aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, 2-butenyl and the like.

The term "alkynyl" refers to straight or branched chain hydrocarbyl radicals having at least one carbon-carbon triple bond, and having in the range of about 2 up to 12 carbon atoms (with radicals having in the range of about 2 up to 10 carbon atoms presently being preferred) e.g., ethynyl, propynyl, butnyl and the like.

The term "alkoxy" denotes alkyl group as defined above attached via oxygen linkage to the rest of the molecule. Representative examples of those groups are —$OCH_3$, —$OC_2H_5$ and the like.

The term "alkylcarbonyl" denotes alkyl group as defined above attached via carbonyl linkage to the rest of the molecule. Representative examples of those groups are —$C(O)CH_3$, —$C(O)C_2H_5$ and the like.

The term "alkoxycarbonyl" denotes alkoxy group as defined above attached via carbonyl linkage to the rest of the molecule. Representative examples of those groups are —C(O)—OCH$_3$, —C(O)—OC$_2$H$_5$ and the like.

The term "alkylcarbonyloxy" denotes alkylcarbonyl group as defined above attached via oxygen linkage to the rest of the molecule. Representative examples of those groups are —O—C(O)CH$_3$, —O—C(O)C$_2$H$_5$ and the like.

The term "alkylamino" denotes alkyl group as defined above attached via amino linkage to the rest of the molecule. Representative examples of those groups are —NH$_2$CH$_3$, —NH(CH$_3$)$_2$, —N(CH$_3$)$_3$ and the like.

The term "cycloalkyl" denotes a non-aromatic mono or multicyclic ring system of about 3 to 12 carbon atoms such as cyclopropyl, cyclobutyl, cyclopentyl, cyclohexyl and examples of multicyclic cycloalkyl groups include perhydronapththyl, adamantyl and norbornyl groups bridged cyclic group or sprirobicyclic groups e.g sprio (4,4) non-2-yl.

The term "cycloalkylalkyl" refers to cyclic ring-containing radicals containing in the range of about 3 up to 8 carbon atoms directly attached to alkyl group which are then attached to the main structure at any carbon from alkyl group that results in the creation of a stable structure such as cyclopropylmethyl, cyclobutylethyl, cyclopentylethyl, and the like.

The term "cycloalkenyl" refers to cyclic ring-containing radicals containing in the range of about 3 up to 8 carbon atoms with at least one carbon-carbon double bond such as cyclopropenyl, cyclobutenyl, cyclopentenyl and the like.

The term "aryl" refers to aromatic radicals having in the range of 6 up to 14 carbon atoms such as phenyl, naphthyl, tetrahydronapthyl, indanyl, biphenyl and the like.

The term "arylalkyl" refers to an aryl group as defined above directly bonded to an alkyl group as defined above. e.g., —CH$_2$C$_6$H$_5$, —C$_2$H$_5$C$_6$H$_5$ and the like.

The term "heterocyclic ring" refers to a stable 3- to 15 membered ring radical which consists of carbon atoms and from one to five heteroatoms selected from the group consisting of nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide thiamorpholinyl sulfone, dioxaphospholanyl, oxadiazolyl, chromanyl, isochromanyl and the like. The above includes substituted or unsubstituted pyridyl N-oxides.

The term "heteroaryl" refers to heterocyclic ring radical as defined above. The heteroaryl ring radical may be attached to the main structure at any heteroatom or carbon atom that results in the creation of a stable structure.

The heterocyclic ring radical may be attached to the main structure at any heteroatom or carbon atom that results in the creation of a stable structure.

The term "heteroarylalkyl" refers to heteroaryl ring radical as defined above directly bonded to alkyl group. The heteroarylalkyl radical may be attached to the main structure at any carbon atom from alkyl group that results in the creation of a stable structure.

The term "heterocyclyl" refers to a heterocylic ring radical as defined above. The heterocylcyl ring radical may be attached to the main structure at any heteroatom or carbon atom that results in the creation of a stable structure.

The term "heterocyclylalkyl" refers to a heterocylic ring radical as defined above directly bonded to alkyl group. The heterocyclylalkyl radical may be attached to the main structure at carbon atom in the alkyl group that results in the creation of a stable structure.

The term "cyclic ring" refers to a cyclic ring containing 3–10 carbon atoms.

The term "protecting group" refers to carbobenzyloxy (CBZ) or Tert.butyloxy carbonyl (BOC) and the like.

The term "halogen" refers to radicals of fluorine, chlorine, bromine and iodine.

Pharmaceutically acceptable salts forming part of this invention include salts derived from inorganic bases such as Li, Na, K, Ca, Mg, Fe, Cu, Zn, Mn; salts of organic bases such as N,N'-diacetylethylenediamine, glucamine, triethylamine, choline, hydroxide, dicyclohexylamine, metformin, benzylamine, trialkylamine, thiamine, and the like; chiral bases like alkylphenylamine, glycinol, phenyl glycinol and the like, salts of natural amino acids such as glycine, alanine, valine, leucine, isoleucine, norleucine, tyrosine, cystine, cysteine, methionine, proline, hydroxy proline, histidine, omithine, lysine, arginine, serine, and the like; quaternary ammonium salts of the compounds of invention with alkyl halides, alkyl sulphats like MeI, (Me)$_2$SO$_4$ and the like. non-natural amino acids such as D-isomers or substituted amino acids; guanidine, substituted guanidine wherein the substituents are selected from nitro, amino, alkyl, alkenyl, alkynyl, ammonium or substituted ammonium salts and aluminum salts. Salts may include acid addition salts where appropriate which are, sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, ketoglutarates and the like. Pharmaceutically acceptable solvates may be hydrates or comprise other solvents of crystallization such as alcohols.

The term inflammatory disorder generally refers to diseases and conditions induced by or associated with an excessive secretion of TNF-α and/or PDE-4. Another object of the invention is a method of treating inflammatory diseases, disorders and conditions characterized by or associated with an undesirable inflammatory immune response and diseases and conditions induced by or associated with an excessive secretion of TNF-α and/or PDE-4, which comprises administering to a subject a therapeutically effective amount of a compound according to Formula 1.

Another object of the invention is a method of treating inflammatory conditions and immune disorders in a subject in need thereof which comprises administering to said subject a therapeutically effective amount of a compound according to Formula 1.

Preferred inflammatory disorders are chosen from the group consisting of asthma, bronchial asthma, chronic obstructive pulmonary disease, allergic rhinitis, eosinophilic granuloma, nephritis, rheumatoid arthritis, cystic fibrosis, chronic bronchitis, multiple sclerosis, Crohns disease, psoraisis, uticaria, adult vernal cojunctivitis, respiratory distress syndrome, rhematoid spondylitis, osteoarthritis, gouty arthritis, uteltis, allergic conjunctivitis, inflammatory bowel conditions, ulcerative coalitis, eczema, atopic dermatitis and chronic inflammation. Further preferred are allergic inflammatory conditions.

Further preferred inflamatory disorders include, but are not limited to, chronic abstructive pulmonary disease (COPD) and asthma.

Further preferred are inflammatory conditions and immune disorders selected from the group consisting of inflammatory conditions or immune disorders of the lungs, joints, eyes, bowels, skin and heart.

Further preferred are inflammatory conditions chosen from the group consisting of bronchial asthma, nepritis, and allergic rhinitis.

Another object of the invention is a method for abating inflammation in an affected organ or tissue including delivering to the organ or tissue a therapeutically effective amount of a compound represented by a compound according to Formula 1.

Another object of the invention is a method of treating diseases of the central nervous system in a subject in need thereof which comprises administering to said subject a therapeutically effective amount of a compound according to Formula 1.

Preferred diseases of the central nervous system are chosen from the group consisting of depression, amnesia, dementia, Alzheimers disease, cardiac failure, shock and cerebrovascular disease.

Another object of the invention is a method of treating insulin resistant diabetes in a subject in need thereof which comprises administering to said subject a therapeutically effective amount of a compound according to Formula 1.

"Treating" or "treatment" of a state, disorder or condition includes:

(1) preventing or delaying the appearance of clinical symptoms of the state, disorder or condition developing in a mammal that may be afflicted with or predisposed to the state, disorder or condition but does not yet experience or display clinical or subclinical symptoms of the state, disorder or condition;

(2) inhibiting the state, disorder or condition, i.e., arresting or reducing the development of the disease or at least one clinical or subclinical symptom thereof; or (3) relieving the disease, i.e., causing regression of the state, disorder or condition or at least one of its clinical or subclinical symptoms.

The benefit to a subject to be treated is either statistically significant or at least perceptible to the patient or to the physician.

A "therapeutically effective amount" means the amount of a compound that, when administered to a mammal for treating a state, disorder or condition, is sufficient to effect such treatment. The "therapeutically effective amount" will vary depending on the compound, the disease and its severity and the age, weight, physical condition and responsiveness of the mammal to be treated.

The four classic symptoms of acute inflammation are redness, elevated temperature, swelling, and pain in the affected area, and loss of function of the affected organ.

Symptoms and signs of inflammation associated with specific conditions include:

rheumatoid arthritis—pain, swelling, warmth and tenderness of the involved joints; generalized and morning stiffness;

insulin-dependent diabetes mellitus—insulitis; this condition can lead to a variety of complications with an inflammatory component, including: retinopathy, neuropathy, nephropathy; coronary artery disease, peripheral vascular disease, and cerebrovascular disease;

autoimmune thyroiditis—weakness, constipation, shortness of breath, puffiness of the face, hands and feet, peripheral edema, bradycardia;

multiple sclerosis—spasticity, blurry vision, vertigo, limb weakness, paresthesias;

uveoretinitis—decreased night vision, loss of peripheral vision;

lupus erythematosus—joint pain, rash, photosensitivity, fever, muscle pain, puffiness of the hands and feet, abnormal urinalysis (hematuria, cylinduria, proteinuria), glomerulonephritis, cognitive dysfunction, vessel thrombosis, pericarditis;

scleroderma—Raynaud's disease; swelling of the hands, arms, legs and face; skin thickening; pain, swelling and stiffniess of the fingers and knees, gastrointestinal dysfunction, restrictive lung disease; pericarditis,; renal failure;

other arthritic conditions having an inflammatory component such as rheumatoid spondylitis, osteoarthritis, septic arthritis and polyarthritis—fever, pain, swelling, tenderness;

other inflammatory brain disorders, such as meningitis, Alzheimer's disease, AIDS dementia encephalitis—photophobia, cognitive dysfunction, memory loss;

other inflammatory eye inflammations, such as retinitis—decreased visual acuity;

inflammatory skin disorders, such as, eczema, other dermatites (e.g., atopic, contact), psoriasis, burns induced by UV radiation (sun rays and similar UV sources)—erythema, pain, scaling, swelling, tenderness;

inflammatory bowel disease, such as Crohn's disease, ulcerative colitis—pain, diarrhea, constipation, rectal bleeding, fever, arthritis;

asthma—shortness of breath, wheezing;

other allergy disorders, such as allergic rhinitis—sneezing, itching, runny nose conditions associated with acute trauma such as cerebral injury following stroke—sensory loss, motor loss, cognitive loss;

heart tissue injury due to myocardial ischemia—pain, shortness of breath;

lung injury such as that which occurs in adult respiratory distress syndrome—shortness of breath, hyperventilation, decreased oxygenation, pulmonary infiltrates;

inflammation accompanying infection, such as sepsis, septic shock, toxic shock syndrome—fever, respiratory failure, tachycardia, hypotension, leukocytosis;

other inflammatory conditions associated with particular organs or tissues, such as nephritis (e.g., glomerulonephritis)—oliguria, abnormal urinalysis;

inflamed appendix—fever, pain, tenderness, leukocytosis;

gout—pain, tenderness, swelling and erythema of the involved joint, elevated serum and/or urinary uric acid;

inflamed gall bladder—abdominal pain and tenderness, fever, nausea, leukocytosis;

chronic obstructive pulmonary disease—shortness of breath, wheezing;

congestive heart failure—shortness of breath, rales, peripheral edema;

Type II diabetes—end organ complications including cardiovascular, ocular, renal, and peripheral vascular disease, lung fibrosis—hyperventilation, shortness of breath, decreased oxygenation;

vascular disease, such as atherosclerosis and restenosis—pain, loss of sensation, diminished pulses, loss of function and alloimmunity leading to transplant rejection—pain, tenderness, fever.

Subclinical symptoms include without limitation diagnostic markers for inflammation the appearance of which may precede the manifestation of clinical symptoms. One class of subclinical symptoms is immunological symptoms, such as the invasion or accumulation in an organ or tissue of proinflammatory lymphoid cells or the presence locally or peripherally of activated pro-inflammatory lymphoid cells recognizing a pathogen or an antigen specific to the organ or tissue. Activation of lymphoid cells can be measured by techniques known in the art.

"Delivering" a therapeutically effective amount of an active ingredient to a particular location within a host means causing a therapeutically effective blood concentration of the active ingredient at the particular location. This can be accomplished, e.g., by local or by systemic administration of the active ingredient to the host.

"A subject" or "a patient" or "a host" refers to mammalian animals, preferably human.

Some of the representative compounds according to the present invention are specified below but should not construed to be limited thereto;

1. N-(3,5-dichloropyrid-4-yl)-4-methoxy-8-methanesulfonamido-dibenzo[b,d]furan-1-carboxamide
2. N-(3,5-dichloropyrid-4-yl)-4-methoxy-8-(N,N-dimethylsulphonamido)-dibenzo[b,d]furan-1-carboxamide
3. N-(3,5-dichloropyrid-4-yl)-4-methoxy-8-(ethanesulphonamido)-dibenzo[b,d]furan-1-carboxamide
4. N-(3,5-dichloropyrid-4-yl)-4-methoxy-8-acetamido-dibenzo[b,d]furan-1-carboxamide
5. N-(3,5-dichloropyrid-4-yl)-4-methoxy-8-(3-chloropropylcarboxamido)-dibenzo[b,d]furan-1-carboxamide
6. N-(3,5-dichloropyrid-4-yl)-4-methoxy-8-ethylcarboxamido-dibenzo[b,d]furan-1-carboxamide
7. N-(3,5-dichloropyrid-4-yl)-4-methoxy-8-t-butylcarboxamido-dibenzo[b,d]furan-1-carboxamide
8. N-(3,5-dichloropyrid-4-yl)-4-methoxy-8-ethoxycarbonylcarboxamido-dibenzo[b,d]furan-1-carboxamide
9. N-(3,5-dichloropyrid-4-yl)-4-methoxy-8-hydroxycarbonylcarboxamido-dibenzo[b,d]furan-1-carboxamide
10. N-(3,5-dichloropyrid-4-yl)-4-methoxy-8-hydroxycarbonylcarboxamido-dibenzo[b,d]furan-1-carboxamide sodium salt
11. N-(3,5-dichloropyrid-4-yl)-4-methoxy-8-(fur-2-yl-carboxamido)-dibenzo[b,d]furan-1-carboxamide
12. N-(3,5-dichloropyrid-4-yl)-4-methoxy-8-(cyclopropyl-carbonylamino)-dibenzo[b,d]furan-1-carboxamide
13. N-(3,5-dichloropyrid-4-yl)-4-methoxy-8-(N,N-dicyclopropylcarbonylamino)-dibenzo[b,d]furan-1-carboxamide
14. N-(3,5-dichloropyrid-4-yl)-4-methoxy-8-trifluoroacetamido-dibenzo[b,d]furan-1-carboxamide
15. N-(3,5-dichloropyrid-4-yl)-4-methoxy-8-ethoxycarboxamido-dibenzo[b,d]furan-1-carboxamide
16. N-(3,5-dichloropyrid-4-yl)-4-methoxy-8-isobutyloxycarboxamido-dibenzo[b,d]furan-1-carboxamide
17. N-(3,5-dichloropyrid-4-yl)-4-methoxy-8-phenoxycarboxamido-dibenzo[b,d]furan-1-carboxamide
18. N-(3,5-dichloropyrid-4-yl)-4-methoxy-8-cyclopropylmethoxycarboxamido-dibenzo[b,d]furan-1-carboxamide
19. N-(3,5-dichloropyrid-4-yl)-4-methoxy-8-trifluoromethylmethoxycarboxamido-dibenzo[b,d]furan-1-carboxamide
20. N-(3,5-dichloropyrid-4-yl)-4-methoxy-8-N,N-diethylaminocarboxamido-dibenzo[b,d]furan-1-carboxamide
21. N-(3,5-dichloropyrid-4-yl)-4-methoxy-8-cyclopentylaminocarboxamido-dibenzo[b,d]furan-1-carboxamide
22. N-(3,5-dichloropyrid-4-yl)-4-methoxy-8-(N-methylpiperazin-4-yl carboxamido-dibenzo[b,d]furan-1-carboxamide
23. N-(3,5-dichloropyrid-4-yl)-4-methoxy-8-(N-methylpiperazin-4-yl carboxamido-dibenzo[b,d]furan-1-carboxamide hydrochloride
24. N-(3,5-dichloropyrid-4-yl)-4-methoxy-8-(4-hydroxypiperidin-1-yl carboxamido-dibenzo[b,d]furan-1-carboxamide
25. N-(3,5-dichloropyrid-4-yl)-4-methoxy-8-(morphol-4-yl carboxamido-dibenzo[b,d]furan-1-carboxamide
26. N-(3,5-dichloropyrid-4-yl)-4-methoxy-8-isopropylamino carboxamido-dibenzo[b,d]furan-1-carboxamide
27. N-(3,5-dichloropyrid-4-yl)-4-methoxy-8-n-hexylamino carboxamido-dibenzo[b,d]furan-1-carboxamide
28. N-(3,5-dichloropyrid-4-yl)-4-methoxy-8-ethylamino carboxamido-dibenzo[b,d]furan-1-carboxamide
29. N-(3,5-dichloropyrid-4-yl)-4-methoxy-8-methylamino carboxamido-dibenzo[b,d]furan-1-carboxamide
30. N-(3,5-dichloropyrid-4-yl)-4-difluoromethoxy-8-methanesulfonamido-dibenzo[b,d]furan-1-carboxamide
31. N-(3,5-dichloropyrid-4-yl)-4-difluoromethoxy-8-methanesulfonamido-dibenzo[b,d]furan-1-carboxamide sodium salt
31(a) N-(3,5 dichloro pyrid-4-yl)-4-diflouro methoxy-8-meth and sulfonamido-[b,d] furan-1-carboxamide N-oxide
32. N-(3,5-dichloropyrid-4-yl)-4-difluoromethoxy-8-ethanesulfonamido-dibenzo[b,d]furan-1-carboxamide
33. N-(3,5-dichloropyrid-4-yl)-4-difluoromethoxy-8-N,N-dimethylaminosulfonamido-dibenzo[b,d]furan-1-carboxamide
34. N-(3,5-dichloropyrid-4-yl)-4-difluoromethoxy-8-acetamido-dibenzo[b,d]furan-1-carboxamide
35. N-(3,5-dichloropyrid-4-yl)-4-difluoromethoxy-8-(1-chloropropylcarboxamido)-dibenzo[b,d]furan-1-carboxamide
36. N-(3,5-dichloropyrid-4-yl)-4-difluoromethoxy-8-cyclopropylcarboxamido-dibenzo[b,d]furan-1-carboxamide
37. N-(3,5-dichloropyrid-4-yl)-4-difluoromethoxy-8-ethoxycarbonylcarboxamido-dibenzo[b,d]furan-1-carboxamide
38. N-(3,5-dichloropyrid-4-yl)-4-difluoromethoxy-8-hydroxycarbonylcarboxamido-dibenzo[b,d]furan-1-carboxamide
39. N-(3,5-dichloropyrid-4-yl)-4-difluoromethoxy-8-hydroxycarbonylcarboxamido-dibenzo[b,d]furan-1-carboxamide disodium salt
40. N-(3,5-dichloropyrid-4-yl)-4-difluoromethoxy-8-fur-2-ylcarboxamido-dibenzo[b,d]furan-1-carboxamide
41. N1-phenyl-4-methoxy-8-acetamido-dibenzo[b,d]furan-1-carboxamide
42. N1-(4-methoxyphenyl)-4-methoxy-8-acetamido-dibenzo[b,d]furan-1-carboxamide 43. N1-benzyl-4-methoxy-8-acetamido-dibenzo[b,d]furan-1-carboxamide
44. N-(3,5-dichloropyrid-4-yl)-4-methoxy-8-(ethylaminothiocarboxamido)-dibenzo[b,d]furan-1-carboxamide
45. N-(3,5-dichloropyrid-4-yl)-4-methoxy-8-(n-butylaminothiocarboxamido)-dibenzo[b,d]furan-1-carboxamide
46. N1-(pyrid-3-yl)-4-methoxy-8-acetamido-dibenzo[b,d]furan-1-carboxamide
47. N-(3,5-dichloropyrid-4-yl)-4-methoxy-8-acetamido-dibenzo[b,d]furan-1-carboxamide-N-oxide
48. N-(3,5-dichloropyrid-4-yl)-4-methoxy-8-methanesulfonamido-dibenzo[b,d]furan-1-carboxamide-N-oxide
49. N-(pyrid-4-yl)-4-methoxy-8-acetamido-dibenzo[b,d]furan-1-carboxamide
50. N-(3,5-dichloropyrid-4-yl)-4-methoxy-8-(2-ethoxy-2-oxo-ethylaminocarbonylamino)-dibenzo[b,d]furan-1-carboxamide
51. N-(3,5-dichloropyrid-4-yl)-4-methoxy-8-(2-hydroxy-2-oxo-ethylaminocarbonylamino)-dibenzo[b,d]furan-1-carboxamide
52. N-(3,5-dichloropyrid-4-yl)-4-methoxy-8-(2-ethoxy-2-oxo-ethylamino)-dibenzo[b,d]furan-1-carboxamide
53. N-(3,5-dichloropyrid-4-yl)-4-methoxy-8-(2-hydroxy-2-oxo-ethylamino)-dibenzo[b,d]furan-1-carboxamide
54. N-(3,5-dichloropyrid-4-yl)-1-methoxy-9-methyl-6-acetamido-9H-4-carbazolecarboxamide
55. N-(3,5-dichloropyrid-4-yl)-1-methoxy-9-methyl-6-methanesulphonamido-9H-4-carbazolecarboxamide
56. N-(3,5-dichloropyrid-4-yl)-1-methoxy-9-methyl-6-ethanesulphonamido-9H-4-carbazolecarboxamide
57. N-(3,5-dichloropyrid-4-yl)-1-methoxy-9-methyl-6-propionamido-9H-4-carbazolecarboxamide
58. N-(3,5-dichloropyrid-4-yl)-4-difluoromethoxy-8-methanesulfonamido-dibenzo[b,d]furan-1-carboxamide disodium salt
59. N-(3,5-dichloropyrid-4-yl)-1-methoxy-6-acetamido-dibenzo[b,d]thiophene-4-carboxamide
60. N-(3,5-dichloropyrid-4-yl)-4-difluoromethoxy-8-acetamido-dibenzo[b,d]furan-1-carboxamide sodium salt
61. N-(3,5-dichloropyrid-4-yl)-4-difluoromethoxy-8-fur-2-ylcarboxanido-dibenzo[b,d]furan-1-carboxamide sodium salt and pharmaceutically acceptable salts and N-oxides of the foregoing where applicable.

The compounds according to the invention may be prepared by the following processes. The symbols P, Ar, X, Y, $R^1$, $R^2$, $R^3$ and $R^4$ when used in the below Formulae are to be understood to present those groups described above in relation to Formula (1) unless otherwise indicated.

The present invention discloses a process for the preparation of compounds of general Formula (1).

(1)

In one embodiment, the desired compounds of the Formula (1) wherein Y is —CONR$^7$; $R^4$ is —NR$^5$R$^6$; P, Ar, X, Y, $R^1$, $R^2$, $R^3$, $R^5$, $R^6$ $R^7$ m and n are as described in the general description, can be synthesized from a common intermediate of the Formula (16).

The common intermediate of the Formula (16) can be synthesized by using the general process described in synthetic scheme I.

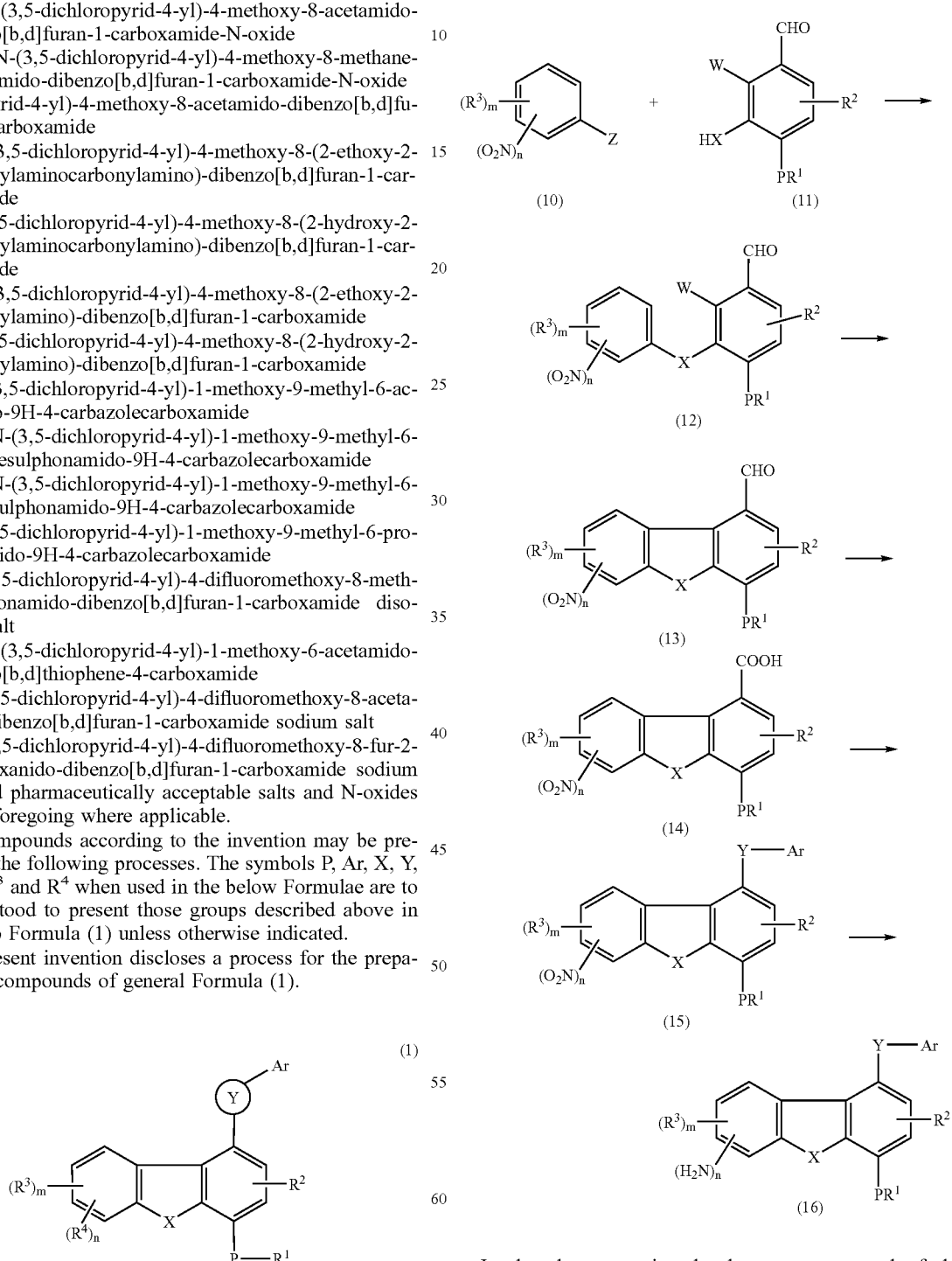

SYNTHETIC SCHEME I.

In the above mentioned scheme a compound of the general Formula (10) wherein Z is a halogen, preferably a fluorine, is reacted with a compound of the general Formula (11) wherein W is a halogen, preferably bromine or iodine, under basic conditions (potassium salts in DMF or DMSO, NaH in DMF or DMSO and the like) to obtain the intermediate of the general Formula (12). The intermediate of the general Formula (12) can be cyclised using metal compound or metal catalysed coupling conditions (palladium acetate in DMF or glacial acetic acid, nickel catalyst in pyridine or DMF, tetrakistriphenylphosphinepalladium in DMF and the like), preferably palladium acetate in DMF, to the tricyclic intermediate (13). The tricyclic intermediate of the general Formula (13) is then oxidized to the intermediate of the general Formula (14) using standard methods (such as sodium chlorite or potassium permanganate and the like) known in the literature. The intermediate of the general Formula (14) is then converted to the intermediate of the general Formula (15), wherein Y is —$CONR^7$, by reacting the appropriately activated carboxylic acid (acid halide or mixed anhydride or active ester) intermediate of the general Formula (14) with the optionally substituted aryl or heteroaryl amines ($ArNHR^7$) under appropriate basic conditions (NaH in DMF, diisopropylamine or triethylamine or pyridine in THF and the like) reported in the literature. The intermediate of the general Formula (15) is then reduced using conventional methods (raney nickel/hydrazine, iron/ammonium chloride, hydrogenation using Pd/C, and the like) known in the literature to the intermediate of the general Formula (16).

The intermediate of the general Formula (16) is then converted to the desired compound of the general Formula (1) wherein Y is —$CONR^7$, $R^4$ is —$NR^5R^6$; P, Ar, X, Y, $R^1$, $R^2$, $R^3$, $R^5$, $R^6$ $R^7$ m and n are the same as described in the general description, using the conventional methods known in the literature.

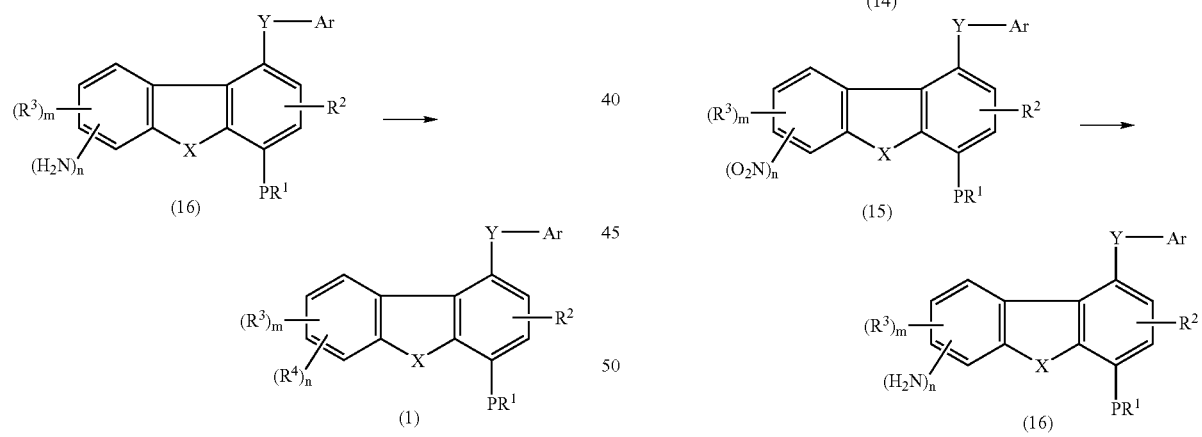

The desired compounds of the general Formula (1) obtained are then converted into their salts and/or the N-oxides by the action of m-chloro per benzoic acid or H2)2 and the like and, if desired, salts of the compounds of the Formula (1) obtained are then converted into the free form.

In another embodiment, the desired compounds of the Formula (1) wherein Y is —$CONR^7$; $R^4$ is —$NR^5R^6$; P, Ar, X, Y, $R^1$, $R^2$, $R^3$, $R^5$, $R^6$, $R^7$, m and n are the same as described in the general description, can be synthesized from a common intermediate of the Formula (16). The common intermediate of the Formula (16) can be synthesized by using the general process described in synthetic scheme II.

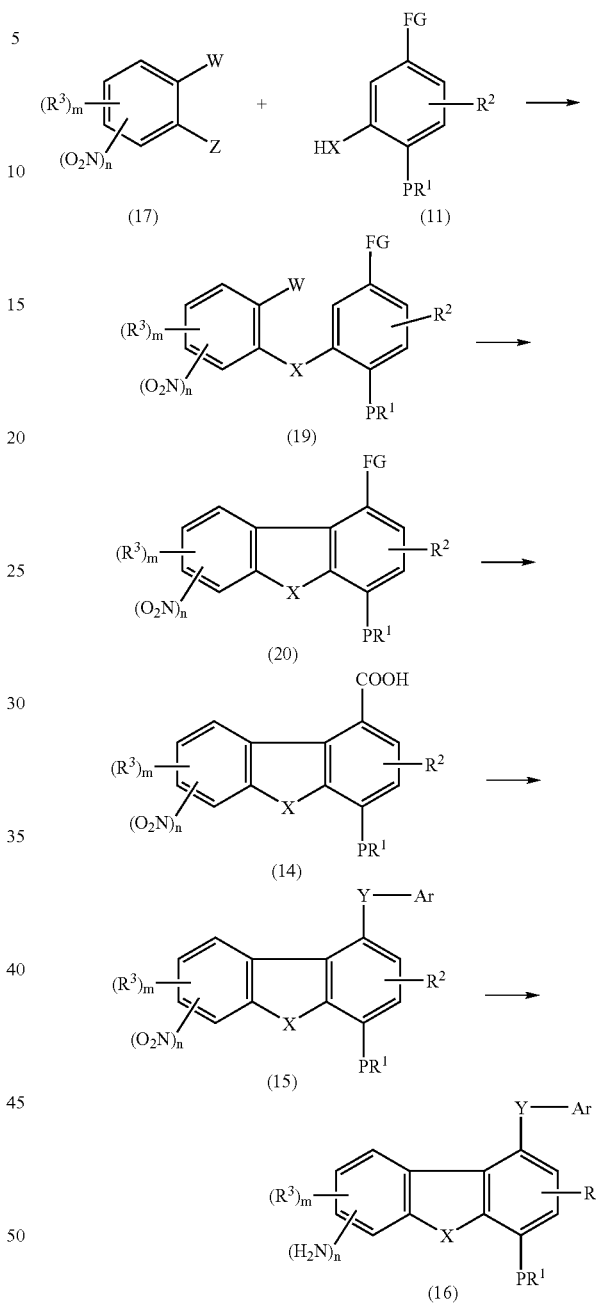

In the above mentioned scheme a compound of the general Formula (17) wherein Z is a halogen, preferably a fluorine, and wherein W is also a halogen, preferably bromine or iodine, is reacted with a compound of the general Formula (18) wherein FG is CHO, $COCH_3$, CN or —$COOR^a$, under basic conditions (potassium salts in DMF or DMSO, NaH in DMF or DMSO and the like) to obtain the intermediate of the general Formula (19). The intermediate of the general Formula (19) can be cyclised using metal compound or metal catalysed coupling conditions, nickel chloride, palladium acetate and the like preferably palladium acetate, to the tricyclic intermediate (20). The tricyclic intermediate of the general Formula (20) is then oxidized using KMnO₄, NaOCl₂ and the like to, if FG is CHO or COCH₃, or hydrolysed by using NaOH or H₂SO₄ to, if FG is CN or —COOR$^a$, the intermediate of the general Formula (14) using methods known in the literature. The intermediate of the general Formula (14) is then converted to the intermediate of the general Formula (15), wherein Y is —CONR⁷, by reacting the appropriately activated carboxylic acid (acid halide or mixed anhydride or active ester) intermediate of the general Formula (14) with the optionally substituted aryl or heteroaryl amines (ArNHR⁷) under appropriate basic conditions such as NaH in DMF or triethylamine and the like reported in the literature. The intermediate of the general Formula (15) is then reduced using the conventional methods known in the literature (palladium chloride or Raney nickel) to the intermediate of the general Formula (16).

The intermediate of the general Formula (16) is then converted to the desired compound of the general Formula (1) wherein Y is —CONR⁷, R⁴ is —NR⁵R⁶,; P, Ar, X, Y, R¹, R², R³, R⁵, R⁶, R⁷, m and n are the same as described in the general description, using conventional methods known in the literature.

The desired compounds of the general Formula (1) obtained are then converted into their salts and/or the N-oxides m-chloro per benzoic acid or H₂O₂ and the like and, if desired, salts of the compounds of the Formula (1) obtained are then converted into the free form.

In yet another embodiment, the desired compounds of the Formula (1) wherein Y is —CONR⁷, R⁴ is —NHCOCH₃, n=1; and P, Ar, X, Y, R¹, R², R³, R⁵, R⁶ R⁷ and m are the same as described in the general description, can be synthesized as in scheme III, Further the R⁴ wherein R⁴ is —NHCOCH₃ can be converted to, —NR⁵R⁶ using the methods known in the literature.

SYNTHETIC SCHEME III.

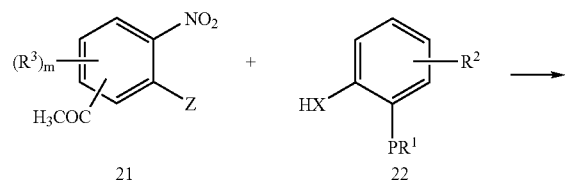

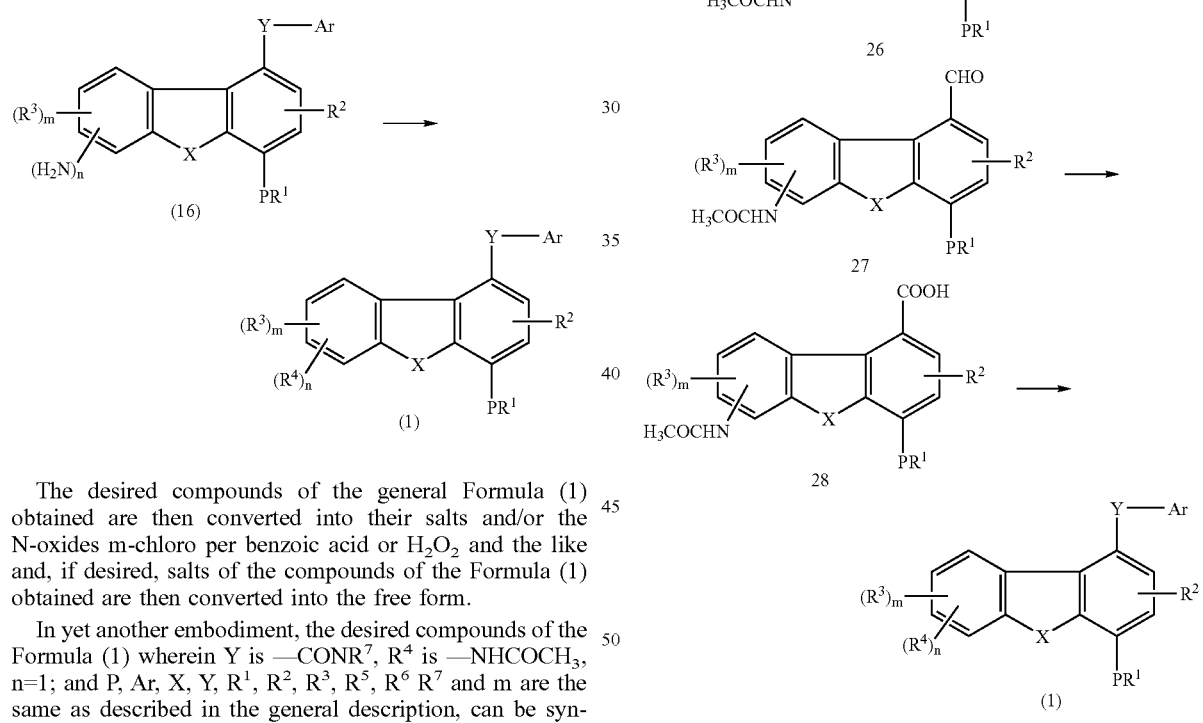

In the above mentioned scheme a compound of the Formula (21) wherein Z is a halogen, preferably a fluorine, is reacted with a compound of the general Formula (22) under basic conditions (potassium salts in DMF or DMSO, NaH in DMF or DMSO and the like) to obtain the intermediate of the general Formula (23). The intermediate of the general Formula (23) is then reduced to the intermediate of the general Formula (24) using standard reducing agents such as raney nickel/hydrazine or palladium on carbon in hydrogen atmosphere. The intermediate of the general Formula (24) is then cyclised to the tricyclic intermediate of the general Formula (25) by diazotization followed by standard coupling methods (cuprous oxide in 0.1N sulfuric acid, copper in DMSO). The acetyl group of tricyclic intermediate of the general Formula (25) is then converted to the acetamido group using Beckmann rearrangement to obtain the intermediate of the general Formula (26). The intermediate of the general Formula (26) is formylated using standard formylating conditions such as dichloromethyl methyl ether in tin (IV) chloride and the like to obtain the intermediate of the general Formula (27). The intermediate of the general Formula (27) is then oxidized using $KMnO^4$ or $NaOCl_2$ to the intermediate of the general Formula (28) using standard methods known in the literature. The intermediate of the general Formula (28) is then converted to the desired compound of the general Formula (1), wherein Y is —$CONR^7$, $R^4$ is —$NHCOCH_3$, n=1; and P, Ar, X, Y, $R^1$, $R^2$, $R^3$, $R^5$, $R^6$ $R^7$ and m are the same as described in the general description, by reacting the appropriately activated carboxylic acid (acid halide or mixed anhydride or active ester) intermediate of the general Formula (28) with the optionally substituted aryl or heteroaryl amines ($ArNHR^7$) using conventional methods known in the literature. Further the $R^4$ wherein $R^4$ is —$NHCOCH_3$ can be converted to, —$NR^5R^6$ using the methods known in the literature The desired compounds of the Formula (1) obtained are then converted into their salts and/or the N-oxides and, if desired, salts of the compounds of the Formula (1) obtained are then converted into the free form.

The N-oxidation is carried out in a manner likewise familiar to the person of ordinary skill in the art, e.g with the aid of m-chloroperoxybenzoic acid in dichloromethane at room temperature. The person of ordinary skill in the art is familiar with the reaction conditions which are necessary for carrying out the process on the basis of his knowledge.

The substances according to the invention are isolated and purified in a manner known per se, e.g. by distilling off the solvent in vacuum and recrystallizing the residue obtained from a suitable solvent or subjecting it to one of the customary purification methods, such as column chromatography on a suitable support material.

Salts are obtained by dissolving the free compound in a suitable solvent, e.g in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtering, reprecepitating, precipitating with a non-solvent for the addition salt or by evaporating the solvent. Salts obtained can be converted by basification or by acidifying into the free compounds which, in turn can be converted into salts.

In general, the ethereal solvents used in the above described processes for the preparation of compounds of the Formula (1) are selected from diethyl ether, 1,2-dimethoxyethane, tetrahydrofuran, diisopropyl ether, 1,4 dioxane and the like. The chlorinated solvent which may be employed may be selected from dichloromethane, 1,2-dichloroethane, chloroform, carbontetrachloride and the like. The aromatic solvents which may be employed may be selected from benzene and toluene. The alchoholic solvents which may be employed may be selected from methanol, ethanol, n-propanol, iso propanol, tert-butanol and the like. The aprotic solvents which may be employed may be selected from N,N-dimethylformamide, dimethyl sulfoxide and the like.

In general, the compounds prepared in the above described processes are obtained in pure form by using well known techniques such as crystallization using solvents such as pentane, diethyl ether, isopropyl ether, chloroform, dichloromethane, ethyl acetate, acetone, methanol, ethanol, isopropanol, water or their combinations, or column chromatography using alumina or silica gel and eluting the column with solvents such as hexane, petroleum ether (pet.ether), chloroform, ethyl acetate, acetone, methanol or their combinations.

Various polymorphs of a compound of general Formula (1) forming part of this invention may be prepared by crystallization of compound of Formula (1) under different conditions. example, using different solvents commonly used or their mixtures for recrystallization; crystallizations at different temperatures, various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffraction or such other techniques.

The present invention provides novel heterocyclic compounds, their analogs, their tautomers, their regioisomers, their stereoisomers, their enantiomers, their diastreomers, their polymorphs, their pharmaceutically acceptable salts, their appropriate N-oxides and their pharmaceutically acceptable solvates.

The present invention also provides pharmaceutical compositions, containing compounds of general Formula (1) as defined above, their derivatives, their analogs, their tautomeric forms, their stereoisomers, their polymorphs, their enantiomers, their diasteromers, their pharmaceutically acceptable salts or their pharmaceutically acceptable solvates in combination with the usual pharmaceutically employed carriers, diluents and the like. The pharmaceutical compositions according to this invention can be used for the treatment of allergic disorders.

It will be appreciated that some of the compounds of general Formula (1) defined above according to the invention can contain one or more asymmetrically substituted carbon atoms. The presence of one or more of these asymmetric centers in the compounds of general Formula (1) can give rise to stereoisomers and in each case the invention is to be understood to extend to all such stereoisomers, including enantiomers and diastereomers and their mixtures, including racemic mixtures. The invention may also contain E and Z geometrical isomers wherever possible in the compounds of general Formula (1) which includes the single isomer or mixture of both the isomers The pharmaceutical compositions may be in the forms normally employed, such as tablets, capsules, powders, syrups, solutions, suspensions and the like and may contain flavorants, sweeteners etc. in suitable solid or liquid carriers or diluents, or in suitable sterile media to form injectable solutions or suspensions. The active compounds of Formula (1) will be present in such pharmaceutical compositions in the amounts sufficient to provide the desired dosage in the range as described above. Thus, for oral administration, the compounds of Formula (1) can be combined with a suitable solid, liquid carrier or diluent to form capsules, tablets, powders, syrups, solutions, suspensions and the like. The pharmaceutical compositions, may, if desired, contain additional components such as flavorants, sweeteners, excipients and the like. For parenteral administration, the compounds of the Formula (1) can be combined with sterile aqueous or organic media to form injectable solutions or suspensions. For example, solutions in sesame or peanut oil, aqueous propylene glycol and the like can be used as well as aqueous solutions of water-soluble pharmaceutically-acceptable acid addition salts or salts with base of the compounds of Formula (1) The injectable solutions prepared in this manner can then be administered intravenously, intraperitoneally, subcutaneously, or intramuscularly, with intramuscular administration being preferred in humans.

The compounds can also be administered by inhalation when application within the respiratory tract is intended. Formulation of the present compounds is especially significant for respiratory inhalation, wherein the compound of Formula (1) is to be delivered in the form of an aerosol under pressure. It is preferred to micronize the compound of Formula (1) after it has been homogenised, e.g., in lactose, glucose, higher fatty acids, sodium salt of dioctylsulfosuccinic acid or, most preferably, in carboxymethyl cellulose, in order to achieve a microparticle size of 5 μm or less for the majority of particles. For -continued

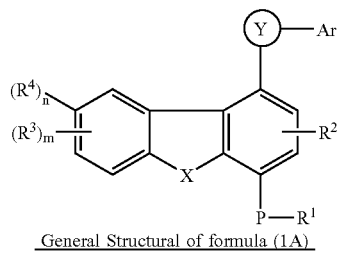

General Structural of formula (1A)

| Ex. No. | P | X | Y | Ar | m | n | R¹ | R² | R³ | R⁴ | Salt |
|---|---|---|---|---|---|---|---|---|---|---|---|
| 5. | O | O | —CONH | 3,5-dichloropyridin-4-yl | 0 | 1 | CH₃ | H | — | —NHC(O)CH₂CH₂CH₂Cl | — |
| 6. | O | O | —CONH | 3,5-dichloropyridin-4-yl | 0 | 1 | CH₃ | H | — | —NHC(O)CH₂CH₃ | — |
| 7. | O | O | —CONH | 3,5-dichloropyridin-4-yl | 0 | 1 | CH₃ | H | — | —NHC(O)C(CH₃)₃ | — |
| 8. | O | O | —CONH | 3,5-dichloropyridin-4-yl | 0 | 1 | CH₃ | H | — | —NHC(O)C(O)OC₂H₅ | — |
| 9. | O | O | —CONH | 3,5-dichloropyridin-4-yl | 0 | 1 | CH₃ | H | — | —NHC(O)C(O)OH | — |
| 10. | O | O | —CONH | 3,5-dichloropyridin-4-yl | 0 | 1 | CH₃ | H | — | —NHC(O)C(O)OH | Na |
| 11. | O | O | —CONH | 3,5-dichloropyridin-4-yl | 0 | 1 | CH₃ | H | — | —NHC(O)-(2-furyl) | — |

-continued

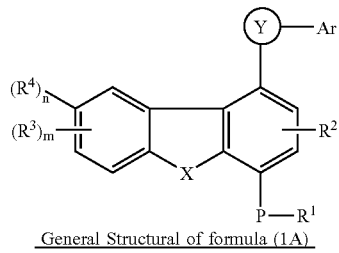
General Structural of formula (1A)

| Ex. No. | P | X | Y | Ar | m | n | R¹ | R² | R³ | R⁴ | Salt |
|---|---|---|---|---|---|---|---|---|---|---|---|
| 12. | O | O | —CONH | 3,5-dichloropyridin-4-yl | 0 | 1 | CH₃ | H | — | cyclopropanecarboxamido | — |
| 13. | O | O | —CONH | 3,5-dichloropyridin-4-yl | 0 | 1 | CH₃ | H | — | N,N-bis(cyclopropanecarbonyl)amino | — |
| 14. | O | O | —CONH | 3,5-dichloropyridin-4-yl | 0 | 1 | CH₃ | H | — | trifluoroacetamido | — |
| 15. | O | O | —CONH | 3,5-dichloropyridin-4-yl | 0 | 1 | CH₃ | H | — | ethoxycarbonylamino | — |
| 16. | O | O | —CONH | 3,5-dichloropyridin-4-yl | 0 | 1 | CH₃ | H | — | isobutoxycarbonylamino | — |
| 17. | O | O | —CONH | 3,5-dichloropyridin-4-yl | 0 | 1 | CH₃ | H | — | phenoxycarbonylamino | — |
| 18. | O | O | —CONH | 3,5-dichloropyridin-4-yl | 0 | 1 | CH₃ | H | — | cyclopropylmethoxycarbonylamino | — |

-continued

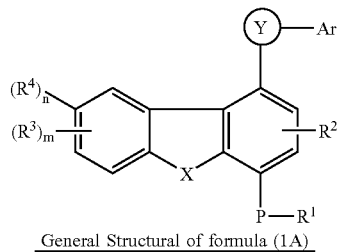

General Structural of formula (1A)

| Ex. No. | P | X | Y | Ar | m | n | R¹ | R² | R³ | R⁴ | Salt |
|---|---|---|---|---|---|---|---|---|---|---|---|
| 19. | O | O | —CONH | 3,5-dichloropyridin-4-yl | 0 | 1 | CH₃ | H | — | —NH-C(=O)-O-CH₂CF₃ | — |
| 20. | O | O | —CONH | 3,5-dichloropyridin-4-yl | 0 | 1 | CH₃ | H | — | —NH-C(=O)-N(Et)₂ | — |
| 21. | O | O | —CONH | 3,5-dichloropyridin-4-yl | 0 | 1 | CH₃ | H | — | —NH-C(=O)-NH-cyclopentyl | — |
| 22. | O | O | —CONH | 3,5-dichloropyridin-4-yl | 0 | 1 | CH₃ | H | — | —NH-C(=O)-(4-methylpiperazin-1-yl) | — |
| 23. | O | O | —CONH | 3,5-dichloropyridin-4-yl | 0 | 1 | CH₃ | H | — | —NH-C(=O)-(4-methylpiperazin-1-yl) | HCl |
| 24. | O | O | —CONH | 3,5-dichloropyridin-4-yl | 0 | 1 | CH₃ | H | — | —NH-C(=O)-(4-hydroxypiperidin-1-yl) | — |
| 25. | O | O | —CONH | 3,5-dichloropyridin-4-yl | 0 | 1 | CH₃ | H | — | —NH-C(=O)-morpholin-4-yl | — |

-continued

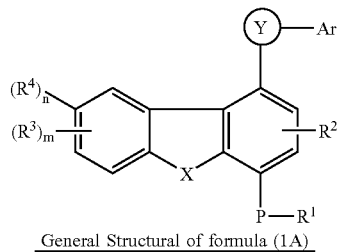
General Structural of formula (1A)

| Ex. No. | P | X | Y | Ar | m | n | R¹ | R² | R³ | R⁴ | Salt |
|---|---|---|---|---|---|---|---|---|---|---|---|
| 26. | O | O | —CONH | 3,5-dichloropyridin-4-yl | 0 | 1 | $CH_3$ | H | — | —NHC(O)NH-iPr | — |
| 27. | O | O | —CONH | 3,5-dichloropyridin-4-yl | 0 | 1 | $CH_3$ | H | — | —NHC(O)NH-n-hexyl | — |
| 28. | O | O | —CONH | 3,5-dichloropyridin-4-yl | 0 | 1 | $CH_3$ | H | — | —NHC(O)NHEt | — |
| 29. | O | O | —CONH | 3,5-dichloropyridin-4-yl | 0 | 1 | $CH_3$ | H | — | —NHC(O)NHMe | — |
| 30. | O | O | —CONH | 3,5-dichloropyridin-4-yl | 0 | 1 | $CHF_2$ | H | — | —NHS(O)$_2$Me | — |
| 30a | O | O | —CONH | 3,5-dichloropyridin-4-yl N-oxide | 0 | 1 | $CHF_2$ | H | — | —NHS(O)$_2$Me | — |
| 31. | O | O | —CONH | 3,5-dichloropyridin-4-yl | 0 | 1 | $CHF_2$ | H | — | —NHS(O)$_2$Me | Na |

-continued

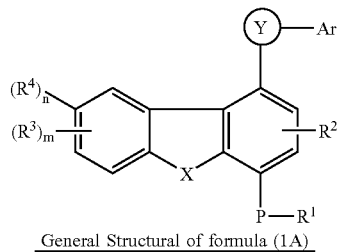

General Structural of formula (1A)

| Ex. No. | P | X | Y | Ar | m | n | R¹ | R² | R³ | R⁴ | Salt |
|---|---|---|---|---|---|---|---|---|---|---|---|
| 32. | O | O | —CONH | 3,5-dichloropyridin-4-yl | 0 | 1 | $CHF_2$ | H | — | —NHSO$_2$Et | — |
| 33. | O | O | —CONH | 3,5-dichloropyridin-4-yl | 0 | 1 | $CHF_2$ | H | — | —NHSO$_2$N(CH$_3$)$_2$ | — |
| 34. | O | O | —CONH | 3,5-dichloropyridin-4-yl | 0 | 1 | $CHF_2$ | H | — | —NHC(O)CH$_3$ | — |
| 35. | O | O | —CONH | 3,5-dichloropyridin-4-yl | 0 | 1 | $CHF_2$ | H | — | —NHC(O)(CH$_2$)$_3$Cl | — |
| 36. | O | O | —CONH | 3,5-dichloropyridin-4-yl | 0 | 1 | $CHF_2$ | H | — | —NHC(O)-cyclopropyl | — |
| 37. | O | O | —CONH | 3,5-dichloropyridin-4-yl | 0 | 1 | $CHF_2$ | H | — | —NHC(O)C(O)OC$_2$H$_5$ | — |
| 38. | O | O | —CONH | 3,5-dichloropyridin-4-yl | 0 | 1 | $CHF_2$ | H | — | —NHC(O)C(O)OH, | — |

-continued
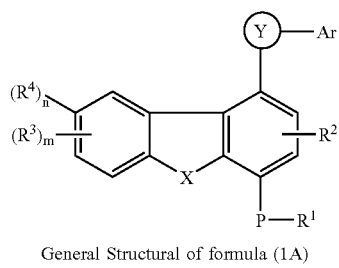
General Structural of formula (1A)
| Ex. No. | P | X | Y | Ar | m | n | R¹ | R² | R³ | R⁴ | Salt |
|---|---|---|---|---|---|---|---|---|---|---|---|
| 39. | O | O | —CONH | 3,5-dichloropyridin-4-yl | 0 | 1 | CHF₂ | H | — | -NHC(O)C(O)OH | 2 Na |
| 40. | O | O | —CONH | 3,5-dichloropyridin-4-yl | 0 | 1 | CHF₂ | H | — | -NHC(O)-(2-furyl) | — |
| 41. | O | O | —CONH | phenyl | 0 | 1 | CH₃ | H | — | -NHC(O)CH₃ | — |
| 42. | O | O | —CONH | 4-methoxyphenyl | 0 | 1 | CH₃ | H | — | -NHC(O)CH₃ | — |
| 43. | O | O | —CONH | benzyl | 0 | 1 | CH₃ | H | — | -NHC(O)CH₃ | — |
| 44. | O | O | —CONH | 3,5-dichloropyridin-4-yl | 0 | 1 | CH₃ | H | — | -NHC(S)NHEt | — |
| 45. | O | O | —CONH | 3,5-dichloropyridin-4-yl | 0 | 1 | CH₃ | H | — | -NHC(S)NH-n-butyl | — |

-continued

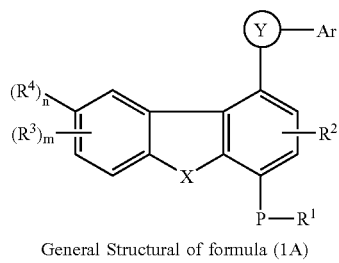

General Structural of formula (1A)

| Ex. No. | P | X | Y | Ar | m | n | R¹ | R² | R³ | R⁴ | Salt |
|---|---|---|---|---|---|---|---|---|---|---|---|
| 46. | O | O | —CONH | 3-pyridyl | 0 | 1 | $CH_3$ | H | — | NHC(O)CH₃ (acetamido) | — |
| 47. | O | O | —CONH | 3,5-dichloropyridin-4-yl N-oxide | 0 | 1 | $CH_3$ | H | — | NHC(O)CH₃ (acetamido) | — |
| 48. | O | O | —CONH | 3,5-dichloropyridin-4-yl N-oxide | 0 | 1 | $CH_3$ | H | — | NHS(O)₂CH₃ (methanesulfonamido) | — |
| 49. | O | O | —CONH | 4-pyridyl | 0 | 1 | $CH_3$ | H | — | NHC(O)CH₃ (acetamido) | — |
| 50. | O | O | —CONH | 3,5-dichloropyridin-4-yl | 0 | 1 | $CH_3$ | H | — | NHC(O)NHCH₂C(O)OEt | — |
| 51. | O | O | —CONH | 3,5-dichloropyridin-4-yl | 0 | 1 | $CH_3$ | H | — | NHC(O)NHCH₂C(O)OH | — |
| 52. | O | O | —CONH | 3,5-dichloropyridin-4-yl | 0 | 1 | $CH_3$ | H | — | NHCH₂C(O)OEt, | — |

-continued

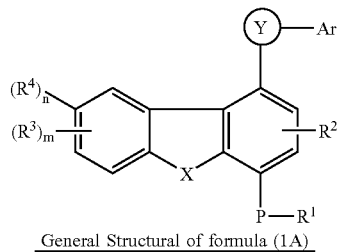

General Structural of formula (1A)

| Ex. No. | P | X | Y | Ar | m | n | R¹ | R² | R³ | R⁴ | Salt |
|---|---|---|---|---|---|---|---|---|---|---|---|
| 53. | O | O | —CONH | 3,5-dichloropyridin-4-yl | 0 | 1 | $CH_3$ | H | — | —NH—CH₂—COOH | — |
| 54. | O | N—$CH_3$ | —CONH | 3,5-dichloropyridin-4-yl | 0 | 1 | $CH_3$ | H | — | —NH—C(O)—$CH_3$ | — |
| 55. | O | N—$CH_3$ | —CONH | 3,5-dichloropyridin-4-yl | 0 | 1 | $CH_3$ | H | — | —NH—S(O)₂—$CH_3$ | — |
| 56. | O | N—$CH_3$ | —CONH | 3,5-dichloropyridin-4-yl | 0 | 1 | $CH_3$ | H | — | —NH—S(O)₂—$CH_2CH_3$ | — |
| 57. | O | N—$CH_3$ | —CONH | 3,5-dichloropyridin-4-yl | 0 | 1 | $CH_3$ | H | — | —NH—C(O)—$CH_2CH_3$ | — |
| 58. | O | O | —CONH | 3,5-dichloropyridin-4-yl | 0 | 1 | $CHF_2$ | H | — | —NH—S(O)₂—$CH_3$ | 2 Na |
| 59. | O | S | —CONH | 3,5-dichloropyridin-4-yl | 0 | 1 | $CH_3$ | H | — | —NH—C(O)—$CH_3$ | — |

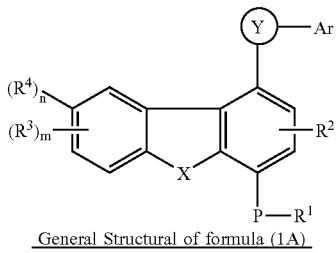

General Structural of formula (1A)

| Ex. No. | P | X | Y | Ar | m | n | R¹ | R² | R³ | R⁴ | Salt |
|---|---|---|---|---|---|---|---|---|---|---|---|
| 60. | O | O | —CONH | 3,5-dichloropyrid-4-yl | 0 | 1 | $CHF_2$ | H | — | NHC(O)CH₃ | Na |
| 61. | O | O | —CONH | 3,5-dichloropyrid-4-yl | 0 | 1 | $CHF_2$ | H | — | NHC(O)-furan-2-yl | Na |

The following intermediates have been used to synthesize the representative examples of the compounds of the invention.

Intermediate 1

N-(3,5-dichloropyrid-4-yl)-4-methoxy-8-amino dibenzo[b,d]furan-1-carboxamide

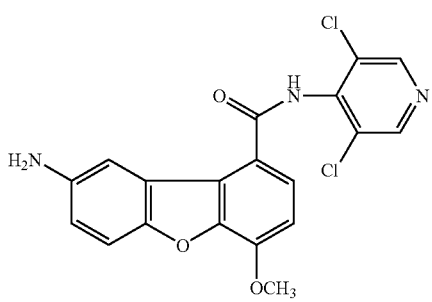

Step 1: 2-Bromoisovanillin

Isovanillin (5 gm, 0.033 mol) was dissolved in glacial acetic acid (30 ml). Anhydrous sodium acetate (5.4 gm) was added to the above solution followed by powdered iron (0.15 gm). The system was flushed thoroughly with nitrogen. A solution of bromine (5.79 gm, 0.0362 mol) in glacial acetic acid (10 ml) was added to the above stirred suspension at room temperature over a period of 15 min. The reaction mixture was stirred at room temperature for 45 min. The reaction mixture was poured into aqueous 2% sodium bisulfite (200 ml) and stirred for 10 min. The precipitate was filtered washed with water (100 ml), and dried to obtain 3.5 gm of 2-bromoisovanillin as white powder mp: (200–202° C.).

IR (KBr) 3233, 2990, 2891, 2844, 1669, 1593, 1564, 1494, 1463, 1286, 1238, 1205, 1019, 987, 805, 786 cm⁻¹.

¹H NMR (300 MHz, CDCl₃) δ 3.99 (s, 3H), 6.13 (s, 1H), 6.89 (d, 1H, J=8.4 Hz), 7.55 (d, 1H, J=8.4 Hz), 10.23 (s, 1H).

Step 2: 2-Bromo-3-(p-nitrophenoxy)-4-methoxy benzaldehyde

To a stirred suspension of potassium fluoride (1.89 gm, 0.0326 mol) in dry DMSO (10 ml) was added a solution of 2-bromoisovanillin (5.0 gm, 0.0217 mol) in DMSO (10 ml). A solution of 4-fluoronitrobenzene (5.0 gm, 0.0260 mol) in DMSO (5 ml) was added to the above suspension and the reaction mixture was stirred at 140° C. for 4 h. The reaction mixture was cooled to room temperature and the contents were poured into water (150 ml) and extracted with ethyl acetate (50 ml×3). The organic extracts were combined and washed with 1N sodium hydroxide (25 ml×2), water and brine and dried over anhydrous sodium sulfate. The dried organic layer was concentrated in vacuo and the residue was purified by silica-gel column chromatography using 20% ethyl acetate-petroleum ether as the eluent to give 2-bromo-3-(p-nitrophenoxy)-4-methoxy benzaldehyde as a pale yellow solid (5.0 gm) mp: 132–140° C.

IR (KBr) 3084, 2874, 1689, 1584, 1506, 1486, 1348, 1285, 1253, 1234, 1114, 1025, 848, 815, 747 cm⁻¹.

¹H NMR (300 MHz, CDCl₃) δ 3.86 (s, 3H), 6.89 (d, 2H, J=7.2 Hz), 7.07 (d, 1H, J=9.0 Hz), 7.92 (d, 1H, J=8.4 Hz), 8.17 (d, 2H, J=9.0 Hz), 10.24 (s, 1H).

Step 3: 4-methoxy-8-nitro-1-formyl dibenzo[b,d]furan

2-Bromo-3-(p-nitrophenoxy)-4-methoxy benzaldehyde (3.5 gm, 0.0087 mol), anhydrous sodium carbonate (1.125 gm, 0.0106 mol) and palladium (II) acetate (0.19 gm, 0.0008 mol), in dimethylacetamide (15 ml) are heated and stirred under nitrogen at 170° C. for 2 h. Water (90 ml) is added to the cooled reaction mixture. The precipitated solid is collected by filtration and washed with 5% hydrochloric acid followed by water. The product was obtained as a yellow solid (3.4 gm).

IR (KBr) 3115, 2925, 2856, 1682, 1609, 1576, 1522, 1343, 1295, 1076, 846, 829 cm$^{-1}$.

$^1$H NMR (300 MHz, DMSO) δ 4.13 (s, 3H), 7.53 (d, 1H, J=9.0 Hz), 8.01 (d, 1H, J=9.0 Hz), 8.16 (d, 1H, J=9.0 Hz), 8.48 (dd, 1H, J=9.0 Hz, 3.0 Hz), 9.79 (d, 1H, J=3.0 Hz), 10.1 (s, 1H).

Step 4: 4-methoxy-8-nitro dibenzo[b,d]furan-1-carboxylic acid 4-methoxy-8-nitro-1-formyl dibenzo[b,d]furan (1.1 gm, 0.0034 mol) in acetone (5 ml) was heated to 60–70° C. for 10 min. To the above suspension was added dropwise a hot solution of potassium permanganate (1.07 gm, 0.0068 mol) in water: acetone (1:3) (15 ml) for 10 min. The reaction was heated to 60–70° C. for 10 min., cooled to room temperature and filtered. The residue washed with acetone and the filtrate was extracted with 10% sodium hydroxide solution. Acidification, followed by filtration and washing of the precipitate yielded 4-methoxy-8-nitro-dibenzo[b,d]furan-1-carboxylic acid (0.6 gm) as white solid; mp: 178° C. (dec.)

IR (KBr) 3467, 2942, 1711, 1694, 1633, 1610, 1574, 1522, 1453, 1417, 1344, 1278, 1069, 846, 826, 743 cm$^{-1}$.

$^1$H NMR (300 MHz, DMSO) δ 4.08 (s, 3H), 7.36 (d, 1H, J=8.4 Hz), 7.98 (d, 1H, J=9.0 Hz), 8.07 (d, 1H, J=8.4 Hz), 8.44 (dd, 1H, J=9.0 Hz, 2.7 Hz), 9.79 (d, 1H, J=2.4 Hz),

Step 5a: 4-methoxy-8-nitro dibenzo[b,d]furan-1-carboxylic acid chloride

A suspension of 4-methoxy-8-nitro dibenzo[b,d]furan-1-carboxylic acid (150 mg, 0.52 mmol) (from step 4) in a mixture of benzene (2 ml) and freshly distilled thionyl chloride (2 ml) was heated to reflux temperature for 4 h. The excess thionyl chloride was removed under vacuum to get the corresponding acid chloride which was subjected the next reaction as such.

Step 5b: N-(3,5-dichloropyrid-4-yl)-4-methoxy-8-nitro dibenzo[b,d]furan-1-carboxamide To a pre-washed suspension of sodium hydride (52 mg, 2.5 equiv., 1.3 mmol, 60% oil dispersion) in DMF (2 ml) was added drop wise a solution of 4-amino-3,5-dichloropyridine (93 mg, 0.52 mmol) in DMF (2 ml) at −10° C. A pre-cooled solution of above acid chloride (0.52 mmol) (from step 5a) in THF (2 ml) was added, all at once, to the reaction mixture and the contents were stirred at −10° C. for 30 min. The reaction was quenched with brine, diluted with water and filtered to give a crude solid which was washed with ethanol to give N-(3,5-dichloropyrid-4-yl)-4-methoxy-8-nitro-dibenzo[b,d]furan-1-carboxamide as a white solid (80 mg); mp: 315–317° C.

IR (KBr): 3245, 3092, 2845, 1662, 1614, 1581, 1554, 1519, 1483, 1461, 1439, 1391, 1337, 1282, 1205, 1181, 1067 cm−1.

$^1$H NMR (300 MHz, DMSO) δ 4.12 (s, 3H), 7.48 (d, 1H, J=8.1 Hz), 8.03 (d, 1H, J=8.1 Hz), 8.06 (d, 1H, J=8.4 Hz), 8.44 (dd, 1H, J=7.2 Hz), 8.81 (s, 2H). 9.43 (d, 1H, J=1.2 Hz), 10.95 (s, 1H).

Step 6: N-(3,5-dichloropyrid-4-yl)-4-methoxy-8-amino-dibenzo[b,d]furan-1-carboxamide Iron powder (467 mg, 8.35 mmol) and ammonium chloride (742 mg, 13.5 mmol) were heated at 80° C. for 15 min. N-(3,5-pyrid-4-yl)-4-methoxy-8-nitro dibenzo[b,d]furan-1-carboxamide (800 mg, 1.85 mmol) was suspended in methanol and allowed to trickle down into the above reaction mixture at reflux. The reaction was refluxed for 3 h and filtered hot. Methanol was evaporated, and the solid was washed with water and taken directly without purification to synthesize the following examples.

Intermediate 2

N-(3,5-dichloropyrid-4-yl)-4-difluoromethoxy-8-amino dibenzo[b,d]furan-1-carboxamide

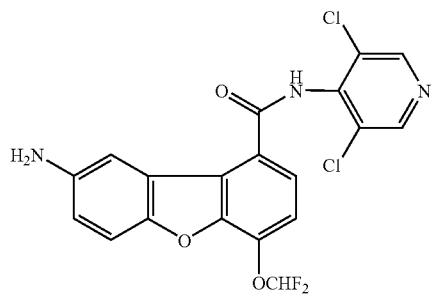

Step 1: 4-cyclopentoxy-3-hydroxy-benzaldehyde

A suspension of 3,4-dihydroxybenzaldehyde (5.0 gm, 0.0362 mol), anhydrous potassium carbonate (6.0 gm, 0.0434 mol) and cyclopentyl bromide (6.5 gm, 0.0434 mol) in dry DMF (50 ml) was heated and stirred at 80° C. for 24 hrs. Reaction mixture was then cooled and diluted with water (500 ml), acidified with 1N HCl and extracted with ethyl acetate (3×100 ml). The ethyl acetate extract was washed 5% sodium bicarbonate and brine and dried over anhydrous sodium sulfate. The dried extract on concentration afforded a residue which was purified by silica gel chromatography using 10% ethyl acetate in petroleum ether as the eluent to provide 5.0 gm of the title product as white solid. mp: 87–89° C.

IR (KBr) 2964, 1670, 1605, 1580, 1500, 1463, 1358, 1271, 1122, 976, 806, 748 cm$^{-1}$ $^1$H NMR (300 MHz, CDCl$_3$) δ 1.65–2.04 (m, 8H), 4.93 (m, 1H), 5.83 (s, 1H), 6.94 (d, 1H), 7.38–7.43 (m, 2H), 9.82 (s, 1H).

Step 2: 2-bromo-4-cyclopentoxy-3-hydroxy-benzaldehyde 4-cyclopentoxy-3-hydroxy-benzaldehyde (1.0 gm, 4.84 mmol) was dissolved in glacial acetic acid (20 ml). Anhydrous sodium acetate (0.8 gm, 9.7 mmol) was added to the above solution followed by powdered iron (0.022 gm). The system was flushed thoroughly with nitrogen. A solution of bromine (0.854 gm, 5.32 mmol) in glacial acetic acid (10 ml) was added to the above stirred suspension at 15° C. over a period of 15 min. The reaction mixture was stirred at 15° C. for 45 min. The reaction mixture was poured into aqueous 2% sodium bisulfite (100 ml) and stirred for 10 min. The precipitate was filtered washed with water (100 ml), and dried to obtain 800 mg of 2-bromo-4-cyclopentoxy-3-hydroxy-benzaldehyde as white powder mp: 107–109° C.

$^1$H NMR (300 MHz, CDCl$_3$) δ 1.66–2.03 (m, 8H), 4.92 (m, 1H), 6.15 (s, 1H), 6.90 (d, 1H), 7.54 (d, 1H), 10.25 (s, 1H).

Step 3: 2-bromo-4-cyclopentoxy-3-(p-nitrophenoxy)-benzaldehyde

To a stirred suspension of potassium fluoride (125 mg, 2.104 mmol) in dry DMSO (2.5 ml) was added a solution of 2-bromo-4-cyclopentoxy-3-hydroxy-benzaldehyde (500 mg, 1.754 mmol) in DMSO (2.5 ml). A solution of 4-fluoronitrobenzene (500 mg, 2.631 mmol) in DMSO (2.5 ml) was added to the above suspension and the reaction mixture was stirred at 140° C. for 6 h. The reaction mixture was cooled to room temperature and the contents were poured into water (100 ml) and extracted with ethyl acetate (50 ml×3). The organic extracts were combined and washed with 1N sodium hydroxide (25 ml×2), water and brine and dried over anhydrous sodium sulfate. The dried organic layer was concentrated in vacuo to give 2-bromo-3-(p-nitrophenoxy)-4-methoxy benzaldehyde as a pale yellow solid (500 mg) mp: 115–117° C.

$^1$H NMR (300 MHz, CDCl$_3$) δ 1.18–1.23 (m, 2H), 1.39–1.53 (m, 4H), 1.73–1.81 (m, 2H), 5.01 (m, 1H), 7.09 (dd, 2H), 7.43 (d, 1H), 7.87 (d, 1H), 8.24 (dd, 2H), 10.13 (s, 1H).

Step 4: 4-cyclopentyloxy-8-nitro-1-formyl dibenzo[b,d]furan

Intermediate 2-bromo-4-cyclopentoxy-3-(p-nitrophenoxy)-benzaldehyde (500 mg, 1.09 mmol), anhydrous sodium carbonate (150 mg, 1.325 mmol) and palladium (II) acetate (25 mg, 0.096 mmol), in dimethylformamide (10 ml) are heated and stirred under nitrogen at 130° C. for 7 h. Water (90 ml) is added to the cooled reaction mixture and extracted with ethyl acetate (2×25 ml). The combined organic layer was washed with 5% hydrochloric acid followed by water and dried over anhydrous sodium sulfate to afford the product as a yellow solid (200 mg). mp: 230–240° C.

$^1$H NMR (300 MHz, DMSO) δ 1.70 (m, 2H), 1.77–1.92 (m, 4H), 2.09 (m, 2H), 5.25 (m, 1H), 7.53 (d, 1H), 8.05 (d, 1H), 8.14 (d, 1H), 8.51 (d, 1H), 9.80 (s, 1H), 10.14 (s, 1H).

Step 5: 4-hydroxy-8-nitro-1-formyl dibenzo[b,d]furan 4-cyclopentyloxy-8-nitro-1-formyl dibenzo[b,d]furan (200 mg, 0.530 mol) was heated in HBr (47% in acetic acid) (5 ml) in glacial acetic acid (10 ml) at 50° C. for 7–8 h. The reaction contents were poured in ice-water (200 ml) and extracted with ethyl acetate (3×50 ml). The combined organic layer was washed with saturated sodium bicarbonate, and water and dried over anhydrous sodium sulfate. Removal of the organic solvent in vacuo afforded the crude product as a white solid (150 mg). The crude white solid was used as such without further purification. mp: >270° C.

$^1$H NMR (300 MHz, DMSO) δ 7.28 (d, 1H), 8.01 (d, 1H), 8.04 (d, 1H), 8.50 (d, 1H), 9.83 (s, 1H), 10.09 (s, 1H), 11.92 (s, 1H).

Step 6: 4-difluoromethoxy-8-nitro-1-formyl dibenzo[b,d]furan

A suspension of 4-hydroxy-8-nitro-1-formyl dibenzo[b,d]furan (150 mg, 0.485 mmol) and anhydrous potassium carbonate (200 mg, 1.455 mmol) in dry DMF (5.0 ml) was stirred at 80° C. for 10 min. Chlorodifluoromethane gas was purged into the reaction mixture for 45 min. The reaction mixture was cooled, diluted with water (50 ml), and extracted with ethyl acetate (3×25 ml). The combined organic layer was washed with water and dried over anhydrous sodium sulfate. Removal of the organic solvent in vacuo afforded the product as a white solid (150 mg). mp: 245–248° C.

Step 7: 4-difluoromethoxy-8-nitro dibenzo[b,d]furan-1-carboxylic acid 4-difluoromethoxy-8-nitro-1-formyl dibenzo[b,d]furan (150 mg, 0.48 mmol) in acetone (20 ml) and water (5 ml) was heated to 60–70° C. for 10 min. To the above solution was added dropwise a solution of potassium permanganate (150 mg, 0.973 mmol) in water (5 ml) for 10 min. The reaction was heated to 60–70° C. for 30 min., and filtered hot through celite bed. Acidification of the filtrate resulted in a precipitate which on filteration and washing with water yielded 4-difluoromethoxy-8-nitro-dibenzo[b,d]furan-1-carboxylic acid (100 mg) as white solid; mp: >270° C.

$^1$H NMR (300 MHz, DMSO) δ 7.61 (t, 1H, J=72 Hz), 7.60 (d, 1H), 8.07 (d, 1H), 8.13 (d, 1H), 8.52 (d, 1H), 9.77 (s, 1H), 13.80 (s, 1H).

Step 8: N-(3,5-dichloropyrid-4-yl)-4-difluoromethoxy-8-nitro-dibenzo[b,d]furan-1-carboxamide A solution 4-difluoromethoxy-8-nitro dibenzo[b,d]furan-1-carboxylic acid (100 mg, 0.30 mmol), in a mixture of benzene (2 ml) and freshly distilled thionyl chloride (2 ml) was heated to reflux temperature for 4 h. The excess thionyl chloride was removed under vacuum to get the corresponding acid chloride.

To a pre-washed suspension of sodium hydride (25 mg, 60% oil dispersion) in DMF (3 ml) was added dropwise a solution of 4-amino-3,5-dichloropyridine (53 mg, 0.30 mmol) in DMF (2 ml) at −10° C. A pre-cooled solution of above acid chloride (0.30 mmol) in THF (5 ml) was added, all at once, to the reaction mixture and the contents were stirred at −10° C. for 30 min. The reaction was quenched with brine, diluted with water and filtered to give a crude solid which was purified by silica gel chromatography using 10% acetone in chloroform as the eluent to provide 100 mg of N-(3,5-dichloropyrid-4-yl)-4-difluoromethoxy-8-nitro-dibenzo[b,d]furan-1-carboxamide as white solid. mp: >270° C.

IR (KBr): 3213, 2926, 1664, 1555, 1526, 1488, 1339, 1285, 1199, 1090, 904, 823 cm−1.

$^1$H NMR (300 MHz, DMSO) δ 7.63 (t, 1H, J=72 Hz), 7.77 (d, 1H), 8.09 (d, 1H), 8.13 (d, 1H), 8.52 (dd, 1H, J=9.3 Hz, 2.4 Hz), 8.86 (s, 2H), 9.39 (d, 1H, J=2.7 Hz), 11.21 (s, 1H).

Step 9: N-(3,5-dichloropyrid-4-yl)-4-difluoromethoxy-8-amino-dibenzo[b,d]furan-1-carboxamide A mixture of N-(3,5-dichloropyrid-4-yl)-4-difluoromethoxy-8-nitro-dibenzo[b,d]furan-1-carboxamide (step 8) (100 mg), methanol (10 ml) and 10% Pd/C (10 mg) was hydrogenated at 60 psi for 12 h. Filteration of the reaction mixture over celite bed and removal of solvent methanol under reduced pressure afforded N-(3,5-dichloropyrid-4-yl)-4-difluoromethoxy-8-amino-dibenzo[b,d]furan-1-carboxamide as white solid. mp: >270° C.

IR (KBr): 3436, 3360, 3185, 2921, 1659, 1555, 1484, 1391, 1292, 1195, 1133, 1055, 910, 811, 674 cm–1.

$^1$H NMR (300 MHz, DMSO) δ 5.14 (brs, 2H), 6.86 (dd, 1H, J=8.7 Hz, 2.4 Hz), 7.53 (t, 1H, J=72 Hz), 7.46–7.51 (m, 2H), 7.80 (d, 1H, J=9.0 Hz), 8.80 (s, 2H), 10.96 (s, 1H).

Intermediate 3

N-(3,5-dichloropyrid-4-yl)-1-methoxy-9-methyl-6-amino-9H-4-carbazolecarboxamide

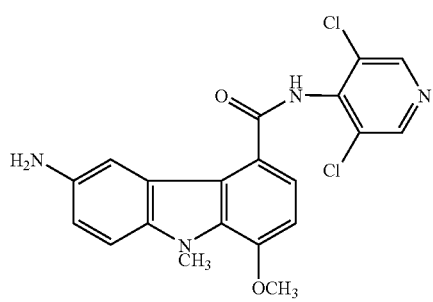

Step 1: methyl-3-(2-bromo-4-nitroanilino)-4-methoxybenzoate 3-amino-4-methoxy methyl benzoate (3.5 gm, 0.0193 mol) (commercial) was dissolved in DMF (20 ml) and added to a suspension of sodium hydride (60% dispersion) (1.54 gm, 0.0386 mol) in DMF (20 ml). The reaction mixture was stirred under nitrogen for 30 minutes at room temperature, followed by addition of a solution of 3-bromo-4-fluoro nitrobenzene (5.05 gm, 0.0231 mol) in DMF (20 ml) at 0° C. over a period of 10 minutes. The reaction was stirred at room temperature for 18 hrs. The reaction was then quenched with brine and diluted with ice cold water (500 ml) to get a precipitate which was filtered and dried to get the crude product. The crude product was purified by column chromatography using 40% ethyl acetate in petroleum ether as eluent to get pure product as a yellow solid.

IR (KBr): 3363, 3103, 3005, 2952, 2951, 1720, 1600, 1581, 1506, 1492, 1443, 1327, 1295, 1255, 1144, 1117, 1103, 1020, 1003, 824, 760, 743 cm$^{-1}$.

$^1$H NMR (300 MHz, DMSO): δ 3.83 (s, 3H), 3.85 (s, 3H), 6.50 (d, 1H, J=9.0 Hz), 7.29 (d, 1H, J=9.0 Hz), 7.86 (s, 1H), 8.01 (d, 1H, J=7.2 Hz), 8.03 (d, 1H, J=7.2 Hz), 8.19 (s, 1H), 8.37(s, 1H).

Step 2: methyl-1-methoxy-6-nitro-9H-4-carbazolecarboxylate

Methyl-3-(2-bromo-4-nitroanilino)-4-methoxybenzoate (3 gm, 0.0093 mol), anhydrous sodium carbonate (2.96 gm, 0.0275 mol) and palladium (II) acetate (1 gm, 0.0046 mol), in dimethylformamide (60 ml) were heated and stirred under nitrogen at 140° C. for 18 hr. The reaction mixture was cooled and filtered through celite bed. Water (90 ml) was added to the cooled reaction mixture. The precipitated solid was acidified and collected by filtration and washed with water. The product was obtained as a yellow solid (3.4 gm).

IR (KBr): 3404, 3133, 3017, 2964, 1724, 1626, 1615, 1571, 1513, 1461, 1435, 1318, 1267, 1231, 1200, 1070, 920, 741 cm$^{-1}$.

$^1$H NMR (300 MHz, DMSO): δ 3.99 (s, 3H), 4.11 (s, 3H), 7.24 (d, 1H, J=8.7 Hz), 7.67 (d, 1H, J=9.0 Hz), 8.01 (d, 1H, J=9.0 Hz), 8.34 (dd, 1H, J=8.7 and 2.4 Hz), 9.95 (d, 1H, J=2.4 Hz), 12.57 (s, 1H).

Step 3: methyl-1-methoxy-9-methyl-6-nitro-9H-4-carbazolecarboxylate

Methyl-1-methoxy-6-nitro-9H-4-carbazolecarboxylate (1 gm, 0.0026 mol) was dissolved in DMF (10 ml) and added to a suspension of sodium hydride (104 mg, 0.0052 mol) in DMF (10 ml) at room temperature over a period of 10 minutes. Solution of methyl iodide (549 mg, 0.0039 mol) in DMF (10 ml) was added to the reaction mixture and it was stirred further for a period of 1 hr. The reaction was then quenched with brine and diluted with water The precipitate obtained was acidified and then filtered to get a yellow solid.

IR (KBr): 3131, 2943, 2846, 1730, 1618, 1572, 1514, 1438, 1324, 1251, 1136, 1068, 1017, 809, 740 cm$^{-1}$.

$^1$H NMR (300 MHz, DMSO): δ 3.97 (s, 3H), 4.05 (s, 3H), 4.19 (s, 3H), 7.22 (d, 1 H, J=8.7 Hz), 7.75 (d, 1H, J=9.0 Hz), 7.95 (d, 1H, J=9.0 Hz), 8.34 (dd, 1H, J=8.7 and 2.4 Hz), 9.90 (d, 1H, J=2.4 Hz).

Step 4: 1-methoxy-9-methyl-6-nitro-9H-4-carbazolecarboxylic acid

Methyl-1-methoxy-9-methyl-6-nitro-9H-4-carbazolecarboxylate (500 mg) was suspended in methanol (15 ml) and added with 1 M NaOH (10 ml). The reaction mixture was refluxed for 18 hrs. Methanol was evaporated and the compound was diluted with water followed by addition of HCl. The precipitate was filtered to get a brown solid.

$^1$H NMR (300 MHz, DMSO): δ 4.06 (s, 3H), 4.23 (s, 3H), 7.24 (d, 1H, J=8.7 Hz), 7.82 (d, 1H, J=9.0 Hz), 7.95 (d, 1H, J=9.0 Hz), 8.36 (dd, 1H, J=9.0 and 2.4 Hz), 10.03 (d, 1H, J=2.4 Hz), 13.01 (brs, 1H).

Step 4a: 1-methoxy-9-methyl-6-nitro-9H-4-carbazolecarboxy acid chloride 1-methoxy-9-methyl-6-nitro-9H-4-carbazolecarboxylic acid (300 mg) was suspended in freshly distilled thionyl chloride (2 ml) was heated to reflux temperature for 4 hr. The excess thionyl chloride was removed under vacuum to get the corresponding acid chloride which was subjected the next reaction as such.

Step 5: N-(3,5-dichloropyrid-4-yl)—1-methoxy-9-methyl-6-nitro-9H-4-carbazolecarboxamide To a pre-washed suspension of sodium hydride (100 mg, 2.5 equiv., 0.0025, 60% oil dispersion) in DMF (3 ml) was added drop wise a solution of 4-amino-3,5-dichloropyridine (244 mg, 0.0015 mol) in DMF (3 ml) at −10° C. A pre-cooled solution of above acid chloride (from step 4a) in THF (5 ml) was added, all at once, to the reaction mixture at −50° C. and the contents were stirred at −50° C. for 1 hr. The reaction was quenched with brine, diluted with water and filtered to give N-(3,5-dichloropyrid-4-yl)-1-methoxy-9-methyl-6-nitro-9H-4-carbazolecarboxamide as a yellow solid (250 mg); mp: >250° C.

IR (KBr): 3432, 3199, 2936, 2841, 1662, 1575, 1513, 1479, 1398, 1323, 1313, 1275, 1254, 1095, 1067, 1018, 809, 745 cm$^{-1}$.

$^1$H NMR (300 MHz, DMSO): δ 4.08 (s, 3H), 4.25 (s, 3H), 7.32 (d, 1H, J=8.4 Hz), 7.76–7.83 (m, 2H), 8.36 (dd, 1H, J=9.0 and 2.4 Hz), 8.84 (s, 2H), 10.03 (d, 1H, J=2.4 Hz), 10.89 (s, 1H).

Step 6: N-(3,5-dichloropyrid-4-yl)-1-methoxy-9-methyl-6-amino-9H-4-carbazolecarboxamide N-(3,5-dichloropyrid-4-yl)—1-methoxy-9-methyl-6-nitro-9H-4-carbazolecarboxamide (250 mg) was suspended in DMF (20 ml) and methanol (10 ml) and added with raney nickel (25 mg, 10% w/w) and reduced under pressure (60 psi) for 18 hrs at room temperature. The reaction mixture was filtered through celite and DMF was evaporated to get a green solid which was washed with water to give N-(3,5-dichloropyrid-4-yl)-1-methoxy-9-methyl-6-amino-9H-4-carbazolecarboxamide. Confirmed by ninhydrin. The compound was taken directly without purification to synthesize the following example no 54,55,56 and 57

Representative compounds of the invention, which should not be construed as limiting in any way, are found at Table I General Structure of Formula (1A).

EXAMPLE 1

N-(3,5-dichloropyrid-4-yl)-4-methoxy-8-methanesulfonamido-dibenzo[b,d]furan-1-carboxamide

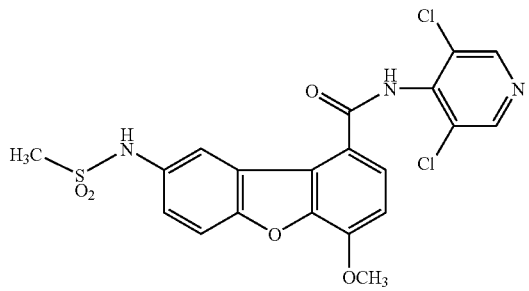

N-(3,5-dichloropyrid-4-yl)-4-methoxy-8-amino-dibenzo[b,d]furan-1-carboxamide (100 mg, 0.249 mmol) (intermediate 1) was treated with methanesulfonyl chloride (24 mg, 0.299 mol) in THF (10 ml) containing pyridine (23 mg, 0.299 mmol) at 0° C. and allowed to warm to room temperature. The reaction was stirred at room temperature for 30 min. THF was evaporated and the residue was washed with saturated sodium bicarbonate solution, water. The solid obtained was purified by silica gel column chromatography using 30% acetone-chloroform as eluent to obtain 30 mg of N-(3,5-dichloropyrid-4-yl)-4-methoxy-8-methanesulfonylamido-dibenzo[b,d]furan-1-carboxamide as white solid; mp: 315° C.

IR (KBr): 3272, 3147, 2925, 1661, 1607, 1490, 1393, 1313, 1288, 1145, 1101, 810 cm$^{-1}$.

$^1$H NMR (300 MHz, DMSO) δ 2.91 (s, 3H), 4.07 (s, 3H), 7.35 (d, 1H, J=8.4 Hz), 7.44 (d, 1H, J=8.4 Hz), 7.73 (d, 1H, J=8.4 Hz), 7.80 (d, 1H, J=8.4 Hz), 8.31 (s, 1H), 8.77 (s, 2H), 9.65 (s, 1H), 10.80 (s, 1H).

Example 2 and 3 were synthesized using reaction conditions similar to Example 1 except for using the appropriate substituted sulfonyl chloride instead of methanesulfonyl chloride.

EXAMPLE 2

N-(3,5-dichloropyrid-4-yl)-4-methoxy-8-(N,N-dimethylaminosulphonamido)-dibenzo[b,d]furan-1-carboxamide

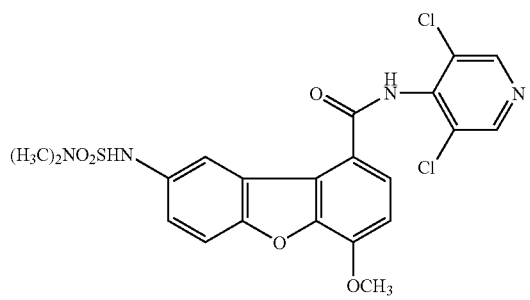

IR (KBr): 3370, 2922, 1675, 1608, 1483, 1278, 1147, 963, 899, 801, 701 cm$^{-1}$.

$^1$H NMR (300 MHz, DMSO) δ 2.65 (s, 6H), 4.07 (s, 3H), 7.33 (d, 1H, J=8.7 Hz), 7.43 (dd, 1H, J=8.7 and 1.8 Hz), 7.68 (d, 1H, J=8.7 Hz), 7.88 (d, 1H, J=8.7 Hz), 8.31 (d, 1H, J=1.8 Hz), 8.77 (s, 2H), 9.82 (s, 1H), 10.79 (s, 1H).

EXAMPLE 3

N-(3,5-dichloropyrid-4-yl)-4-methoxy-8-(ethanesulphonamido)-dibenzo[b,d]furan-1-carboxamide

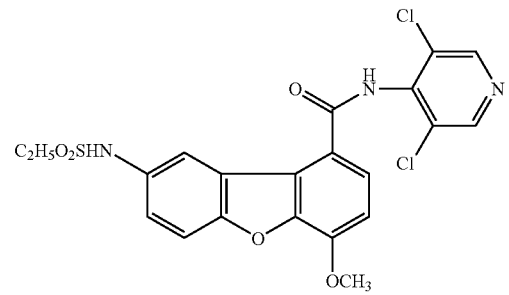

$^1$H NMR (300 MHz, DMSO-d$_6$) δ 1.19(t, 3H, J=7.2 Hz), δ 2.99 (q, 2H, J=7.5Hz), δ 4.07 (s, 3H), δ 7.36 (d, 1H, J=8.4 Hz), δ 7.41 (dd, 1H, J=8.7 Hz and J=2.4 Hz), δ 7.72 (d, 1H, J=8.7 Hz), δ 7.91 (d, 1H, J=8.4 Hz), δ 8.32 (d, 1H, J=2.4 Hz), δ 8.77 (s, 2H), δ 9.73 (s, 1H), δ 10.80 (s, 1H).

IR (KBr) 3304, 2968, 2933, 1680, 1608, 1484, 1461, 1332, 1282, 1196, 1143, 1101, 1022, 957, 810, 780, cm−1

EXAMPLE 4

N-(3,5-dichloropyrid-4-yl)-4-methoxy-8-acetamido-dibenzo[b,d]furan-1-carboxamide

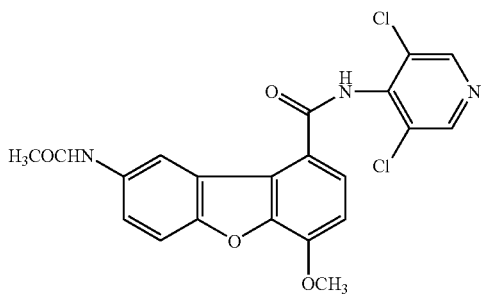

N-(3,5-dichloropyrid-4-yl)-4-methoxy-8-amino-dibenzo[b,d]furan-1-carboxamide (100 mg, 0.249 mmol) (intermediate 1) was treated with acetyl chloride (22 mg, 0.299 mmol) in THF (10 ml) containing pyridine (23 mg, 0.299 mmol) at 0° C. and allowed to warm to room temperature. The reaction was stirred at room temperature for 30 min. THF was evaporated and the residue was washed with saturated sodium bicarbonate solution and water. The solid obtained was purified by silica gel column chromatography using 30% acetone-chloroform as eluent to obtain 25 mg of N-(3,5-dichloropyrid-4-yl)-4-methoxy-8-acetamido-dibenzo[b,d]furan-1-carboxamide as white solid; mp: 252° C.

IR (KBr): 3271, 2961, 2925, 2852, 1660, 1607, 1542, 1499, 1468, 1392, 1285, 1261, 1101, 1021, 805 cm$^{-1}$.

$^1$H NMR (300 MHz, DMSO) δ 2.01 (s, 3H), 4.07 (s, 3H), 7.32 (d, 1H, J=8.4 Hz), 7.65 (d, 1H, J=8.4 Hz), 7.93 (m, 2H), 8.41 (s, 1H), 8.76 (s, 2H), 10.06 (s, 1H), 10.76 (s, 1H).

Example 5, 6, 7, 8, 11, 12 and 13 were synthesized using reaction conditions similar to Example 4 except for using the appropriate substituted acid chloride instead of acetyl chloride.

EXAMPLE 5

N-(3,5-dichloropyrid-4-yl)-4-methoxy-8-(3-chloropropylcarboxamido)-dibenzo[b,d]furan-1-carboxamide

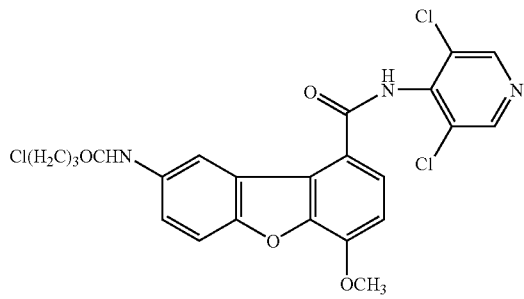

IR (KBr): 3244, 2940, 1655, 1606, 1543, 1493, 1446, 1393, 1283, 1222, 1199, 1099, 1022, 936, 810, 722, 670, 575 cm$^{-1}$ $^1$HNMR (300 MHz, DMSO): δ 2.00 (m, 2H), 2.50 (t, 2H), 3.7 (t, 2H), 4.07 (s, 3H), 7.34 (d, 1H, J=8.4 Hz), 7.68 (d, 1H, J=8.7 Hz) 7.94 (d, 1H, J=8.4 Hz), 7.94 (d, 1H, J=8.7 Hz) 8.44 (s, 1H, J=2.4 Hz) 8.76 (s, 2H,), 10.12 (s, 1H), 10.77 (s, 1H).

EXAMPLE 6

N-(3,5-dichloropyrid-4-yl)-4-methoxy-8-ethylcarboxamido-dibenzo[b,d]furan-1-carboxamide

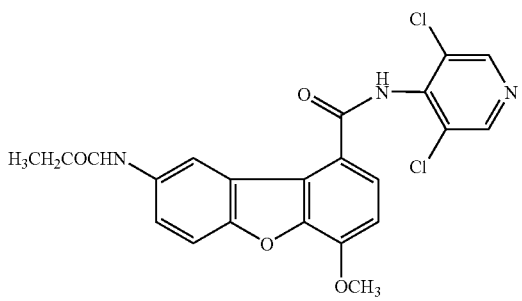

IR (KBr): 3302, 2937, 1649, 1607, 1500, 1392, 1196, 1103, 809, 723 cm$^{-1}$ $^1$H NMR (300 MHz, DMSO) δ 1.10 (t, 2H), 2.34 (q, 3H), 4.07 (s, 3H), 7.33 (d, 1H, J=9 Hz), 7.66 (d, 1H), 7.97–7.91 (m, 2H), 8.44 (s, 1H, J=2.4 Hz), 8.75 (s, 2H), 9.95 (s, 1H), 10.72 (s, 1H).

EXAMPLE 7

N-(3,5-dichloropyrid-4-yl)-4-methoxy-8-t-butylcarboxamido-dibenzo[b,d]furan-1-carboxamide

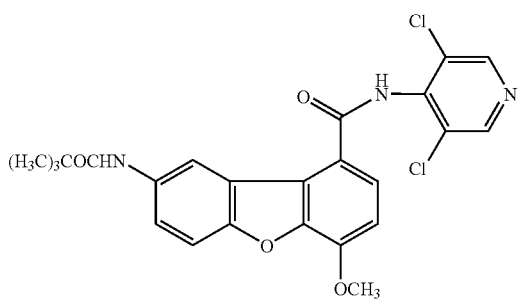

IR (KBr): 3327, 3201, 2958, 1647, 1606, 1522, 1495, 1444, 1395, 1289, 1197, 1099, 1025, 936, 806, 779, 670, 540 cm$^{-1}$ $^1$H NMR (300 MHz, DMSO) δ 1.22 (s, 9H), 4.07 (s, 3H), 7.33 (d, 1H, J=9 Hz), 7.66 (d, 1H) 7.79 (d, 1H, J=8.7 Hz), 7.93 (d, 1H, J=9 Hz), 8.51 (s, 1H, J=2.4 Hz), 8.75 (s, 2H). 9.38 (s, 1H), 10.71 (s, 1H).

EXAMPLE 8

N-(3,5-dichloropyrid-4-yl)-4-methoxy-8-ethoxycarbonylcarboxamido-dibenzo[b,d]furan-1-carboxamide

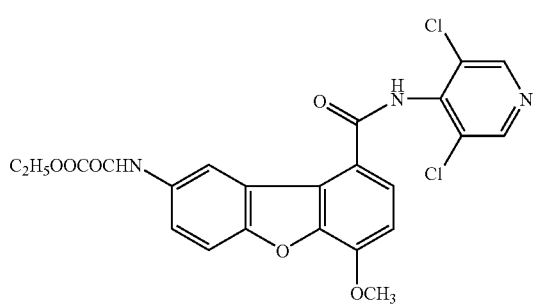

IR (KBr): 3349, 3214, 2928, 1753, 1708, 1671, 1606, 1392, 1281, 1199, 1183, 1022, 806, 685 cm$^{-1}$ $^1$HNMR (300 MHz, DMSO) δ 1.33 (t, 3H), 4.08 (s, 3H), 4.32 (q, 2H), 7.37 (d, 1H, J=8.4 Hz), 7.75 (d, 1H, J=8.7 Hz), 7.88 (d, 1H, J=9 Hz), 7.95 (d, 1H, J=8.1 Hz), 8.69 (s, 1H, J=1.8 Hz) 8.77 (s, 2H,) 10.78 (s, 1H), 10.95 (s, 1H).

EXAMPLE 9

N-(3,5-dichloropyrid-4-yl)-4-methoxy-8-hydroxycarbonylcarboxamido-dibenzo[b,d]furan-1-carboxamide

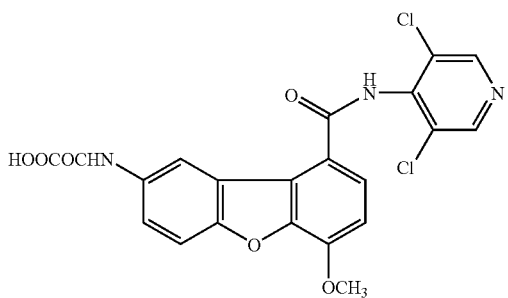

Was synthesized by hydrolysis of N-(3,5-dichloropyrid-4-yl)-4-methoxy-8-ethoxycarbonylcarboxamido-dibenzo[b,d]furan-1-carboxamide (Example 8) using potassium hydroxide (3 eq.) in methanol.

mp: >250° C.

This was directly used for preparation of Example 10 without further characterisation.

EXAMPLE 10

N-(3,5-dichloropyrid-4-yl)-4-methoxy-8-hydroxycarbonylcarboxamido-dibenzo[b,d]furan-1-carboxamide sodium salt

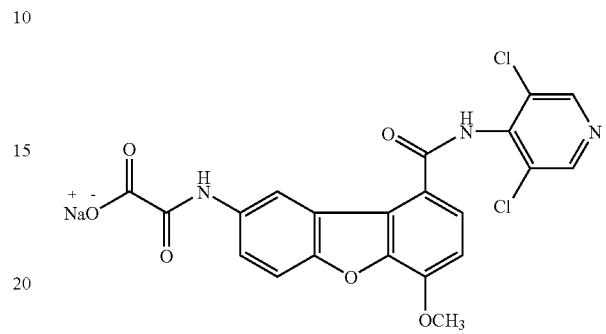

Was synthesized from N-(3,5-dichloropyrid-4-yl)-4-methoxy-8-hydroxycarbonyl carboxamido-dibenzo[b,d]furan-1-carboxamide (Example 9) using 1% methanolic sodium hydroxide (1.0 eq.).

$^1$HNMR (300 MHz, DMSO) δ 4.08 (s, 3H), 7.32 (d, 1H, J=8.4 Hz), 7.68 (d, 1H, J=8.7 Hz), 7.92 (d, 2H), 8.62 (s, 1H) 8.74 (s, 2H,) 10.19 (s, 1H), 10.80 (s, 1H).

EXAMPLE 11

N-(3,5-dichloropyrid-4-yl)-4-methoxy-8-(fur-2-ylcarboxamido)-dibenzo[b,d]furan-1-carboxamide

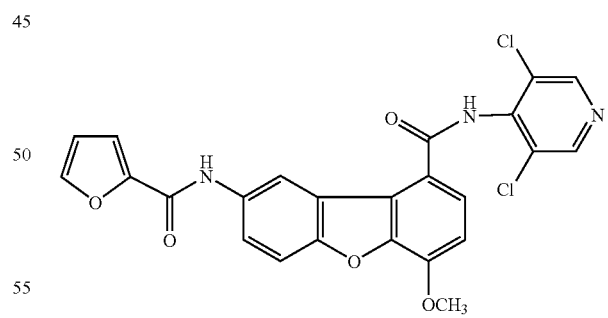

IR (KBr): 3247, 2925, 1660, 1606, 1566, 1548, 1491, 1465, 1391, 1333, 1221, 1093, 1023, 890, 814, 768, 611 cm$^{-1}$.

$^1$H NMR (300 MHz, DMSO) δ 4.08 (s, 3H), 6.68 (d, 1H, J=3.3 Hz), 7.36 (d, 2H, J=8.4 Hz), 7.74 (d, 1H, J=9.0 Hz), 7.95–7.89 (m, 3H), 8.66 (s, 1H, J=1.8 Hz), 8.76 (s, 2H,). 10.36 (s, 1H), 10.77 (s, 1H).

EXAMPLE 12

N-(3,5-dichloropyrid-4-yl)-4-methoxy-8-(cyclopropylcarbonylamino)-dibenzo[b,d]furan-1-carboxamide

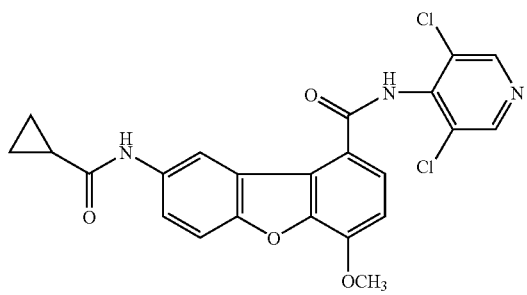

$^1$H NMR (300 MHz, DMSO-d$_6$) δ 0.77 (m, 4H), 1.80 (m, 1H), 4.08 (s, 3H), 7.36 (d, 1H, J=8.4 Hz), 7.69 (d, 1H, J=9.0 Hz), 7.80 (m, 2H), 8.47 (d, 1H, J=1.8 Hz), 8.79 (s, 2H), 10.34 (s, 1H), 10.80 (s, 1H).

IR (KBr) 3290, 3164, 1650, 1546, 1492, 1398, 1292, 1198, 1100, 960, 812, 640, cm$^{-1}$

EXAMPLE 13

N-(3,5-dichloropyrid-4-yl)-4-methoxy-8-(N,N-dicyclopropylcarbonylamino)-dibenzo[b,d]furan-1-carboxamide

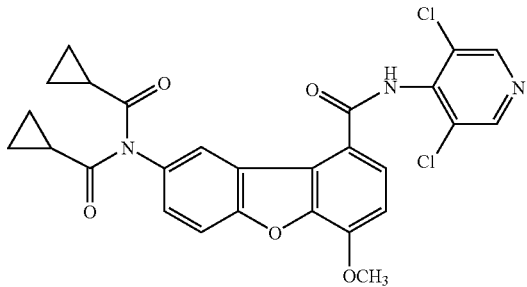

$^1$H NMR (300 MHz, DMSO-d$_6$) δ 0.98 (m, 4H), 1.14 (m, 4H), 1.82 (m, 1H), 2.12 (m, 1H), 4.07 (s, 3H), 7.19 (d, 1H, J=8.7 Hz), 7.58 (d, 1H, J=8.7 Hz), 7.68 (d, 1H, J=9.0 Hz), 8.28 (s, 1H), 8.79 (s, 2H), 10.40 (s, 1H).

IR (KBr) 3311, 3059, 3009, 2843, 1711, 1677, 1631, 1607, 1556, 1470, 1393, 1314, 1297, 1282, 1197, 1173, 1105, 1016, 810, 648, cm$^{-1}$

EXAMPLE 14

N-(3,5-dichloropyrid-4-yl)-4-methoxy-8-trifluoroacetamido-dibenzo[b,d]furan-1-carboxamide

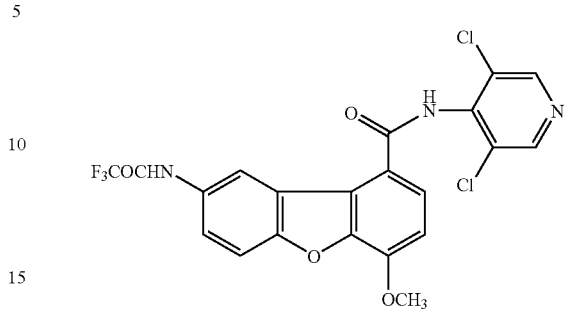

N-(3,5-dichloropyrid-4-yl)-4-methoxy-8-amino-dibenzo[b,d]furan-1-carboxamide (100 mg, 0.249 mmol) (intermediate 1) was treated with trifluoroacteic anhydride (57 mg, 0.27 mmol) in dichloromethane (5 ml) containing pyridine (19 mg, 0.25 mmol) at room temperature. The reaction was stirred at room temperature for 20 h. Dichloromethane was evaporated and the residue was triturated with cold water to obtain a white solid which was filtered. The solid was purified by silica gel column chromatography using 6% acetone-chloroform as eluent to obtain 30 mg of N-(3,5-dichloropyrid-4-yl)-4-methoxy-8-trifluoroacetamido-dibenzo[b,d]furan-1-carboxamide as white solid; mp: >300° C.

IR (KBr): 3281, 1717, 1668, 1608, 1500, 1394, 1290, 1203, 1154, 1099, 1024, 901, 809, 653 cm$^{-1}$ $^1$H NMR (300 MHz, DMSO) δ 4.09 (s, 3H), 7.38 (d, 1H, J=9 Hz), 7.80 (d, 1H), 7.89 (d, 1H, J=1.8 Hz), 7.98 (d, 1H, J=8.4 Hz), 8.67 (s, 1H, J=1.8 Hz), 8.76 (s, 2H), 10.77 (s, 1H), 11.42 (s, 1H).

EXAMPLE 15

N-(3,5-dichloropyrid-4-yl)-4-methoxy-8-ethoxycarboxamido-dibenzo[b,d]furan-1-carboxamide

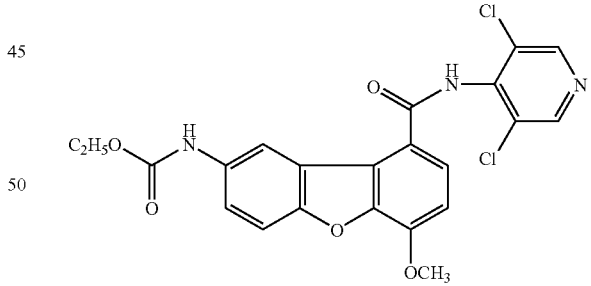

N-(3,5-dichloropyrid-4-yl)-4-methoxy-8-amino-dibenzo[b,d]furan-1-carboxamide (100 mg, 0.249 mmol) (intermediate 1) was treated with ethyl chloroformate (40 mg, 0.374 mmol) in THF (10 ml) containing pyridine (29 mg, 0.374 mmol) at 0° C. and allowed to warm to room temperature. The reaction was stirred at room temperature for 30 min. THF was evaporated and the residue was washed with water. The solid obtained was purified by silica gel column chromatography using 10% acetone-chloroform as eluent to obtain 40 mg of N-(3,5-dichloropyrid-4-yl)-4-methoxy-8-ethoxycarboxamido-dibenzo[b,d]furan-1-carboxamide as white solid; mp: 274° C.

IR (KBr): 3244, 3074, 2970, 2928, 1733, 1674, 1600, 1578, 1550, 1479, 1391, 1278, 1236, 1210, 1102, 1062, 803 cm$^{-1}$.

$^1$H NMR (300 MHz, DMSO) δ 1.24 (t, 3H), 4.07 (s, 3H), 4.08 (q, 2H), 7.32 (d, 1H, J=8.1 Hz), 7.60–7.67 (d, 2H), 7.88 (d, 1H, J=8.1 Hz), 8.45 (s, 1H), 8.76 (s, 2H), 9.62 (s, 1H), 10.76 (s, 1H).

Example 16 and 17 were synthesized using reaction conditions similar to Example 15 except for using the appropriately substituted chloroformate instead of ethyl chloroformate.

EXAMPLE 16

N-(3,5-dichloropyrid-4-yl)-4-methoxy-8-isobutyloxycarboxamido-dibenzo[b,d]furan-1-carboxamide

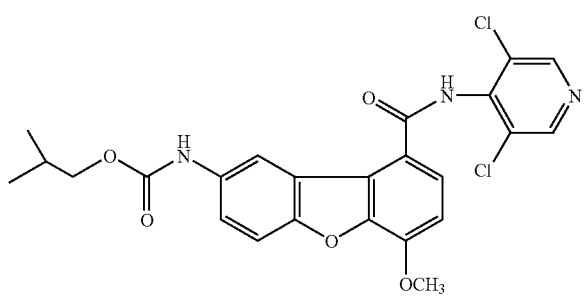

$^1$H NMR (300 MHz, DMSO-d$_6$) δ: 0.91 (d, J=6.6 Hz, 6H), 1.84–1.96 (m, 1H), 3.84 (d, J=6.9 Hz, 2H), 4.08 (s, 3H), 7.34 (d, J=8.4 Hz, 1H), 7.67 (s, 2H), 7.92 (d, J=8.7 Hz, 1H), 8.48 (s, 1H), 8.79 (s, 1H), 9.69 (s, 2H), 10.78 (s, 1H)

IR (KBr): (cm$^{-1}$) 3318, 3175, 2960, 1688, 1293, 1102

EXAMPLE 17

N-(3,5-dichloropyrid-4-yl)-4-methoxy-8-phenoxycarboxamido-dibenzo[b,d]furan-1-carboxamide

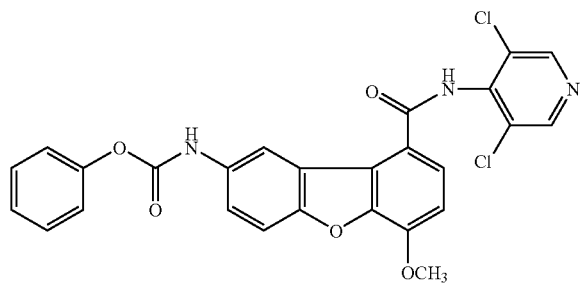

$^1$H NMR (300 MHz, DMSO-d$_6$) δ 4.09 (s, 3H), δ 7.12 (d, 1H, J=8.4 Hz), δ 7.23–7.47 (m, 5H), δ 7.73 (d, 1H, J=9.0 Hz), δ 7.80 (d, 1H, J=8.7 Hz), δ 8.02 (d, 1H, J=8.7 Hz), δ 8.31 (d, 1H, J=6.4 Hz), δ 8.97 (s, 2H), 610.45 (s, 1H).

IR (KBr)3358, 2918, 1777, 1750, 1610, 1560, 1493, 1391, 1284, 1235, 1192, 1003, 803, 619, cm$^{-1}$

EXAMPLE 18

N-(3,5-dichloropyrid-4-yl)-4-methoxy-8-cyclopropylmethoxycarboxamido-dibenzo[b,d]furan-1-carboxamide

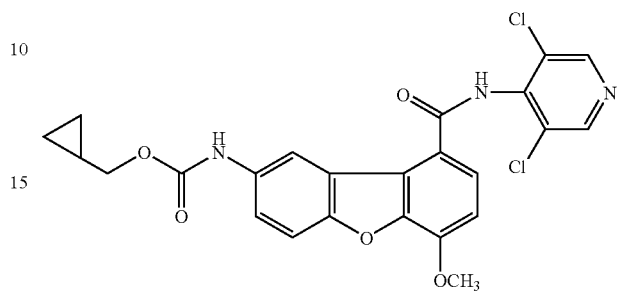

A solution of cyclopropyl methanol (70 mg, 0.273 mmol) in THF (3 ml) was cooled to −30C. To this solution was added triethylamine (37 mg, 0.374 mmol) and stirred for 10 min. A solution of triphosgene (73 mg, 0.249 mmol) in THF (3 ml) was added at −30° C. to the above solution and stirred for 30 min at room temperature. This solution was then added to a suspension of N-(3,5-dichloropyrid-4-yl)-4-methoxy-8-amino-dibenzo[b,d]furan-1-carboxamide (100 mg, 0.249 mmol) (intermediate 1) and triethylamine (37 mg, 0.374 mmol) in THF (5 ml). The reaction was stirred at room temperature for 30 min. THF was evaporated and the residue was washed with water. The solid obtained was purified by silica gel column chromatography using 10% acetone-chloroform as eluent to obtain 15 mg of N-(3,5-dichloropyrid-4-yl)-4-methoxy-8-cyclopropylmethoxycarboxamido-dibenzo[b,d]furan-1-carboxamide as white solid; mp: 272° C.

$^1$H NMR (300 MHz, DMSO-d$_6$) δ 0.29(q, 2H, J=6.0 Hz), δ 0.52 (q, 2H, J=6.3Hz), δ 1.14 (m, 1H), δ 3.88 (d, 2H, J=7.2 Hz), δ 4.06 (s, 3H), δ 7.32(d, 1H, J=8.1Hz), δ7.60 (d, 1H, J=8.4 Hz), δ 7.66 (d, 1H, J=8.7 Hz), δ 7.90 (ds, 1H, J=8.1 Hz), δ 8.48 (d, 1H, J=2.4), δ 8.76 (s, 2H), δ 9.69 (s, 1H), δ 10.75 (s, 1H).

IR (KBr) 2960, 2735, 1672, 1596, 1473, 1461, 1323, 1271, 1180, 1113, 1089, 1001, 945, 817, 767, cm$^{-1}$

EXAMPLE 19

N-(3,5-dichloropyrid-4-yl)-4-methoxy-8-trifuoromethylmethoxycarboxamido-dibenzo[b,d]furan-1-carboxamide

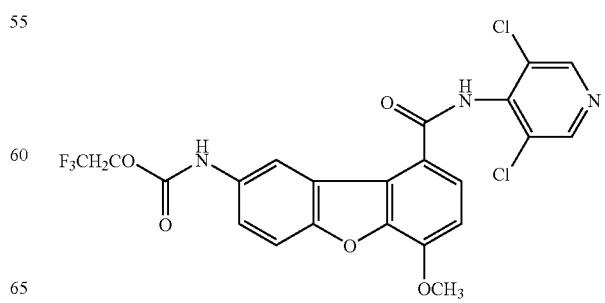

Was synthesized using reaction conditions similar to Example 17 except for using the 2, 2, 2-trifluoroethanol instead of cyclopropylmethanol.mp: >250° C.

¹H NMR (300 MHz, DMSO-d₆) δ 4.07 (s, 3H), 4.77 (q, 2H, J=9.0 Hz), 7.35 (d,1H, J=8.4 Hz), 7.63 (d, 1H, J=9.3 Hz), 7.72 (d, 1H, J=9.0 Hz), 7.93 (d, 1H, J=8.4 Hz), 8.52 (s, 1H), 8.76 (s, 2H), 10.18 (brs, 1H), 10.76 (s, 1H).

IR (KBr) 3342, 2921, 1670, 1640, 1547, 1482, 1389, 1284, 1256, 1184, 954, 810, 758, cm⁻¹

EXAMPLE 20

N-(3,5-dichloropyrid-4-yl)-4-methoxy-8-N,N-diethylaminocarboxamido-dibenzo[b,d]furan-1-carboxamide

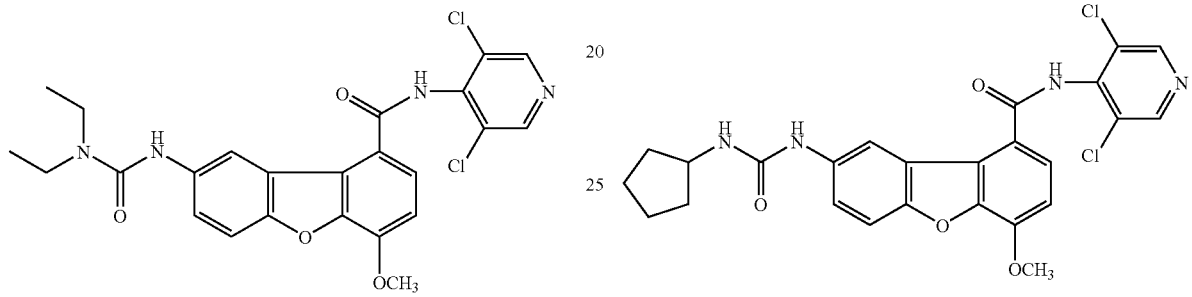

Step 1. N-(3,5-dichloropyrid-4-yl)-4-methoxy-8-phenoxycarboxamido-dibenzo[b,d]furan-1-carboxamide N-(3,5-dichloropyrid-4-yl)-4-methoxy-8-amino-dibenzo[b,d]furan-1-carboxamide (400 mg, 0.99 mmol) (intermediate 1) was treated with phenyl chloroformate (190 mg, 1.09 mmol) in THF (15 ml) containing pyridine (0.5 ml) at 0° C. and allowed to warm to room temperature. The reaction was stirred at room temperature for 12 h. THF was evaporated and the residue was washed with water and hot ethanol to obtain 400 mg of N-(3,5-dichloropyrid-4-yl)-4-methoxy-8-phenoxycarboxamido-dibenzo[b,d]furan-1-carboxamide as white solid which was used as such in the next step.

Step 2. N-(3,5-dichloropyrid-4-yl)-4-methoxy-8-N,N-diethylaminocarboxamido-dibenzo[b, d]furan-1-carboxamide N-(3,5-dichloropyrid-4-yl)-4-methoxy-8-phenoxycarboxamido-dibenzo[b,d]furan-1-carboxamide (from step 1) (100 mg, 0.19 mmol), was dissolved in DMSO (2.0 ml) and a solution of N,N-diethylamine (20 mg, 0.28 mmol) in DMSO (1.0 ml) was added slowly to the above solution. The reaction mixture was stirred at 50° C. for 5 h, cooled to room temperature and diluted with ice water (25 ml). The solid that separated as a result was filtered, dried and purified by silica gel column chromatography using 10% methanol in chloroform as eluent to obtain 45 mg of N-(3,5-dichloropyrid-4-yl)-4-methoxy-8-N,N-diethylaminocarboxamido-dibenzo[b,d]furan-1-carboxamide as white solid; mp: >250° C.

¹H NMR (300 MHz, DMSO-d₆) δ 1.08 (t, 6H, J=7.2 Hz), δ 3.25 (q, 4H, J=5.1Hz), δ 4.06 (s, 3H), δ 7.31(d, 1H, J=8.4 Hz), δ 7.59 (s, 2H), δ 7.90 (d, 1H, J=8.4 Hz), δ 8.32 (s, 1H), δ 8.75 (s, 2H), δ 10.74 (s, 1H).

IR (KBr) 3357, 2932, 1673, 1631, 1552, 1474, 1396, 1285, 1198, 1101, 952, 805, 670, cm−1

Example 21, 22, 24, 25, 26, 27, 28 and 29 were synthesized using reaction conditions similar to step 2 of Example 21 except for using the appropriate primary or secondary amine instead of N,N-diethylamine.

EXAMPLE 21

N-(3,5-dichloropyrid-4-yl)-4-methoxy-8-cyclopentylaminocarboxamido-dibenzo[b,d]furan-1-carboxamide

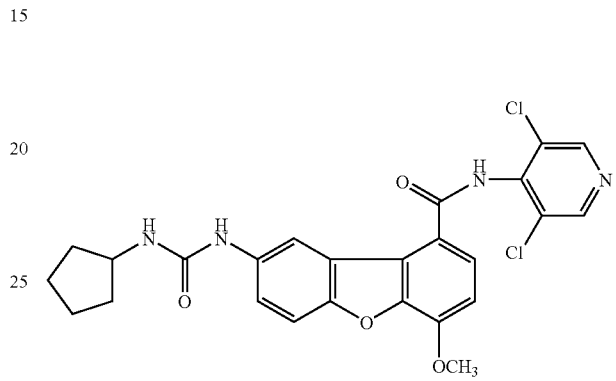

¹H NMR (300 MHz, DMSO) δ 1.355 (m, 2H), 1.57 (m, 4H), 1.81(m, 2H) 3.94 (m, 1H), 4.07 (s, 3H), 6.03 (d, 1H), 7.34 (d, 1H), 7.63 (d, 1H), 7.96 (m, 2H), 8.11 (1H), 8.43 (s, 1H), 8.79 (s, 2H), 10.8 (s, 1H)

IR (KBr): 3311, 3142, 2957, 1658, 1633, 1564, 1491, 1477, 1295, 1223, 1198, 1101, 1025, 806 cm⁻¹.

Mass: (M+H)=513.3

EXAMPLE 22

N-(3,5-dichloropyrid-4-yl)-4-methoxy-8-(N-methylpiperazin-4-yl carboxamido)-dibenzo[b,d]furan-1-carboxamide

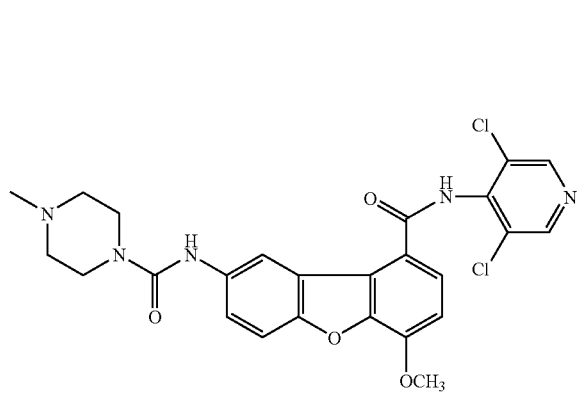

¹H NMR (300 MHz, DMSO-d₆) δ 2.23 (s, 3H), 2.50 (brm, 4H), 3.43 (brm, 4H), 4.08 (s, 3H), 7.34 (d, 1H, J=8.7 Hz), 7.63 (s, 2H), 7.95 (d, 1H, J=8.4 Hz), 8.35 (s, 1H), 8.68 (s, 1H), 8.78 (s, 2H), 10.77 (s, 1H).

IR (KBr) 3358, 2919, 1667, 1635, 1556, 1593, 1479, 1397, 1285, 1241, 1106, 1002, 802, 619, cm⁻¹

EXAMPLE 23

N-(3,5-dichloropyrid-4-yl)-4-methoxy-8-(N-methylpiperazin-4-yl carboxamido)-dibenzo[b,d]furan-1-carboxamide hydrochloride

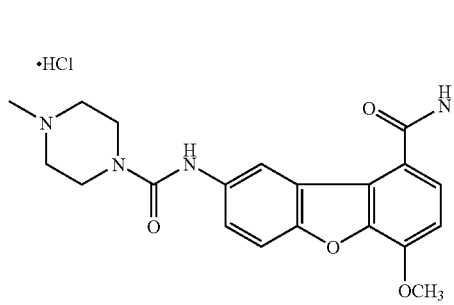

Was synthesized from N-(3,5-dichloropyrid-4-yl)-4-methoxy-8-(N-methylpiperazin-4-yl carboxamido-dibenzo[b,d]furan-1-carboxamide using methanolic HCl.mp: >250° C.

$^1$H NMR (300 MHz, DMSO-d$_6$) δ 2.77 (d, 3H, J=4.2 Hz), 3.02 (m, 2H), 3.24–3.43 (brm, 4H), 4.08 (s, 3H), 4.23 (m, 2H), 7.34 (d, 1H, J=8.7 Hz), 7.63 (s, 2H), 7.89 (d, 1H, J=8.4 Hz), 8.37 (s, 1H), 9.03 (s, 1H), 10.63 (s, 2H), 11.23 (s, 1H).

EXAMPLE 24

N-(3,5-dichloropyrid-4-yl)-4-methoxy-8-(4-hydroxypiperidin-1-yl carboxamido)-dibenzo[b,d]furan-1-carboxamide

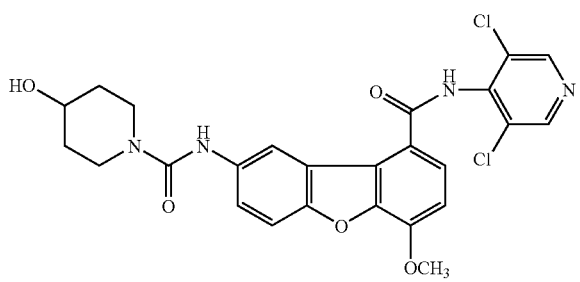

$^1$H NMR (300 MHz, DMSO-d$_6$) δ 1.30 (m, 2H), 1.73 (m, 2H), 3.02 (m, 2H), 3.64 (m, 1H), 3.64 (m, 2H), 4.08 (s, 3H), 4.75 (brs, 1H), 7.34 (d, 1H, J=8.7 Hz), 7.63 (s, 2H), 7.94 (d, 1H, J=8.4 Hz), 8.35 (s, 1H), 8.64 (s, 1H), 8.78 (s, 2H), 10.77 (s, 1H).

IR (KBr) 3349, 2912, 1662, 1636, 1561, 1596, 1480, 1391, 1285, 1244, 1113, 1005, 811, 621 cm$^{-1}$

EXAMPLE 25

N-(3,5-dichloropyrid-4-yl)-4-methoxy-8-(morphol-4-yl carboxamido)-dibenzo[b,d]furan-1-carboxamide

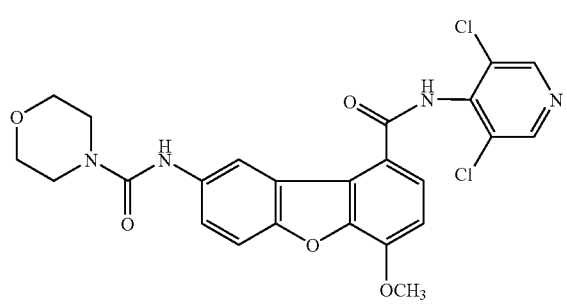

$^1$H NMR (300 MHz, DMSO-d$_6$) δ 3.40 (t, 4H, J=5.1 Hz), δ 3.58 (t, 4H, J=5.1Hz), δ 4.06 (s, 3H), δ 7.32 (d, 1H, J=8.4 Hz), δ 7.61 (s, 2H), δ 7.93 (d, 1H, J=8.4 Hz), δ 8.33 (s, 1H), δ 8.66 (s, 1H), δ 8.75 (s, 2H), δ 10.75 (s, 1H).

IR (KBr)3345, 2911, 2782, 1665, 1642, 1551, 1479, 1397, 1278, 1251, 1187, 1026, 945, 810, 761, cm$^{-1}$.

EXAMPLE 26

N-(3,5-dichloropyrid-4-yl)-4-methoxy-8-isopropylamino carboxamido-dibenzo[b,d]furan-1-carboxamide

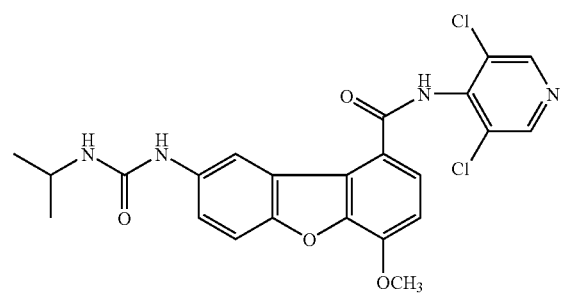

$^1$H NMR (300 MHz, DMSO-d$_6$) δ 1.08 (d, 3H, J=6.6 Hz), 1.23 (m, 1H), 1.31 (d, 2H, J=6.6 Hz), 4.07 (s, 3H), 7.33 (d, 1H, J=8.7 Hz), 7.38 (d, 1H, J=7.8 Hz), 7.66 (d, 1H, J=9.3 Hz), 7.72 (dd, 1H, J=9.3 Hz and J=2.1 Hz), 7.91 (d, 1H, J=8.4 Hz), 8.39 (d, 1H, J=2.1 Hz), 8.75 (s, 2H), 9.68 (s, 1H), 10.77 (s, 1H).

IR (KBr) 3354, 2927, 1668, 1638, 1552, 1491, 1396, 1280, 1251, 1196, 951, 802, 761, cm$^{-1}$

EXAMPLE 27

N-(3,5-dichloropyrid-4-yl)-4-methoxy-8-n-hexy-lamino carboxamido-dibenzo[b,d]furan-1-carboxamide

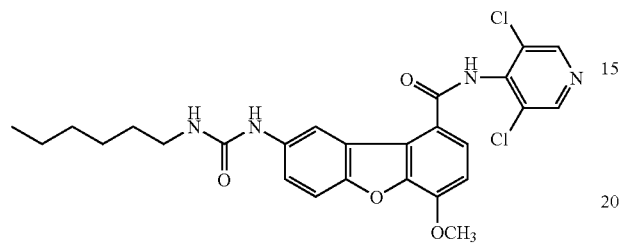

$^1$H NMR (300 MHz, DMSO-d$_6$) δ 0.85 (t, 3H), 1.23 (m, 8H), 3.1 (q, 2H), 4.06 (s, 1H), 5.96 (t, 1H), 7.30 (d, 1H, J=8.7 Hz), 7.60 (d, 1H, J=9.0 Hz), 7.90 (m, 2H), 8.10 (s, 1H), 8.53 (s, 1H), 8.75 (s, 2H), 10.76 (s, 1H).

IR (KBr) 3360, 2938, 1667, 1634, 1582, 1478, 1398, 1284, 1241, 1196, 953, 803, 671, cm$^{-1}$

EXAMPLE 28

N-(3,5-dichloropyrid-4-yl)-4-methoxy-8-ethylamino carboxamido-dibenzo[b,d]furan-1-carboxamide

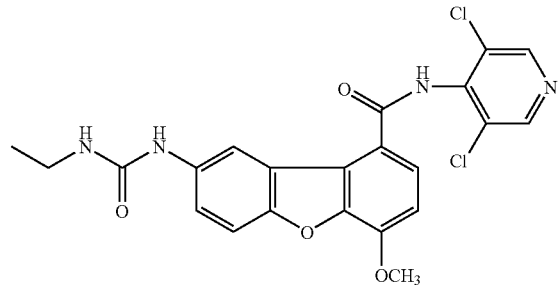

$^1$H NMR (300 MHz, DMSO-d$_6$) δ: 1.03 (t, J=7.2 Hz, 3H), 3.07–3.12 (q, 2H), 4.07 (s, 3H), 5.96 (t, J=6 Hz, 1H), 7.33 (d, J=8.7 Hz, 1H), 7.62 (d, J=9 Hz, 1H), 7.92 (dd, J=3.3 Hz, 8.7 Hz, 2H), 8.14 (d, J=2.1 Hz, 1H), 8.59 (s, 1H), 8.79 (s, 1H), 10.81 (s, 2H)

IR (KBr): 3322, 3146, 1657, 1637, 1294, 1101, cm$^{-1}$

EXAMPLE 29

N-(3,5-dichloropyrid-4-yl)-4-methoxy-8-methylamino carboxamido-dibenzo[b,d]furan-1-carboxamide

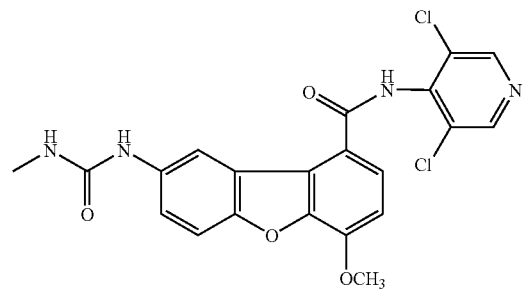

$^1$H NMR (300 MHz, DMSO-d$_6$) δ: 2.63 (d, J=4.8 Hz, 3H), 4.07 (s, 3H), 5.86–5.89 (m, 1H), 7.33 (d, J=8.7 Hz, 1H), 7.62 (d, J=9 Hz, 1H), 7.92 (d, J=8.7 Hz, 2H), 8.16 (d, J=1.8 Hz, 1H), 8.66 (s, 1H), 8.79 (s, 1H), 10.81 (s, 2H)

IR (KBr): 3337, 3149, 1659, 1637, 1295, 1098, cm$^{-1}$

EXAMPLE 30

N-(3,5-dichloropyrid-4-yl)-4-difluoromethoxy-8-methanesulfonamido-dibenzo[b,d]furan-1-carboxamide

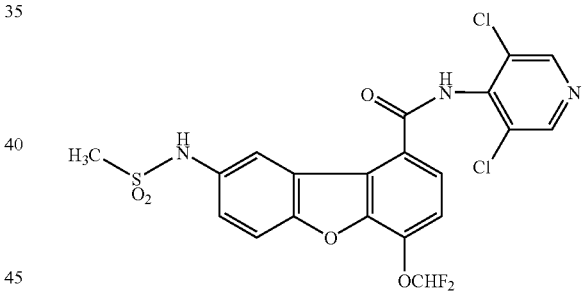

N-(3,5-dichloropyrid-4-yl)-4-difluoromethoxy-8-amino-dibenzo[b,d]furan-1-carboxamide (70 mg, 0.159 mmol) (intermediate 2) was treated with methanesulfonyl chloride (22 mg, 0.194 mol) in THF (10 ml) containing pyridine (0.5 ml) at 0° C. and allowed to warm to room temperature. The reaction was stirred at room temperature for 2 h. THF was evaporated and the residue was washed with saturated sodium bicarbonate solution, water. The solid obtained was purified by silica gel column chromatography using 12% acetone-chloroform as eluent to obtain 37 mg of N-(3,5-dichloropyrid-4-yl)-4-difluoromethoxy-8-methanesulfonylamido-dibenzo[b,d]furan-1-carboxamide as white solid; mp: >250° C.

$^1$H NMR (300 MHz, DMSO-d$_6$) δ 2.95 (s, 3H), 7.5 (dd, 1H, J=8.7 Hz and J=2.4 Hz), 7.58 (t, 1H, J=72 Hz), 7.6 (d, 1H, J=8.4 Hz), 7.85 (d, 1H, J=9.3 Hz), 7.93 (d, 1H, J=8.1 Hz), 8.30 (d, 1H, J=2.4 Hz), 8.82 (s, 2H), 9.77 (s, 1H), 11.06 (s, 1H).

IR (KBr) 3323, 2926, 1698, 1636, 1489, 1396, 1283, 1266, 1142, 1040, 812, 621, cm$^{-1}$

EXAMPLE 30a

N-(3,5-dichloropyrid-4-yl)-4-difluoromethoxy-8-methanesulfonamido-dibenzo[b,d]furan-1-carboxamide N-oxide

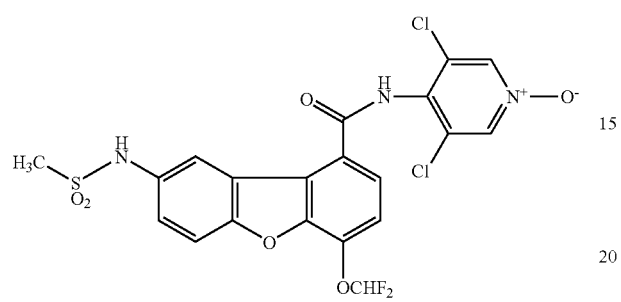

N-(3,5-dichloropyrid-4-yl)-4-difluoromethoxy-8-methansulfonamido-dibenzo[b, d]furan-1-carboxamide N-oxide (Example 30a) was prepared by the procedure described in Example 47, except the starting material used was N-(3,5-dichloropyrid-4-yl)-4-difluoromethyxy-8-methanesulfonamido-dibenzo[b,d]furan-1-carboxamide (Example 30) instead of N-(3,5-dichloropyrid-4-yl)-4-methoxy-8-acetamido-dibenzo[b,d]furan-1-carboxamide (Example 4). $^1$H NMR (300 Mhz, DMSO-$d_6$) δ: 2.94 (s, 3H), 7.51 (d, 1H), 7.58 (t, 1H J=72 Hz), 7.62 (d, 1H), 7.85 (d, 1H), 7.90 (d, 1H), 8.28 (s, 1H), 8.79(s, 2H), 9.79 (s, 1H), 10.89(s, 1H).

EXAMPLE 31

N-(3,5-dichloropyrid-4-yl)-4-difluoromethoxy-8-methanesulfonamido-dibenzo[b,d]furan-1-carboxamide sodium salt

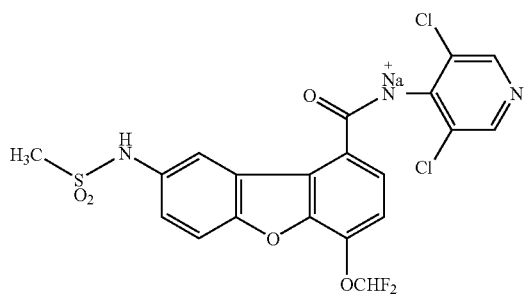

Was synthesized from N-(3,5-dichloropyrid-4-yl)-4-difluoromethoxy-8-methanesulfonamido-dibenzo[b,d]furan-1-carboxamide (Example 30) using 1% methanolic sodium hydroxide (1.0 eq.).

$^1$H NMR (300 MHz, DMSO-$d_6$) δ 2.95 (s, 3H), 7.26 (d, 2H, J=8.7 Hz), 7.40 (t, 1H, J=72 Hz), 7.52 (d, 1H, J=8.4 Hz), 7.95 (d, 1H, J=9.3 Hz), 8.19 (s, 2H), 8.68 (brs, 1H), 9.66 (brs, 1H).

IR (KBr) 2920, 1651, 1524, 1463, 1391, 1278, 1194, 1105, 1005, 882, 815 cm$^{-1}$

Example 32 and 33 were synthesized using reaction conditions similar to Example 30 except for using the appropriate substituted sulfonyl chloride instead of methane sulfonyl chloride.

EXAMPLE 32

N-(3,5-dichloropyrid-4-yl)-4-difluoromethoxy-8-ethanesulfonamido-dibenzo[b,d]furan-1-carboxamide

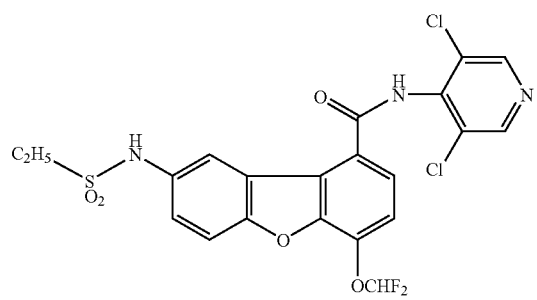

$^1$H NMR (300 MHz, DMSO-$d_6$) δ 1.19 (t, 3H, J=7.2 Hz), 3.03 (q, 2H, J=7.2 Hz), 7.49 (dd, 1H, J=8.7 Hz and J=2.1 Hz), 7.58 (t, 1H, J=73 Hz), 7.81 (d, 1H, J=8.4 Hz), 7.93 (d, 1H, J=8.7 Hz), 8.29 (d, 1H, J=2.4 Hz) 8.82 (s, 2H), 9.85 (s, 1H), 11.06 (s, 1H).

IR (KBr): 3264, 2988, 1672, 1590, 1562, 1472, 1256, 1192, 1134, 1028, 973, 733 cm$^{-1}$

EXAMPLE 33

N-(3,5-dichloropyrid-4-yl)-4-difluoromethoxy-8-N,N-dimethylaminosulfonamido-dibenzo[b,d]furan-1-carboxamide

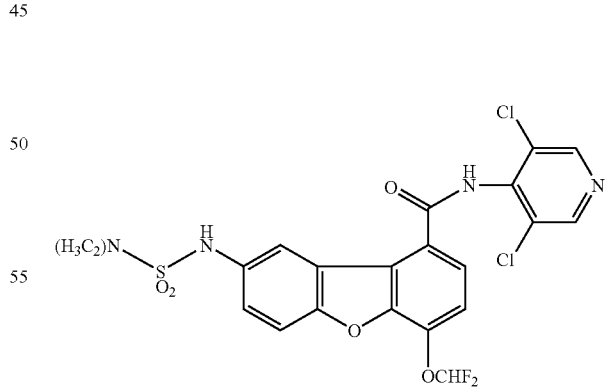

$^1$H NMR (300 MHz, DMSO-$d_6$) δ 2.7 (s, 6H), 7.49 (dd, 1H, J=8.7 Hz and J=2.1 Hz), 7.57 (t, 1H, J=73 Hz), 7.59 (d, 1H, J=8.4 Hz), 7.81 (d, 1H, J=8.7 Hz), 7.92 (d, 1H, J=8.4 Hz), 8.28 (s, 2H), 9.93 (s, 1H), 11.05(s, 1H).

IR (KBr) 3274, 3012, 1660, 1602, 1579, 1483, 1279, 1200, 1121, 1009, 823, 623 cm$^{-1}$

EXAMPLE 34

N-(3,5-dichloropyrid-4-yl)-4-difluoromethoxy-8-acetamido-dibenzo[b,d]furan-1-carboxamide

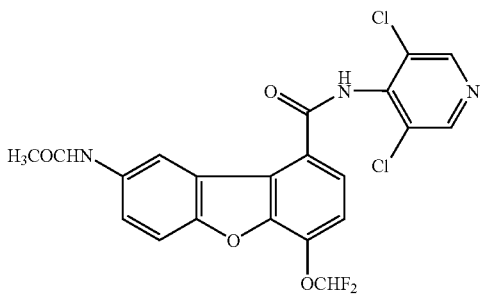

N-(3,5-dichloropyrid-4-yl)-4-difluoromethoxy-8-amino-dibenzo[b,d]furan-1-carboxamide (70 mg, 0.159 mmol) (intermediate 2) was treated with acetyl chloride (22 mg, 0.299 mmol) in THF (10 ml) containing pyridine (0.5 ml) at 0° C. and allowed to warm to room temperature. The reaction was stirred at room temperature for 2.0 h. THF was evaporated and the residue was washed with saturated sodium bicarbonate solution 5% HCl and water. The solid obtained was purified by silica gel column chromatography using 10% acetone-chloroform as eluent to obtain 25 mg of N-(3,5-dichloropyrid-4-yl)-4-difluoromethoxy-8-acetamido-dibenzo[b,d]furan-1-carboxamide as white solid; mp: 234° C.

$^1$H NMR (300 MHz, DMSO-$d_6$) δ 2.15 (s, 3H), 7.4 (d, 1H, J=8.4 Hz), 7.53 (t, 1H, J=73 Hz), 7.56 (d, 1H, J=8.4 Hz), 7.77–7.86 (m, 3H), 8.36 (d, 1H, J=2.4 Hz), 8.81 (s, 2H), 10.25 (s, 1H).

IR (KBr) 3344, 2924, 1727, 1712, 1686, 1555, 1390, 1367, 1288, 1269, 1116, 1047, 822, 584 cm$^{-1}$

Example 35, 36, 37, and 40 were synthesized using reaction conditions similar to Example 34 except for using the appropriate substituted acid chloride instead of acetyl chloride

EXAMPLE 35

N-(3,5-dichloropyrid-4-yl)-4-difluoromethoxy-8-(1-chloropropylcarboxamido)-dibenzo[b,d]furan-1-carboxamide

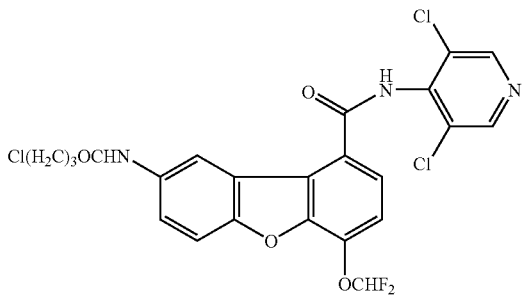

$^1$H NMR (300 MHz, DMSO-$d_6$) δ 2.12 (m, 2H), 2.61 (t, 2H, J=7.2 Hz), 3.75 (t, 2H, J=6.9 Hz), 7.61 (d, 1H, J=7.8 Hz), 7.63 (t, 1H, J=73 Hz), 7.79 (d, 1H, J=8.7 Hz), 8.07 (d, 1H, J=8.4 Hz), 8.18 (dd, 1H, J=9.3 Hz and J=2.4 Hz), 8.65 (d, 1H, J=2.2 Hz) 8.82 (s, 2H), 10.35 (s, 1H).

IR (KBr) 3281, 3156, 2987, 1664, 1650, 1526, 1496, 1381, 1284, 1217, 1146, 1110, 814, 677 cm$^{-1}$.

EXAMPLE 36

N-(3,5-dichloropyrid-4-yl)-4-difluoromethoxy-8-cyclopropylcarboxamido-dibenzo[b,d]furan-1-carboxamide

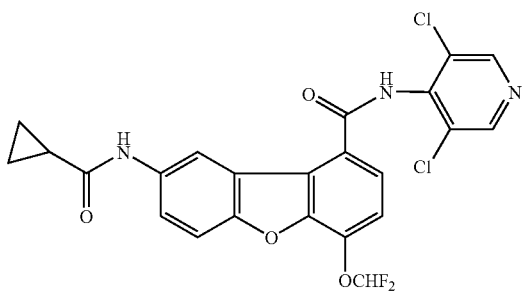

$^1$H NMR (300 MHz, DMSO-$d_6$) δ 0.78 (m, 2H), 1.23 (m, 2H), 1.80 (m, 1H), 7.60 (d, 1H, J=8.4 Hz), 7.58 (t, 1H, J=73 Hz), 7.76 (d, 1H, J=8.4 Hz), 7.94 (d, 1H, J=8.4 Hz), 8.02 (d, 1H, J=8.4 Hz), 8.44 (s, 1H), 8.81 (s, 2H), 10.40 (s, 1H), 11.02 (s, 1H).

IR (KBr) 3289, 3143, 1660, 1650, 1528, 1494, 1400, 1279, 1195, 1150, 1106, 1056, 819 cm$^{-1}$.

EXAMPLE 37

N-(3,5-dichloropyrid-4-yl)-4-difluoromethoxy-8-ethoxycarbonylcarboxamido-dibenzo[b,d]furan-1-carboxamide

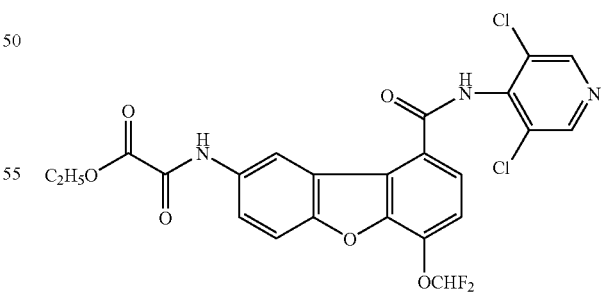

$^1$H NMR (300 MHz, DMSO-$d_6$) δ 1.33 (t, 3H), 4.32 (q, 2H), 7.57 (t, 1H, J=72 Hz), 7.62 (d, 1H, J=8.7 Hz), 7.84 (d, 1H, J=8.7 Hz), 7.86–7.96 (m, 2H), 8.69 (d, 1H, J=1.8 Hz) 8.81 (s, 2H) 11.04 (s, 2H).

IR (KBr) 3206, 3107, 2987, 1759, 1702, 1669, 1548, 1499, 1384, 1296, 1279, 1222, 1191, 1118, 1055, 810 cm$^{-1}$.

EXAMPLE 38

N-(3,5-dichloropyrid-4-yl)-4-difluoromethoxy-8-hydroxycarbonylcarboxamido-dibenzo[b,d]furan-1-carboxamide

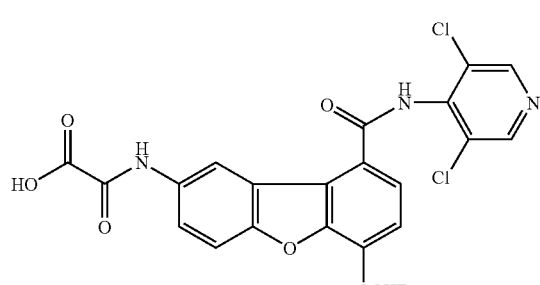

Was synthesized by hydrolysis of N-(3,5-dichloropyrid-4-yl)-4-difluoromethoxy-8-ethoxycarbonylcarboxamido-dibenzo[b,d]furan-1-carboxamide (Example 37) using potassium hydroxide (3 eq.) in methanol.

$^1$H NMR (300 MHz, DMSO-$d_6$) δ 7.58 (t, 1H, J=72 Hz), 7.62 (d, 1H, J=8.4 Hz), 7.86 (d, 1H, J=8.7 Hz), 7.91–7.96 (m, 2H), 8.76 (d, 1H, J=1.8 Hz) 8.81 (s, 2H,) 10.97 (s, 1H), 11.04 (s, 1H).

EXAMPLE 39

N-(3,5-dichloropyrid-4-yl)-4-difluoromethoxy-8-hydroxycarbonylcarboxamido-dibenzo[b,d]furan-1-carboxamide disodium salt

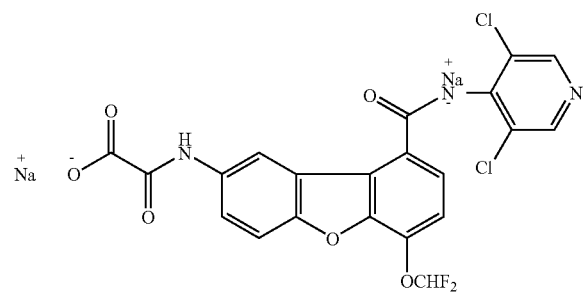

Was synthesized from N-(3,5-dichloropyrid-4-yl)-4-difluoromethoxy-8-hydroxycarbonylcarboxamido-dibenzo[b,d]furan-1-carboxamide (Example 38) using ethanolic sodium ethoxide (2.0 eq.).

$^1$H nmr (300 MHz, DMSO-$d_6$) δ 7.30 (d, 1H, J=8.7 Hz), 7.42 (t, 1H, J=72 Hz), 7.65 (d, 1H, J=8.7 Hz), 7.98 (d, 1H, J=8.7 Hz), 8.06 (dd, 1H, J=9.0 and 1.8 Hz) 8.21 (s, 2H) 9.08 (d, 1H, J=2.4 Hz), 10.08 (s, 1H).

EXAMPLE 40

N-(3,5-dichloropyrid-4-yl)-4-difluoromethoxy-8-fur-2-ylcarboxamido-dibenzo[b,d]furan-1-carboxamide

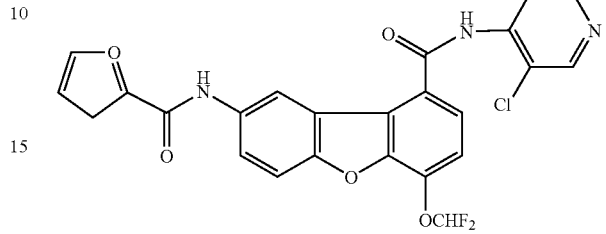

$^1$H NMR (300 MHz, DMSO-$d_6$) δ 6.68 (d, 1H, J=3.3 Hz), 7.35 (d, 1H, J=3.3 Hz), 7.59 (t, 1H, J=72 Hz), 7.62 (d, 1H, J=8.4 Hz), 7.82 (d, 1H, J=9.0 Hz), 7.93–7.99 (m, 3H), 8.66 (s, 1H, J=1.8 Hz), 8.81 (s, 2H). 10.44 (s, 1H), 11.04 (s, 1H)

IR (KBr)3288, 3031, 1651, 1586, 1556, 1518, 1498, 1386, 1281, 1193, 1117, 1046, 809, 750 cm$^{-1}$.

EXAMPLE 41

N1-phenyl-4-methoxy-8-acetamido-dibenzo[b,d]furan-1-carboxamide

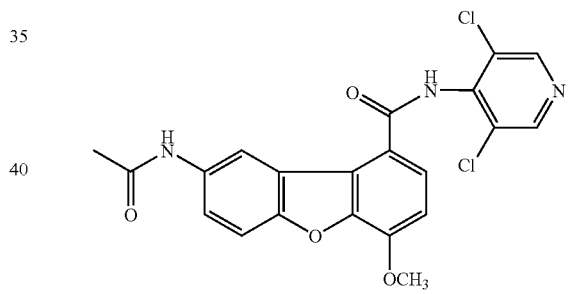

Step 1: N1-phenyl-4-methoxy-8-nitro-dibenzo[b,d]furan-1-carboxamide 4-methoxy-8-nitro dibenzo[b,d]furan-1-carboxylic acid chloride (200 mg, 0.696 mmol) (from step 5a of intermediate 1) was reacted with aniline (2.0 eq.) in THF (10 ml) in the presence of diisopropylethylamine (3 eq.) at room temperature for 16 h. The yellow suspension was filtered and the solid obtained was washed with 5% HCl and water to obtain 110 mg of N1-phenyl-4-methoxy-8-nitro-dibenzo[b,d]furan-1-carboxamide as white solid.

$^1$H NMR (300 MHz, DMSO-$d_6$) δ 4.15 (s, 3H), 7.18 (t, 1H), 7.43 (m, 3H), 7.80 (d, 2H), 7.95 (d, 1H), 8.01 (d, 1H), 8.45 (d, 1H), 9.40 (s, 1H), 10.60 (s, 1H).

Step 2: N1-phenyl-4-methoxy-8-amino-dibenzo[b,d]furan-1-carboxamide

N1-phenyl-4-methoxy-8-nitro-dibenzo[b,d]furan-1-carboxamide (100 mg) (from step1) was reduced using raney nickel (100 mg) in methanol (40 ml) and DMF (10 ml) in the presence of hydrazine hydrate (0.5 ml) under gentle reflux for 1 h. The reaction mixture was fliterd through celite and the filterate was concentrated in vaccuo. The residue was triturated with water, to obtain a solid which was filtered dried to give the product as white solid (90 mg).

$^1$H NMR (300 MHz, DMSO-$d_6$) δ 4.15 (s, 3H), 5.03 (brs, 2H), 6.80 (d, 1H), 7.08 (t, 1H), 7.11 (d, 1H), 7.40 (m, 4H), 7.60 (d, 1H), 7.93 (d, 2H), 10.43 (s, 1H).

Step 3: N1-phenyl-4-methoxy-8-acetamido-dibenzo[b,d]furan-1-carboxamide

N1-phenyl-4-methoxy-8-amino-dibenzo[b,d]furan-1-carboxamide (69 mg, 0.207 mmol) (step 2) was treated with acetyl chloride (1.1 eq.) in THF (10 ml) containing pyridine (1.1 eq) at 0° C. and allowed to warm to room temperature. The reaction was stirred at room temperature for 2 h. THF was evaporated and the residue was washed ethanol to obtain 40 mg of N1-phenyl-4-methoxy-8-acetamido-dibenzo[b,d]furan-1-carboxamide as white solid; mp: 252° C.

IR (KBr): 3316, 3237, 2937, 1650, 1531, 1596, 1507, 1472, 1439, 1292, 1195, 187, 1100, 809, 753 cm$^{-1}$.

$^1$H NMR (300 MHz, DMSO) δ 2.03 (s, 3H), 4.05 (s, 3H), 7.14 (t, 1H), 7.28 (d, 1H), 7.39 (t, 2H), 7.66–7.74 (m, 2H), 7.82 (d, 2H), 7.91 (dd, 1H, J=9.0 and 2.7 Hz), 8.37 (d, 1H, J=2.4 Hz), 10.10 (s, 1H), 10.50 (s, 1H).

EXAMPLE 42

N1-(4-methoxyphenyl)-4-methoxy-8-acetamido-dibenzo[b,d]furan-1-carboxamide

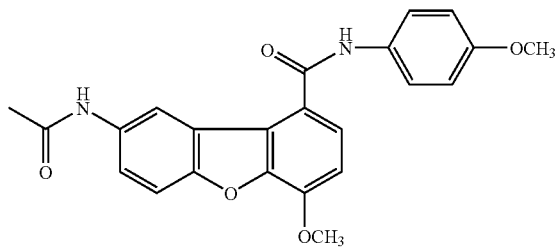

Step 1: N1-(4-methoxyphenyl)-4-methoxy-8-nitro-dibenzo[b,d]furan-1-carboxamide 4-methoxy-8-nitro dibenzo[b,d]furan-1-carboxylic acid chloride (200 mg, 0.696 mmol) (from step 5a of intermediate 1) was reacted with 4-methoxy aniline (2.0 eq.) in THF (10 ml) in the presence of diisopropylethylamine (3 eq.) at room temperature for 16 h. The yellow suspension was filtered and the solid obtained was washed with 5% HCl and water to obtain 153 mg of N1-(4-methoxyphenyl)-4-methoxy-8-nitro-dibenzo[b,d]furan-1-carboxamide as white solid.

$^1$H NMR (300 MHz, DMSO-$d_6$) δ 3.90 (s, 3H), 4.15 (s, 3H), 6.99 (d, 2H), 7.42 (d, 1H), 7.77 (d, 2H), 7.96 (d, 1H), 8.02 (d, 1H), 8.43 (d, 1H), 9.40 (s, 1H), 10.60 (s, 1H).

Step 2: N1-(4-methoxyphenyl)-4-methoxy-8-amino-dibenzo[b,d]furan-1-carboxamide N1-(4-methoxyphenyl)-4-methoxy-8-nitro-dibenzo[b,d]furan-1-carboxamide (140 mg) (from step I) was reduced using raney nickel (100 mg) in methanol (40 ml) and DMF (10 ml) in the presence of hydrazine hydrate (1.0 ml) under gentle reflux for 1 h. The reaction mixture was fliterd through celite and the filterate was concentrated in vaccuo. The residue was triturated with water, to obtain a solid which was filtered dried to give the product as white solid (90 mg).

$^1$H NMR (300 MHz, DMSO-$d_6$) δ 3.88 (s, 3H), 4.05 (s, 3H), 5.03 (brs, 2H), 6.90 (d, 1H), 7.01 (d, 2H), 7.20 (d, 1H), 7.40 (m, 2H), 7.60 (d, 1H), 7.88 (d, 2H), 10.43 (s, 1H).

Step 3: 1-(4-methoxyphenyl)-4-methoxy-8-acetamido-dibenzo[b,d]furan-1-carboxamide N1-(4-methoxyphenyl)-4-methoxy-8-amino-dibenzo[b,d]furan-1-carboxamide (90 mg, 0.248 mmol) (step 2) was treated with acetyl chloride (1.1 eq.) in THF (10 ml) containing pyridine (1.1 eq) at 0° C. and allowed to warm to room temperature. The reaction was stirred at room temperature for 16 h. THF was evaporated and the residue was washed ethanol to obtain 40 mg of N1-(4-methoxyphenyl)-4-methoxy-8-acetamido-dibenzo[b,d]furan-1-carboxamide as white solid; mp: 285° C.

$^1$H NMR (300 MHz, DMSO-$d_6$) δ 2.03 (s, 3H), 3.77 (s, 3H), 4.05 (s, 3H), 6.96 (d, 2H), 7.27 (d, 1H), 7.65–7.74 (m, 4H), 7.91 (dd, 1H, J=9.0 and 2.7 Hz), 8.37 (d, 1h, J=2.4 Hz), 10.10 (s, 1H), 10.36 (s, 1H).

IR (KBr) 3256, 2938, 2839, 1645, 1599, 1531, 1514, 1469, 1412, 1291, 1195, 1178, 1099, 1023, 825, 812 cm$^{-1}$.

EXAMPLE 43

N1-benzyl-4-methoxy-8-acetamido-dibenzo[b,d]furan-1-carboxamide

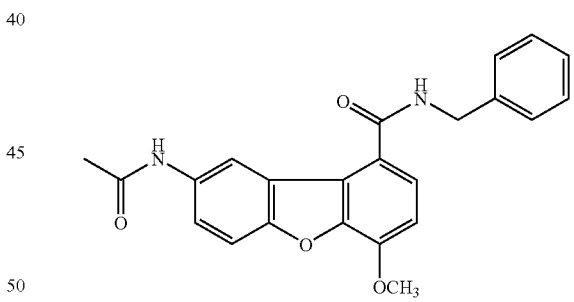

Step 1: N1-benzyl-4-methoxy-8-nitro-dibenzo[b,d]furan-1-carboxamide 4-methoxy-8-nitro dibenzo[b,d]furan-1-carboxylic acid chloride (200 mg, 0.696 mmol) (from step 5a of intermediate 1) was reacted with benzylamine (2.0 eq.) in THF (10 ml) in the presence of diisopropylethylamine (3.0 eq.) at room temperature for 16 h. The suspension was filtered and the solid obtained was washed with 5% HCl and water to obtain 170 mg of N1-benzyl-4-methoxy-8-nitro-dibenzo[b,d]furan-1-carboxamide as white solid.

$^1$H NMR (300 MHz, DMSO-$d_6$) δ 4.08 (s, 3H), 4.62 (d, 2H), 7.15 (d, 1H), 7.18–7.23 (m, 5H), 7.84 (d, 1H), 8.01 (d, 1H), 8.42 (dd, J=8.4 and 2.4 Hz), 9.14 (brt, 1H), 9.58 (d, 1H, J=2.4 Hz)

Step 2: N1-benzyl-4-methoxy-8-amino-dibenzo[b,d]furan-1-carboxamide

N1-benzyl-4-methoxy-8-nitro-dibenzo[b,d]furan-1-carboxamide (125 mg, 0.33 mmol) (from step1) and iron powder (56 mg, 1.0 mmol) was suspended in 50% aqueous ethanol (10 ml) and reflux for 10 min. To this was added a solution of concentrated HCl (7 ul in 5 ml 50% aqueous ethanol) and refluxed for 4 h. The reaction mixture was flitered hot through celite and the filterate was basified with 15% ethanolic KOH, filtered and the filterate was concentrated in vaccuo. The residue was triturated with water, to obtain a solid which-was filtered dried to give the product as white solid (90 mg) mp: 228° C.

$^1$H NMR (300 MHz, DMSO-$d_6$) δ 3.99 (s, 3H), 4.57 (d, 2H), 4.97 (brs, 2H), 6.80 (dd, 1H), 7.12 (d, 1H), 7.29 (d, 1H), 7.34–7.42 (m, 5H), 7.51–7.59 (m, 2H), 9.01 (t, 1H).

Step 3: N1-benzyl-4-methoxy-8-acetamido-dibenzo[b,d]furan-1-carboxamide

N1-benzyl-4-methoxy-8-amino-dibenzo[b,d]furan-1-carboxamide (80 mg, 0.23 mmol) (step 2) was treated with acetyl chloride (1.1 eq.) in THF (10 ml) containing pyridine (1.0 eq) at 0° C. and allowed to warm to room temperature. The reaction was stirred at room temperature for 2 h. The reaction mixture was filterd and the filterarte was concentrated. The residue was triturated with ethanol to obtain 63 mg of N1-benzyl-4-methoxy-8-acetamido-dibenzo[b,d]furan-1-carboxamide as white solid; mp: 264–265° C.

$^1$H NMR (300 MHz, DMSO-$d_6$) δ 2.07 (s, 3H), 4.03 (s, 3H), 4.58 (d, 2H), 7.21–7.27 (m, 2H), 7.33–7.43 (m, 4H), 7.64 (d, 2H), 7.87 (dd, 1H, J=8.7 and 2.7 Hz), 8.54 (d, 1H, J=2.7 Hz), 9.09 (t, 1H), 10.14 (s, 1H).

IR (KBr) 3313, 3261, 3035, 2925, 2844, 1660, 1637, 1626, 1530, 1506, 1287, 1227, 1192, 1103, 1025, 810, 741, 696 cm$^{-1}$.

EXAMPLE 44

N-(3,5-dichloropyrid-4-yl)-4-methoxy-8-(ethylaminothiocarboxamido)-dibenzo[b,d]furan-1-carboxamide

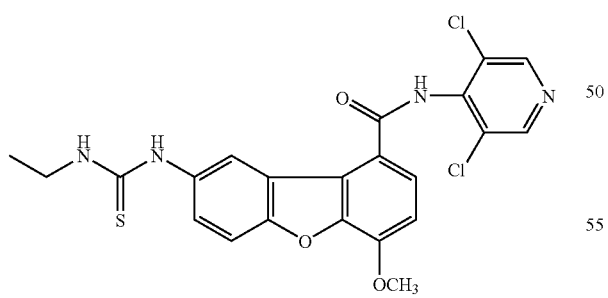

N-(3,5-dichloropyrid-4-yl)-4-methoxy-8-amino-dibenzo[b,d]furan-1-carboxamide (100 mg, 0.249 mmol) (intermediate 1) was suspended in THF (2 ml) followed by addition of pyridine (29 mg, 0.37 mmol) at room temperature. Reaction mixture was stirred for 10 min. followed addition of solution ethyl isothiocyanate (32 mg, 0.374 mmol) in THF (2 ml). The reaction mixture was stirred at room temperature for 3–4 days. THF was evaporated and the residue was stirred in water (5 ml). After filteration, the solid obtained was purified by silica gel column chromatography using 15% acetone-chloroform as eluent to obtain 40 mg of N-(3,5-dichloropyrid-4-yl)-4-methoxy-8-(ethylaminothiocarboxamido)-dibenzo[b,d]furan-1-carboxamide as white solid; mp: 260° C.

$^1$H NMR (300 MHz, DMSO-$d_6$) δ 1.29 (t, 3H), 3.24 (q, 2H), 4.14 (s, 3H), 7.34 (d, 1H, J=8.4 Hz), 7.59 (m, 3H), 7.70 (d, 1H, J=8.1 Hz), 7.89 (d, 1H, J=8.1 Hz), 8.32 (s, 1H), 8.76 (s, 2H), 9.45 (s, 1H), 10.79 (s, 1H).

IR (KBr) 3434, 3200, 3049, 2928, 1656, 1606, 1553, 1493, 1394, 1286, 1257, 1099, 803 cm$^{-1}$

EXAMPLE 45

N-(3,5-dichloropyrid-4-yl)-4-methoxy-8-(n-butylaminothiocarboxamido)-dibenzo[b,d]furan-1-carboxamide

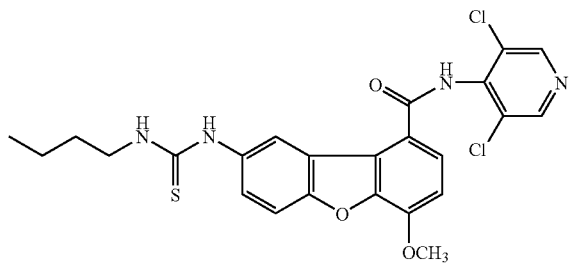

$^1$H NMR (300 MHz, DMSO-$d_6$)) δ 0.92 (t, 3H), 1.24 (m, 2H), 1.54 (m, 2H), 3.34 (m, 2H) 4.14 (s, 3H), 7.34 (d, 1H, J=8.4 Hz), 7.65 (m, 2H), 7.91(d, 1H, J=8.1 Hz), 8.24 (s, 1H), 8.32 (s, 1H), 8.75 (s, 2H), 9.44 (s, 1H), 10.75 (s, 1H).

IR (KBr)3195, 2928, 1658, 1606, 1549, 1480, 1393, 1283, 1257, 1194, 1100, 1021, 807 cm$^{-1}$

EXAMPLE 46

N1-(pyrid-3-yl)-4-methoxy-8-acetamido-dibenzo[b,d]furan-1-carboxamide

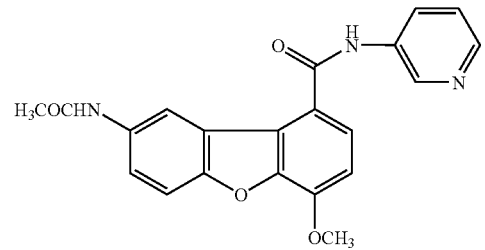

Step 1: N1-(pyrid-3-yl)-4-methoxy-8-nitro-dibenzo[b,d]furan-1-carboxamide 4-methoxy-8-nitro dibenzo[b,d]furan-1-carboxylic acid chloride (600 mg, 1.92 mmol) (from step 5a of intermediate 1) was reacted with 3-aminopyridine (1.1 eq.) in THF (20 ml) in the presence of diisopropylethylamine (0.5 ml) at room temperature for 12 h. The suspension was filtered and the solid obtained was washed with 5% HCl and water to obtain 500 mg of N1-(pyrid-3-yl)-4-methoxy-8-nitro-dibenzo[b,d]furan-1-carboxamide as white solid.

$^1$H NMR (300 MHz, DMSO-d$_6$) δ 4.15 (s, 3H), 7.44 (m, 2H), 8.00 (m, 2H), 8.26 (d, 1H, J=7.5 Hz), 8.35 (d, 1H, J=4.5 Hz), 8.46 (dd, 1H, J=9.0, 2.7 Hz), 8.95 (s, 1H), 9.37 (d, 1H, J=2.7 Hz), 10.77 (s, 1H).

Step 2: N1-(pyrid-3-yl)-4-methoxy-8-amino-dibenzo[b,d]furan-1-carboxamide

N1-(pyrid-3-yl)-4-methoxy-8-nitro-dibenzo[b,d]furan-1-carboxamide (500 mg) (from step1) was reduced using raney nickel (150 mg) (30% w/w aqueous suspension) in methanol (10 ml) in the presence of hydrazine hydrate (0.32 ml) under gentle reflux for 4 h. The reaction mixture was flitered through celite and the filtrate was concentrated in vaccuo. The residue was triturated with water, to obtain a solid which was filtered dried to give the product as white solid (300 mg).

Step 3: N1-(pyrid-3-yl)-4-methoxy-8-acetamido-dibenzo[b,d]furan-1-carboxamide

N1-(pyrid-3-yl)-4-methoxy-8-amino-dibenzo[b,d]furan-1-carboxamide (100 mg, 0.30 mmol) (step 2) was treated with acetyl chloride (1.1 eq.) in THF (10 ml) containing pyridine (1.1 eq) at 0° C. and allowed to warm to room temperature. The reaction was stirred at room temperature for 1 h. THF was evaporated and the residue was purified by silica gel column chromatography using 25% acetone-chloroform as eluent to obtain 6 mg of N1-(pyrid-3-yl)-4-methoxy-8-acetamido-dibenzo[b,d]furan-1-carboxamide as white solid;

mp: >250° C.

$^1$H NMR (300 MHz, DMSO-d$_6$) δ: 2.04 (s, 3H), 4.07 (s, 3H), 7.31 (d, 1H, J=8.1 Hz), 7.43–7.47 (dd, 1H J=8.2, 4.8 Hz), 7.68 (d, 1H, J=8.7 Hz), 7.78 (d, 1H, J=8.4 Hz), 7.90 (dd, 1H, J=2.4 Hz, 9 Hz), 8.22–8.25 (d, 1H), 8.35 (d, 1H, J=3.9 Hz), 8.41 (d, 1H, J=2.4 Hz), 8.98 (s, 1H), 10.10 (s, 1H), 10.71 (s, 1H)

IR (KBr): (cm$^{-1}$) 3271, 2922, 1646, 1289, 1102, 803.

EXAMPLE 47

N-(3,5-dichloropyrid-4-yl)-4-methoxy-8-acetamido-dibenzo[b,d]furan-1-carboxamide-N-oxide

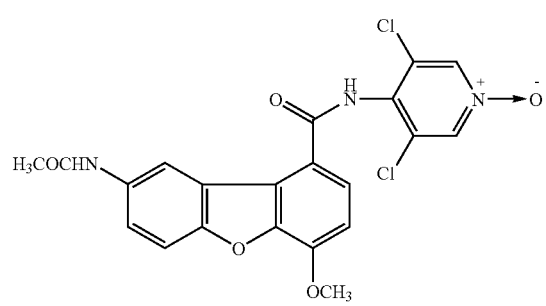

N-(3,5-dichloropyrid-4-yl)-4-methoxy-8-acetamido-dibenzo[b,d]furan-1-carboxamide (0.215 gm, 0.49 mmole) (Example 4) was suspended in dichloromethane.

To this reaction mixture was added 0.507 gm (2.9 mmoles) of meta-chloroperbenzoic acid (50%) and reaction mixture was refluxed for 3 hours and stirred at room temp. for 12 hours. Dichloromethane was removed under vaccum and the crude compound was purified through silica gel column to obtain 0.066 gm (30%) of the N-oxide.

$^1$H NMR (300 MHz, DMSO-d$_6$) δ: 2.01 (s, 3H), 4.06 (s, 3H), 7.33 (d, 1H), 7.67 (d, 1H), 7.90 (m, 2H), 8.43 (d, 1H), 8.75 (s, 2H), 10.07 (s, 1H), 10.61 (s, 1H)

IR (KBr): 3308, 3118, 2926, 2853, 1656, 1606, 1542, 1489, 1285, 1102, 828, cm$^{-1}$

Mass: (M+H)=460.1

EXAMPLE 48

N-(3,5-dichloropyrid-4-yl)-4-methoxy-8-methane-sulfonamido-dibenzo[b,d]furan-1-carboxamide-N-oxide

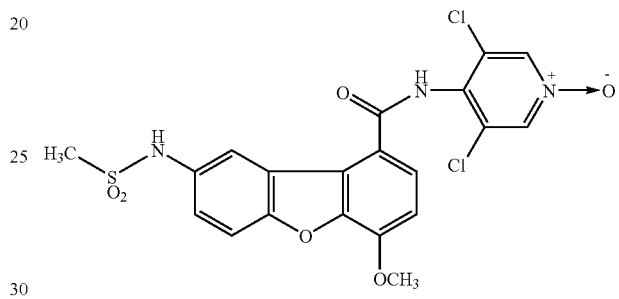

Was synthesized by using reaction conditions similar to those for the preparation of Example 47 except for starting with N-(3,5-dichloropyrid-4-yl)-4-methoxy-8-methane-sulfonamido-dibenzo[b,d]furan-1-carboxamide (0.2 gm, 4 mmoles) (Example 1) instead of N-(3,5-dichloropyrid-4-yl)-4-methoxy-8-acetamido-dibenzo[b,d]furan-1-carboxamide (Example 4).

Yield=0.04 gm (19%).

$^1$H NMR (300 MHz, DMSO-d$_6$) δ: 2.93 (s, 3H), 4.082 (s, 3H), 7.373 (d, 1H), 7.44 (d, 1H), 7.77 (d, 1H

IR (KBr):-526, 3304, 2926, 2851, 1654, 1606, 1484, 1279, 1235, 1150, 1103, 987, 828 cm$^{-1}$.

Mass: —(M+H)=496.1

EXAMPLE 49

N-(pyrid-4-yl)-4-methoxy-8-acetamido-dibenzo[b,d]furan-1-carboxamide

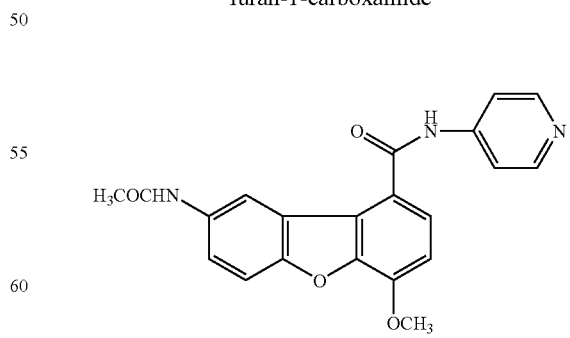

A solution of N-(3,5-dichloropyrid-4-yl)-4-methoxy-8-acetamido-dibenzo[b,d]furan-1-carboxamide (60 mg) (Example 4) and 25–28% aqueous ammonium hydroxide (3 ml) in THF (35 ml) was hydrogenated at 50 psi using 10% Pd/C (60 mg) for 24 h at room temperature. The reaction was filtered through celite and the filtrate was concentrated. The residue was dissolved in DCM, washed with water and brine, dried over anhydrous sodium sulfate and concentrated. The residue was purified by silica gel column chromatography using 2–10% methanol in DCM as eluent to obtain 21 mg (42%) of N-(pyrid-4-yl)-4-methoxy-8-acetamido-dibenzo[b,d]furan-1-carboxamide as white solid. mp: 267–268° C.

$^1$H NMR (300 MHz, DMSO-$d_6$) δ: 2.04 (s, 3H), 4.07 (s, 3H), 7.30 (d, 2H, J=8.7 Hz), 7.68 (d, 1H, J=8.7 Hz), 7.78 (d, 1H, J=8.4 Hz), 7.82 (d, 2H, J=6.6 Hz), 7.88 (dd, 1H, J=1.8 and 8.7 Hz), 8.40 (d, 1H, J=1.8 Hz), 8.52 (d, 2H, J=6.0 Hz), 10.11 (s, 1H), 10. 88 (s, 1H).

IR (KBr): 3243, 3140, 2976, 2931, 2844, 1696, 1669, 1633, 1599, 1579, 1509, 1473, 1385, 1330, 1285, 1269, 1202, 1102, 827, 808 cm$^{-1}$

EXAMPLE 50

N-(3,5-dichloropyrid-4-yl)-4-methoxy-8-(2-ethoxy-2-oxo-ethylaminocarbonylamino)-dibenzo[b,d]furan-1-carboxamide

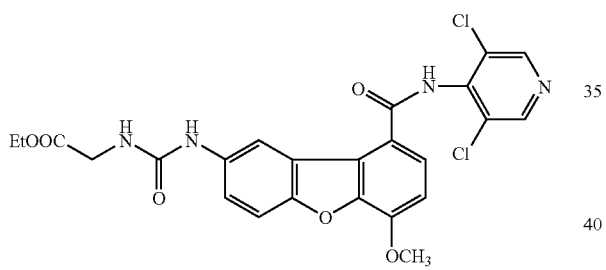

N-(3,5-dichloropyrid-4-yl)-4-methoxy-8-phenoxycarboxamido-dibenzo[b,d]furan-1-carboxamide (Example 17) (100 mg, 0.19 mmol), was dissolved in DMSO (2.0 ml) and a solution of glycine ethyl ester hydrochloride (26 mg, 0.19 mmol) and triethylamine (1.0 ml) in DMSO (2.0 ml) was added slowly to the above solution. The reaction mixture was stirred at 50° C. for 5 h, cooled to room temperature and diluted with ice water (25 ml) and acidified with 5% hydrochloric acid. The solid that separated as a result was filtered, dried and purified by silica gel column chromatography using 5% methanol in chloroform as eluent to obtain 30 mg of N-(3,5-dichloropyrid-4-yl)-4-methoxy-8-(2-ethoxy-2-oxo-ethylaminocarbonylamino)-dibenzo[b,d]furan-1-carboxamide as white solid; mp: >250° C.

$^1$H NMR (300 MHz, DMSO-$d_6$)-δ: 1.19 (t, 3H), 3.87 (d, 2H), 4.08–4.14 (m, 5H), 6.33 (t, 1H), 7.35 (d, 1H, J=8.7 Hz), 7.65 (d, 1H, J=9.3 Hz), 7.90–7.94 (m, 2H), 8.19 (d, 1H, J=2.1 Hz), 8.79 (s, 2H), 8.98 (s, 1H), 10.80 (s, 1H)

IR (KBr) 3339, 3148, 2959, 1763, 1659, 1640, 1579, 1489, 1392, 1292, 1199, 1159, 1100, 1022, 910, 806 cm$^{-1}$

EXAMPLE 51

N-(3,5-dichloropyrid-4-yl)-4-methoxy-8-(2-hydroxy-2-oxo-ethylaminocarbonylamino)-dibenzo[b,d]furan-1-carboxamide

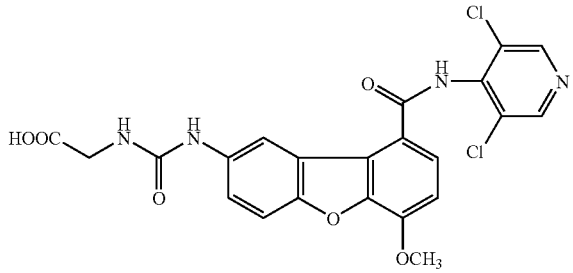

N-(3,5-dichloropyrid-4-yl)-4-methoxy-8-(2-ethoxy-2-oxo-ethylamino carbonylamino)-dibenzo[b,d]furan-1-carboxamide (Example 50) (150 mg, 0.28 mmol) was hydrolysed using potassium hydroxide (2 eq.) in 3 ml water and 3 ml methanol for 30 min. at room temperature. The solid precipitated was filtered and washed with methanol to obtain the product as white solid (50 mg).mp: >250° C.

$^1$H NMR (300 MHz, DMSO-$d_6$)-δ: 3.80 (d, 2H), 4.08 (s, 3H), 6.28 (t, 1H), 7.33 (d, 1H, J=8.7 Hz), 7.64 (d, 1H, J=9.3 Hz), 7.93 (m, 2H), 8.18 (d, 1H, J=2.1 Hz), 8.79 (s, 2H), 8.97 (s, 1H), 10.80 (s, 1H), 12.5 (brs, 1H).

IR (KBr) 3322, 3138, 2936, 1740, 1657, 1638, 1567, 1522, 1394, 1293, 1218, 1198, 1098, 1024, 910, 886, 806, 721 cm$^{-1}$

EXAMPLE 52

N-(3,5-dichloropyrid-4-yl)-4-methoxy-8-(2-ethoxy-2-oxo-ethylamino)-dibenzo[b,d]furan-1-carboxamide

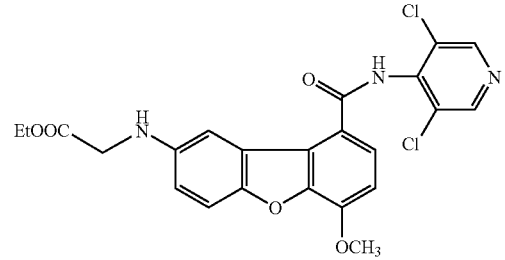

N-(3,5-dichloropyrid-4-yl)-4-methoxy-8-amino dibenzo[b,d]furan-1-carboxamide (500 mg, 1.24 mmol) was suspended in ethanol and a 50% solution of ethyl glyoxalate in toluene (384 mg, 3.72 mmol) was added to the suspension. The reaction mixture was hydrogenated at 40 psi in presence of pre-activated raney nickel (50% w/w) for 24 h–48 h. The reaction was filtered and the filtrate was concentrated in vacuo. The residue was purified by silica gel (100–200) column chromatography using 0.5% methanol in dichloromethane to obtain the compound as a pale yellow solid (180 mg). mp: >270° C.

$^1$H NMR (300 MHz, DMSO-$d_6$) δ: 1.06 (t, 3H), 3.85 (d, 2H), 4.01–4.05 (m, 5H), 6.09 (t, 1H), 6.88(dd, 1H, J=8.7 and 3.0 Hz), 7.26 (d, 1H, J=8.7 Hz), 7.43–7.55 (m, 2H), 7.81 (d, 1H, J=8.7 Hz), 8.79 (s, 2H), 10.75 (s, 1H)

IR (KBr): 3405, 3182, 2985, 1741, 1663, 1610, 1487, 1285, 1198, 1096, 1023, 807 cm–1

EXAMPLE 53

N-(3,5-dichloropyrid-4-yl)-4-methoxy-8-(2-hydroxy-2-oxo-ethylamino)-dibenzo[b,d]furan-1-carboxamide

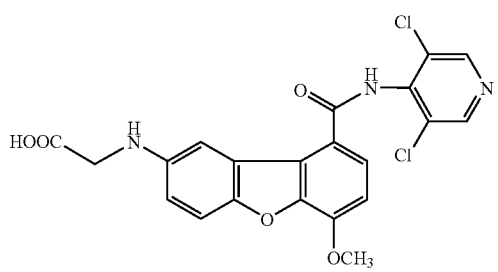

N-(3,5-dichloropyrid-4-yl)-4-methoxy-8-(2-ethoxy-2-oxo-ethylamino)-dibenzo[b,d]furan-1-carboxamide (Example 52) (100 mg, 0.204 mmol) was hydrolysed using potassium hydroxide (5 eq.) in 3 ml water and 3 ml methanol for 12 h at room temperature. The solid precitated was filted and washed with ethanol to obtain the product as pale yellow solid (50 mg). mp: >260° C.

$^1$H NMR (300 MHz, DMSO-$d_6$) δ: 3.77 (s, 2H), 4.05 (s, 3H), 6.88 (dd, 1H, J=9.0 and 2.1 Hz), 7.26 (d, 1H, J=9.0 Hz), 7.47–7.50 (m, 2H), 7.81 (d, 1H, J=8.4 Hz), 8.79 (s, 2H), 10.77 (s, 1H)

IR (KBr) 3416, 3177, 2936, 1726, 1662, 1609, 1487, 1398, 1285, 1196, 1095, 802 cm$^{-1}$.

EXAMPLE 54

N-(3,5-dichloropyrid-4-yl)-1-methoxy-9-methyl-6-acetamido-9H-4-carbazolecarboxamide

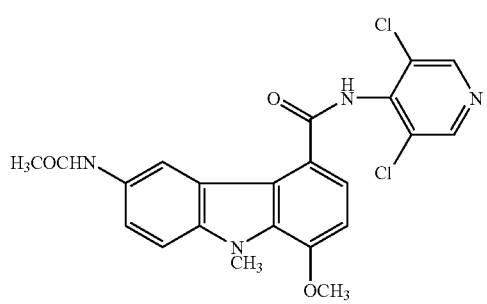

N-(3,5-dichloropyrid-4-yl)-1-methoxy-9-methyl-6-amino-9H-4-carbazolecarboxamide (75 mg, 0.00018 mol) was suspended in THF (5 ml) and added with pyridine (28 mg, 0.00036 mol) and stirred at room temperature for 10 minutes. The solution obtained, was added with a solution of acetyl chloride in dry THF (5 ml). The reaction mixture was stirred for 1 hr. THF was evaporated and the solid was washed with water to get crude solid which was column chromatographed using 10% methanol in chloroform to give N-3,5-dichloropyrid-4-yl)-1-methoxy-9-methyl-6-acetamido-9H-4-carbazolecarboxamide(20 mg),mp>250° C.

IR (KBr): 3292, 3171, 2935, 2838, 1658, 1575, 1547, 1483, 1397, 1283, 1260, 1234, 1106, 808 cm$^{-1}$.

$^1$H NMR (300 MHz, DMSO): δ 2.01 (s, 3H), 4.04 (s, 3H), 4.15 (s, 3H), 7.15 (d, 1H, J=8.4 Hz), 7.51 (d, 1H, J=8.7 Hz), 7.62 (d, 1H, J=8.1 Hz), 7.85 (dd, 1H, J=9.0 and 2.4 Hz), 8.31 (d, 1H, J=2.1 Hz), 8.78 (s, 2H), 9.89 (s, 1H), 10.67 (s, 1H).

EXAMPLE 55

N-(3,5-dichloropyrid-4-yl)-1-methoxy-9-methyl-6-methanesulphonamido-9H-4-carbazolecarboxamide

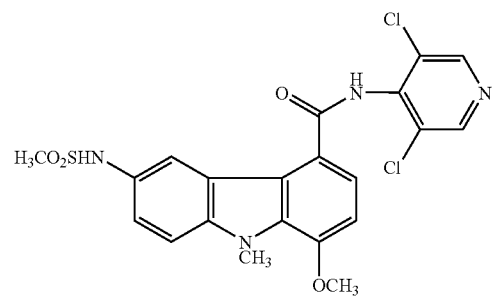

N-(3,5-dichloropyrid-4-yl)-1-methoxy-9-methyl-6-amino-9H-4-carbazolecarboxamide (75 mg, 0.00018 mol) was suspended in THF (5 ml) and added with pyridine (28 mg, 0.00036 mol) and stirred at room temperature for 10 minutes. The solution obtained, was added with a solution of methane sulphonyl chloride (30 mg, 0.00027 mol) in dry THF (5 ml). The reaction mixture was stirred for 1 hr. THF was evaporated and the solid was washed with water to get crude solid which was column chromatographed using 10% methanol in chloroform to give N-3,5-dichloropyrid-4-yl)-1-methoxy-9-methyl-6-methanesulphon-amido-9H-4-carbazolecarboxamide(20 mg),mp>250° C.

IR (KBr): 3268, 3138, 2962, 2935, 1655, 1573, 1547, 1483, 1400, 1311, 1257, 1235, 1144, 938, 804 cm$^{-1}$.

$^1$H NMR (300 MHz, DMSO): δ 2.50 (s, 3H), 4.05 (s, 3H), 4.17 (s, 3H), 7.18 (d, 1H, J=8.4 Hz), 7.40 (dd, 1H, J=9.0 and 2.1 Hz), 7.41–7.64 (m, 2H), 8.30 (d, 1H, J=2.4 Hz), 8.79 (s, 2H), 9.41 (s, 1H), 10.71 (s, 1H).

EXAMPLE 56

N-(3,5-dichloropyrid-4-yl)-1-methoxy-9-methyl-6-ethanesulphonamido-9H-4-carbazolecarboxamide

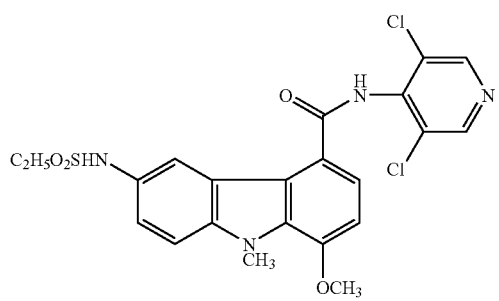

N-(3,5-dichloropyrid-4-yl)-1-methoxy-9-methyl-6-amino-9H-4-carbazolecarboxamide (75 mg, 0.00018 mol) was suspended in THF (5 ml) and added with pyridine (28 mg, 0.00036 mol) and stirred at room temperature for 10 minutes. The solution obtained, was added with a solution of ethane sulphonyl chloride (34 mg, 0.00027 mol) in dry THF (5 ml). The reaction mixture was stirred for 1 hr. THF was evaporated and the solid was washed with water to get crude solid which was column chromatographed using 10% methanol in chloroform to give N-3,5-dichloropyrid-4-yl)-1-methoxy-9-methyl-6-ethane sulphonamido-9H-4-carbazolecarboxamide (20 mg), mp>250° C.

IR (KBr): 3270, 3140, 2935, 1677, 1574, 1481, 1325, 1256, 1144, 1108, 949, 732 cm$^{-1}$.

$^1$H NMR (300 MHz, DMSO): δ 1.24 (t, 3H), 2.95 (q, 2H), 4.05 (s, 3H), 4.17 (s, 3H), 7.16 (d, 1H, J=8.4 Hz), 7.40 (dd, 1H, J=9.0 and 2.1 Hz), 7.58–7.63 (m, 2H), 8.29 (d, 1H, J=2.4 Hz), 8.79 (s, 2H), 9.49 (s, 1H), 10.70 (s, 1H).

EXAMPLE 57

N-(3,5-dichloropyrid-4-yl)-1-methoxy-9-methyl-6-propionamido-9H-4-carbazolecarboxamide

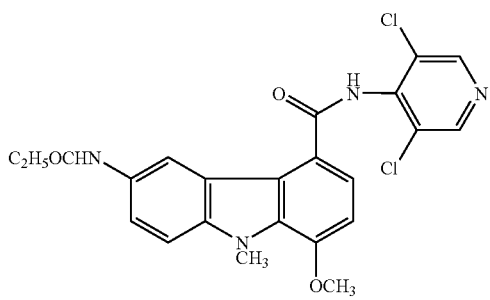

N-(3,5-dichloropyrid-4-yl)-1-methoxy-9-methyl-6-amino-9H-4-carbazolecarboxamide (75 mg, 0.00018 mol) was suspended in THF (5 ml) and added with pyridine (28 mg, 0.00036 mol) and stirred at room temperature for 10 minutes. The solution obtained, was added with a solution of propionyl chloride (24 mg, 0.00027) in dry THF (5 ml). The reaction mixture was stirred for 1 hr. THF was evaporated and the solid was washed with water to get crude solid which was column chromatographed using 10% methanol in chloroform to give N-3,5-dichloropyrid-4-yl)-1-methoxy-9-methyl-6-propionamido-9H-4-carbazolecarboxamide(20 mg), mp>250° C.

IR (KBr): 3282, 3138, 2966, 2938, 1656, 1645, 1481, 1397, 1313, 1283, 1260, 1232, 1106, 1087, 802 cm$^{-1}$.

$^1$H NMR (300 MHz, DMSO): δ 1.15 (t, 3H), 2.15 (q, 2H), 4.04 (s, 3H), 4.14 (s, 3H), 7.15 (d, 1H, J=8.4 Hz), 7.52 (d, 1H, J=8.7 Hz), 7.62 (d, 1H, J=8.1 Hz), 7.88 (dd, 1H, J=9.0 and 2.4 Hz), 8.33 (d, 1H, J=2.1 Hz), 8.77 (s, 2H), 9.82 (s, 1H), 10.66 (s, 1H).

EXAMPLE 58

N-(3,5-dichloropyrid-4-yl)-4-difluoromethoxy-8-methanesulfonamido-dibenzo[b,d]furan-1-carboxamide disodium salt

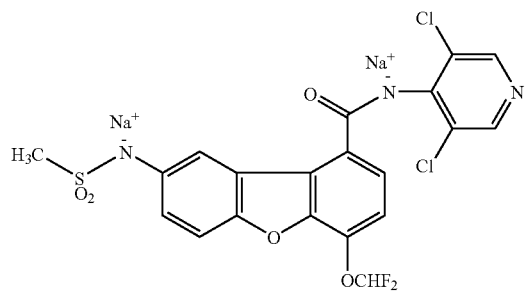

Was synthesized from N-(3,5-dichloropyrid-4-yl)-4-difluoromethoxy-8-methanesulfonamido-dibenzo[b,d]furan-1-carboxamide (Example 30) using ethanolic sodium ethoxide $^1$H NMR (300 MHz, DMSO-d$_6$) δ 2.53 (s, 3H), 7.06 (dd, 1H, J=8.7 and 2.1 Hz), 7.14 (d, 1H, J=8.4 Hz), 7.29 (d, 1H, J=8.7 Hz), 7.37 (t, 1H, J=72 Hz), 7.85 (d, 1H, J=8.4 Hz), 8.18 (s, 2H), 8.22 (d, 1H, J=2.4 Hz), IR (KBr) 2929, 1524, 1462, 1395, 1275, 1197, 1105, 1005, 890, 814 cm$^{-1}$

EXAMPLE 59

N-(3,5-dichloropyrid-4-yl)-1-methoxy-6-acetamido-dibenzo[b,d]thiophene-4-carboxamide

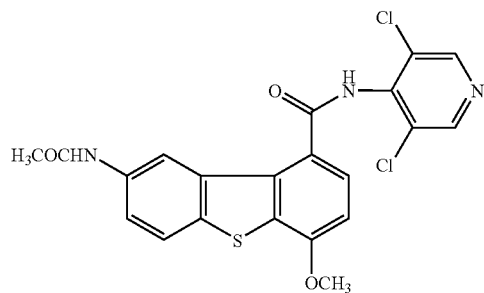

Step 1: 3-nitro-4-(2-methoxy thiophenoxy)-acetophenone

To a stirred suspension of potassium fluoride (2.48 gm, 0.04286 mol) in dry DMSO (10 ml) was added a solution of 2-methoxy thiophenol (5 gm, 0.0357 mol) in DMSO (10 ml). A solution of 4-fluoro 3-nitro acetophenone (7.88 gm, 0.04286 mol) in DMSO (10 ml) was added to the above suspension and the reaction mixture was stirred at 70–80° C. under nitrogen for 4 h. The reaction mixture was cooled to room temperature and the contents were poured into water (150 ml) and stirred for 15 minutes. The pale yellow coloured solid appeared was then filtered and washed with saturated sodium bicarbonate solution followed by water and dried under vaccum. The compound was obtained as pale yellow solid (8.1 gm) mp:—136–138° C.

IR (KBr): 3374, 3095, 3054, 2920, 1958, 1831, 1694, 1611, 1538, 1351, 1262, 1104, 978, 853, 814, 724 cm$^{-1}$.

$^1$H NMR (300 MHz, DMSO): δ 2.59 (s, 3H), 3.75 (s, 3H), 6.86 (d, 1H, J=8.7 Hz), 7.11 (t, 1H, J=7.8 Hz), 7.26 (d, 1H, J=8.4 Hz), 7.65 (m, 2H), 8.05 (d, 1H, J=8.7 Hz), 8.68 (s, 1H).

Step 2: 3-amino-4-(2-methoxy thiophenoxy)-acetophenone

To the solution of 3-nitro-4-(2-methoxy thiophenoxy)-acetophenone (8 gm, 0.02631 mol) in methanol, raney nickel (50%) was added. Then 4–5 kg/cm$^2$ hydrogen pressure was applied for 7 hrs at room temperature. The reaction mixture was filtered through cilites to remove raney nickel. Filtrate was concentrated. Thick oil obtained (5.12) was used in the next step.

IR (KBr): 2958, 2922, 2852, 1682, 1557, 1465, 1420, 1261, 1092, 1021, 803, 757 cm$^{-1}$.

$^1$H NMR (300 MHz, DMSO): δ 2.50 (s, 3H), 3.85 (s, 3H), 5.55 (s, 2H) 6.65 (d, 1H, J=7.8 Hz), 6.84 (t, 1H, J=7.2), 7.03 (d, 1H, J=8.4 Hz), 7.19 (m, 2H), 7.29 (d, 1H, J=7.8), 8.37(s, 1H).

Step 3: 1-methoxy-6-acetyl dibenzo[b,d]thiophene 3-amino-4-(2-methoxy thiophenoxy)-acetophenone (5 gm, 0.01824 mol) was dissolved in 1:1 HCl (50 ml). The reaction mixture was cooled below 5° C. To this reaction mixture, sodium nitrite (1.88 gm, 0.02736 mol) was added slowly with maintaining temperature below 5° C. after addition, reaction was stirred for 30 minutes below 5° C. Then sodium fluoroborate (3.97 gm, 0.03648 mol) was added to it and stirred for another 30 minutes at and below 5° C. Above diazotized solution was then added to the stirred solution of copper(I) oxide (5.21 gm, 0.03648 mol) in 0.1N sulfuric acid (1800 ml) at 35–40° C. The reaction mixture was stirred for 15–30 minutes. Ethyl acetate was added to the reaction mixture and filtered to remove inorganic compound. Filtrate was then extracted by ethyl acetate (3×150 ml). Organic volume was washed with water followed by brine and then concentrated under vacuum. Brown colored solid (3.6 gm) was obtained. mp—136–138° C.

IR (KBr): 3432, 2943, 2841, 1673, 1572, 1488, 1429, 1362, 1269, 1051, 888, 822, 782 cm$^{-1}$.

$^1$H NMR (300 MHz, DMSO): δ 2.73 (s, 3H), 4.02 (s, 3H), 7.19 (d, 1H, J=7.8 Hz), 7.56 (t, 1H, J=7.8 Hz), 8.06 (d, 1H, J=8.7), 8.16 (m, 2H), 8.94 (s, 1H).

Step-4: Oxime Preparation 1-methoxy-6-acetyl dibenzo[b,d]thiophene (3.5 gm, 0.01286 mol) was suspended in methanol (30 ml) to which hydroxylamine hydrochloride (1.78 gm, 0.02573 mol), sodium hydroxide (1.029 gm, 0.02573 mol) and water was added. Whole reaction mixture was then refluxed for 6–7 hrs. Methanol was then distilled out under vacuum. Then water was added to the reaction mass. The white colored solid appeared was then filtered and dried under vacuum (2.7 gm).mp 168–170° C.

IR (KBr): 3217, 3060, 2966, 2919, 2833, 1570, 1485, 1470, 1428, 1328, 1256, 1054, 1026, 936, 887, 776, 759, 705 cm$^{-1}$.

$^1$H NMR (300 MHz, DMSO): δ 2.30 (s, 3H), 4.0 (s, 3H), 7.14 (d, 1H, J=7.8 Hz), 7.51 (t, 1H, J=7.8 Hz), 7.86 (d, 1H, J=8.7 Hz), 8.03 (m, 2H), 8.53 (s, 1H), 11.28 (s, 1H).

Step 5: 1-methoxy-6-acetamido dibenzo[b,d]thiophene

Oxime (2.7 gm, 0.00992 mol) was dissolved in dry THF. Then thionyl chloride (3.54 gm, 0.02977 mol) was added at 25° C. and the solution was stirred for 30 minutes. Reaction mass was dumped in ice-water. Red colored solid appeared was then filtered and washed with water. The solid was purified by silica gel (100–200) column chromatography using 20% ethyl acetate in chloroform yield 1.5 gm, MP-decomposes at 170–174° C.

IR (KBr): 3296, 2938, 1658, 1568, 1471, 1428, 1260, 1096, 1025, 805, 775 cm$^{-1}$.

$^1$H NMR (300 MHz, DMSO): δ 2.10 (s, 3H), 3.46 (s, 3H), 7.12 (d, 1H, J=7.8 Hz), 7.49 (t, 1H, J=7.8 Hz), 7.63 (d, 1H, J=8.4 Hz), 7.76 (d, 1H, J=7.8 Hz), 7.94 (d, 1H, J=9 Hz), 8.56 (s, 1H), 10.22(s, 1H).

Step 6: 1-methoxy-6-acetamido dibenzo[b,d]thiophene-4-carbaldehyde 1-methoxy-6-acetamido dibenzo[b,d]thiophene (1.5 gm, 0.0055 mol) was suspended in dichloromethane (25 ml) and the solution was cooled to −10° C. To this solution was added tin (IV) chloride (7.3 gm, 0.0275 mol) all at once at −10° C. under nitrogen atmosphere followed by drop wise addition of a solution of dichloromethyl methyl ether (0.948 gm, 0.008 mol) in dichloromethane (5 ml) at −10° C. The reaction mixture was allowed to attain room temperature under stirring for 30 min. Cold water (20 ml) was added to the reaction mixture and extracted with dichloromethane (25 ml×3). The organic layer was washed with water and dried over anhydrous sodium sulphate. The organic layer was concentrated under vacuum to give the crude product brown sticky solid (800 mg),mp—247–250° C.

IR (KBr): 3347, 2923, 2851, 1678, 1664, 1578, 1557, 1530, 1459, 1278, 1248, 1222, 1067, 1014, 822, 753, 693, 599 cm$^{-1}$.

$^1$H NMR (300 MHz, DMSO): δ 2.10 (s, 3H), 4.12 (s, 3H), 7.36 (d, 1H, J=8.10 Hz), 7.94 (d, 1H, J=9.0 Hz), 8.03 (d, 1H, J=8.7 Hz), 8.13 (d, 1H, J=8.4 Hz), 9.75 (s, 1H), 10.23 (s, 1H), 10.49 (s, 1H).

Step 7: 1-methoxy-6-acetamido dibenzo[b,d]thiophene-4-carboxylic acid

To a solution of 1-methoxy-6-acetamido dibenzo[b,d]thiophene-4-carbaldehyde (800 mg, 0.00266 mol) in THF (15 ml) and water(2 ml) was added sulfamic acid (387 mg, 0.004 mmol) while stirring at 10° C. A solution of 80% sodium chlorite (360 mg, 0.004 mmol) in water (2.0 mL) was added drop wise to the above reaction mixture over a period of 5 min and was allowed to stir at 110° C. for additional 30 min. Water (150 ml) was added to obtain a precipitate which filtered and dried under vacuum (350 mg).

MP-decomposes above 275° C.

IR (KBr): 3349, 3132, 3048, 2611, 1670, 1587, 1561, 1537, 1459, 1264, 1013, 821, 782 cm$^{-1}$

Step 8: Mixed Anhydride Preparation:

1-methoxy-6-acetamido dibenzo[b,d]thiophene-4-carboxylic acid (300 mg, 0.000949 mol) was dissolved in DMF (10 ml) and the solution was cooled to −20° C. Isobutyl chloroformate (190 mg, 0.001423 mol) and diisopropyl n-ethyl amine (244 mg, 0.0019 mol) was added at −20° c and stirred for 10–12 hrs. Reaction mass was dumped in water (100 ml). The solid appeared was filtered and dried under vacuum (270 mg).mp—125–130° C.

IR (KBr): 3283, 2960, 1779, 1743, 1658, 1561, 1527, 1459, 1370, 1293, 1269, 1197, 1178, 1066, 1007, 813, 770, 730 cm$^{-1}$.

$^1$H NMR (300 MHz, DMSO): δ 0.95 (d, 6H, J=6.9 Hz), 2.08 (m, 4H), 4.13 (m, 5H), 7.27 (d, 1H, J=8.1), 7.91 (d, 1H, J=8.7), 8.02 (d, 1H, J=9 Hz), 8.15 (d, 1H, J=8.4 Hz), 8.81 (s, 1H), 10.2 (s, 1H).

Step 9: N-(3,5-dichloropyrid-4-yl)-1-methoxy-6-acetamido-dibenzo[b,d]thiophene-4-carboxamide To the stirred solution of anhydride (270 mg, 0.000655 mol) and 4-amino 3,5-dichloro pyridine (118 mg, 0.00072 mol) in DMF (10 ml), 60% sodium hydride (52 mg, 0.0013 mol) was added at −20° C. Reaction was maintained for 30 minutes. Reaction mass was dumped in water (100 ml). The solid appeared was acidified with 10% HCl and filtered. The residue was washed with saturated sodium bicarbonate solution followed by water. The solid was purified by silica gel (100–200) column chromatography using 20% acetone in chloroform. (Yield 12 mg) mp-decomposes above 275° C.

IR (KBr): 3430, 3349, 3293, 1657, 1563, 1527, 1458, 1260, 1025, 807, 775 cm$^{-1}$.

$^1$H NMR (300 MHz, DMSO): δ 2.08 (s, 3H), 4.07 (s, 3H), 7.26 (d, 1H, J=8.4 Hz), 7.77 (d, 1H, J=8.1 Hz), 7.89 (d, 1H, J=8.7 Hz), 7.99 (d, 1H, J=8.7 Hz), 8.19 (s, 1H), 8.37(s, 1H).

EXAMPLE 60

N-(3,5-dichloropyrid-4-yl)-4-difluoromethoxy-8-acetamido-dibenzo[b,d]furan-1-carboxamide sodium salt

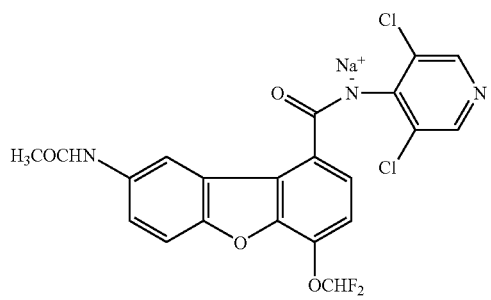

Was synthesized from N-(3,5-dichloropyrid-4-yl)-4-difluoromethoxy-8-acetamido-dibenzo[b,d]furan-1-carboxamide (Example 34) using ethanolic sodium ethoxide (1.0 eq.) in THF/ethanol.

$^1$H nmr (300 MHz, DMSO-d$_6$) δ 2.02 (s, 3H), 7.30 (d, 1H, J=7.8 Hz), 7.42 (t, 1H, J=73 Hz), 7.60 (d, 1H, J=9.0 Hz), 8.02–8.07 (m, 2H), 8.19 (s, 2H), 8.98 (d, 1H, J=2.1 Hz), 10.25 (s, 1H).

EXAMPLE 61

N-(3,5-dichloropyrid-4-yl)-4-difluoromethoxy-8-fur-2-ylcarboxamido-dibenzo[b,d]furan-1-carboxamide sodium salt

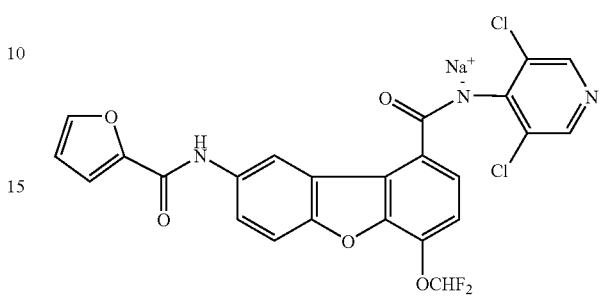

Was synthesized from N-(3,5-dichloropyrid-4-yl)-4-difluoromethoxy-8-fur-2-ylcarboxamido-dibenzo[b,d]furan-1-carboxamide (Example 40) using ethanolic sodium ethoxide (1.0 eq.) in THF/ethanol $^1$H nmr (300 MHz, DMSO-d$_6$) δ 6.68 (m, 1 Hz), 7.32 (d, 1H, J=8.7 Hz), 7.37 (d, 1H, J=3.6 Hz), 7.44 (t, 1H, J=72 Hz), 7.68 (d, 1H, J=8.7 Hz), 7.88–7.92 (m, 2H,), 7.82 (d, 1H, J=8.7 Hz),), 8.18 (s, 2H,). 9.20 (d, 1H, J=2.4 Hz), 10.33 (s, 1H).

In Vitro Studies

Inhibition of Phosphodiesterase Enzymes (PDE4)

In this assay, PDE4 enzyme converts [$^3$H] cAMP to the corresponding [$^3$H] 5'-AMP in proportion to the amount of PDE4 present. The [$^3$H] 5'-AMP then was quantitatively converted to free [$^3$H] adenosine and phosphate by the action of snake venom 5'-nucleotidase. Hence, the amount of [$^3$H] adenosine liberated is proportional to PDE4 activity.

The assay was performed with modification of the method of Thompson and Appleman (Biochemistry; 1971; 10; 311–316) and Schwartz and Passoneau (Proc. Natl. Acad. Sci. U.S.A. 1974; 71; 3844–3848), both references incorporated herein by reference in their entirety, at 34° C. In a 200 ul total reaction mixture, the reaction mixture contained 12.5 mM of Tris, 5 mM MgCl$_2$, 1 µM cAMP (cold) and $^3$H cAMP (0.1 uCi), (Amersham). Stock solutions of the compounds to be investigated were prepared in DMSO in concentrations such that the DMSO content in the test samples did not exceed 0.05% by volume to avoid affecting the PDE4 activity. Drug samples were then added in the reaction mixture (25 µl/tube). The assay was initiated by addition of enzyme mix (75 µl) and the mixture was incubated for 20 minutes at 34° C. The reaction was stopped by boiling the tubes for 2 mins at 100° C. in a water bath. After cooling on ice for 5 minutes and addition of 50 µg/reaction of 5'-nucleotidase snake venom from Crotalus atrox incubation was carried out again for 20 min. at 34° C. The unreacted substrate was separated from (3H) Adenosine by addition of Dowex AG 1-X8 (Biorad Lab), (400 ul) which was prequilibrated (1:1:1) in water and ethanol. Reaction mixture was then thoroughly mixed, placed on ice for 15 minutes, vortexed and centrifuged at 14,000 r.p.m. for 2 mins. After centrifugation, a sample of the supernatant was taken and added in 24 well optiplates containing Scintillant (1 ml) and mixed well. The samples in the plates were then determined for radioactivity in a Top Counter and the PDE4 activity was estimated. PDE4 enzyme was present in quantities that yield<30% total hydrolysis of substrate (linear assay conditions).

Additionally, activity of the compounds were tested against other Phosphodiesterase enzymes, namely, PDE 1(Ca.sup.2+/calmodulin-dependent), PDE 2(cGP-stimulated), PDE 3 (cGP-inhibited), PDE 5 (cGP-specific) and PDE 6 (cGP-specific, photoreceptor).

Results were expressed as percent inhibition ($IC_{50}$) in nM concentrations. The $IC_{50}$ values were determined from the concentration curves by nonlinear regression analysis.

| Example No. | $IC_{50}$ (nM) | $EC_{50}$ (nM) |
|---|---|---|
| 01 | 0.5058 | 8.57 |
| 02 | 1.027 | 2.07 |
| 03 | 0.7617 | 7.386 |
| 04 | 1.184 | 13.62 |
| 05 | 7.8 | 80.87 |
| 06 | 1.61 | 5.59 |
| 07 | 5.598 | 7.86 |
| 08 | 4.68 | 110.3 |
| 09 | 1.035 | 137.8 |
| 10 | 1.853 | 38.18 |
| 11 | 0.887 | 4.34 |
| 12 | 0.557 | 16.18 |
| 13 | 74.03 | — |
| 14 | 7.011 | 14.12 |
| 15 | 15.13 | — |
| 16 | 63.64 | — |
| 17 | 9.09 | 103.9 |
| 18 | 3.47 | 19.08 |
| 19 | 4.792 | 9.008 |
| 20 | 10.26 | 8.29 |
| 21 | 1.19 | 23.8 |
| 22 | 1.283 | 9.34 |
| 23 | 3.776 | 4.138 |
| 24 | 3.006 | 2.94 |
| 25 | 5.069 | 8.897 |
| 26 | 15.59 | — |
| 27 | 3.396 | 4.16 |
| 28 | 1.399 | 6.33 |
| 29 | 2.14 | 19.26 |
| 30 | 1.63 | 3.59 |
| 31 | 1.425 | 3.46 |
| 32 | 14.09 | — |
| 33 | 12.08 | — |
| 34 | 3.552 | 14.76 |
| 35 | 8.199 | 146.2 |
| 36 | 4.637 | 8.44 |
| 37 | 21.53 | >278.2 |
| 38 | 1.41 | 26.95 |
| 39 | 0.5981 | 9.19 |
| 40 | 22.04 | 11.33 |
| 41 | 156 | — |
| 42 | 959 | — |
| 43 | 17.93% at 1 μM | — |
| 44 | 1.719 | 3.93 |
| 45 | 0.7732 | 6.37 |
| 46 | 133.9 | — |
| 47 | 2.437 | 28.83 |
| 48 | 1.674 | 11.89 |
| 49 | 13.2 | — |
| 50 | 9.93 | 146.9 |
| 51 | 1.98 | 121.8 |
| 52 | 8.13 | 821 |
| 53 | 1.05 | 71.45 |
| 54 | 236.9 | — |
| 59 | 126.9 | — |

What is claimed is:
1. A compound of Formula (I)

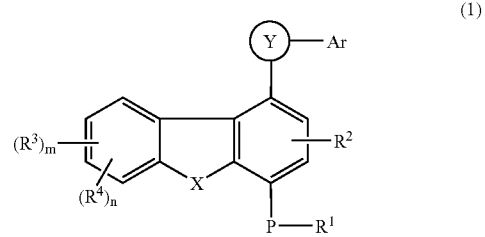

wherein:
$R^1$ is substituted or unsubstituted alkyl;
$R^2$ is hydrogen;
$R^3$ is hydrogen;
$R^4$ is $-NR^5R^6$, with the proviso that $R^4$ is not $NH_2$;
$R^5$ and $R^6$ may be same or different and are independently selected from the group consisting of hydrogen, substituted or unsubstituted alkyl, substituted or unsubstituted aryl, substituted or unsubstituted arylalkyl, substituted or unsubstituted heteroaryl, substituted or unsubstituted heterocyclic ring, substituted or unsubstituted heterocyclylalkyl, $-C(O)-R^a$, $-C(O)O-R^a$, $-C(O)NR^aR^a$, $-S(O)_q-R^a$, $-S(O)_q-NR^aR^a$, $-C(=S)-NR^aR^a$, $-C(=S)-R^a$, $-N=C(R^aR^a)$, or $-NR^aR^a$;
Ar is selected from the group consisting of substituted or unsubstituted aryl and substituted and unsubstituted heteroaryl ring;
X is selected from the group consisting of O and $S(O)_q$;
Y is $-C(O)NH$;
P is selected from the group consisting of O and S;
m is 0;
n is 1;
q represents 0,1 or 2;
$R^a$ is selected from the group consisting of hydrogen, substituted or unsubstituted alkyl, or substituted or unsubstituted heterocyclic ring;
or a N-oxide thereof, or a pharmaceutically acceptable salt thereof,
wherein the substituents in the substituted groups may be the same or different and in which one or more are selected from the group consisting of hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, substituted or unsubstituted heterocyclic ring, substituted or unsubstiuted guanidine, $-COOR^x$, $-C(O)R^x$, $-C(S)R^x$, $-C(O)NR^xR^y$, $-C(O)ONR^xR^y$, $-NR^xCONR^yR^z$, $-N(R^x)SOR^y$, $-N(R^x)SO_2R^y$, $-(=N-N(R^x)R^y)$, $-NR^xC(O)OR^y$, $-NR^xR^y$, $-NR^xC(O)R^y-$, $-NR^xC(S)R^y-NR^xC(S)NR^yR^z$, $-SONR^xR^y-$, $-SO_2NR^xR^y-$, $-OR^x$, $-OR^xC(O)NR^yR^z$, $-OR^xC(O)OR^y-$, $-OC(O)R^x$, $-OC(O)NR^xR^y$, $-R^xN-R^yC(O)R^z$, $-R^xOR^y$, $-R^xC(O)OR^y$, $-R^xC(O)NR^yR^z$, $-R^xC(O)R^x$, $-R^xOC(O)R^y$, $-SR^x$, $-SOR^x$, $-SO_2R^x$, or $-ONO_2$, wherein $R^x$, $R^y$ and $R^z$ in each of the above groups can be hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring.

2. The compound according to claim 1, wherein Ar is optionally substituted phenyl, optionally substituted pyrimidine, optionally substituted 4-pyridyl, optionally substituted 3-pyridyl, optionally substituted 2-pyridyl, optionally substituted 4-pyridyl-N-oxide, optionally substituted 3-pyridyl-N-oxide or optionally substituted 2-pyridyl-N-oxide in which the optional substituents (one or more) may be same or different and are independently selected from the group consisting of hydrogen, hydroxyl, halogen, cyano, nitro, carboxyl, trifluoroalkyl, substituted or unsubstituted alkyl, substituted or unsubstituted alkoxy, substituted or unsubstituted alkoxycarbonyl, substituted or unsubstituted alkylcarbonyl, substituted or unsubstituted alkylcarbonyloxy, substituted or unsubstituted amino or mono or di substituted or unsubstituted alkylamino.

3. The compound according to claim 1, wherein $R^1$ is unsubstituted alkyl.

4. The compound according to claim 3, wherein $R^1$ is methyl.

5. The compound according to claim 1, wherein $R^1$ is substituted alkyl.

6. The compound according to claim 5, wherein $R^1$ is —$CHF_2$.

7. The compound according to claim 1, wherein P is O.

8. The compound according to claim 1, wherein X is chosen from the group consisting of O and S.

9. The compound according to claim 8, wherein X=O.

10. The compound according to claim 1, wherein Ar is selected from the group consisting of substituted or unsubstituted 4-pyridyl, substituted or unsubstituted 4-pyridyl-N-oxide, or substituted or unsubstituted 3-pyridyl.

11. The compound according to claim 10, wherein said substituent in the substituted pyridyl group is a halogen.

12. The compound according to claim 11, wherein said halogen is chloro.

13. The compound according to claim 10, wherein Ar is selected from the group consisting of

14. The compound according to claim 13, wherein Ar is

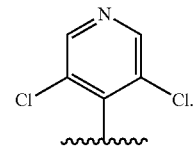

15. The compound according to claim 1 wherein $R^4$ is selected from the group consisting of

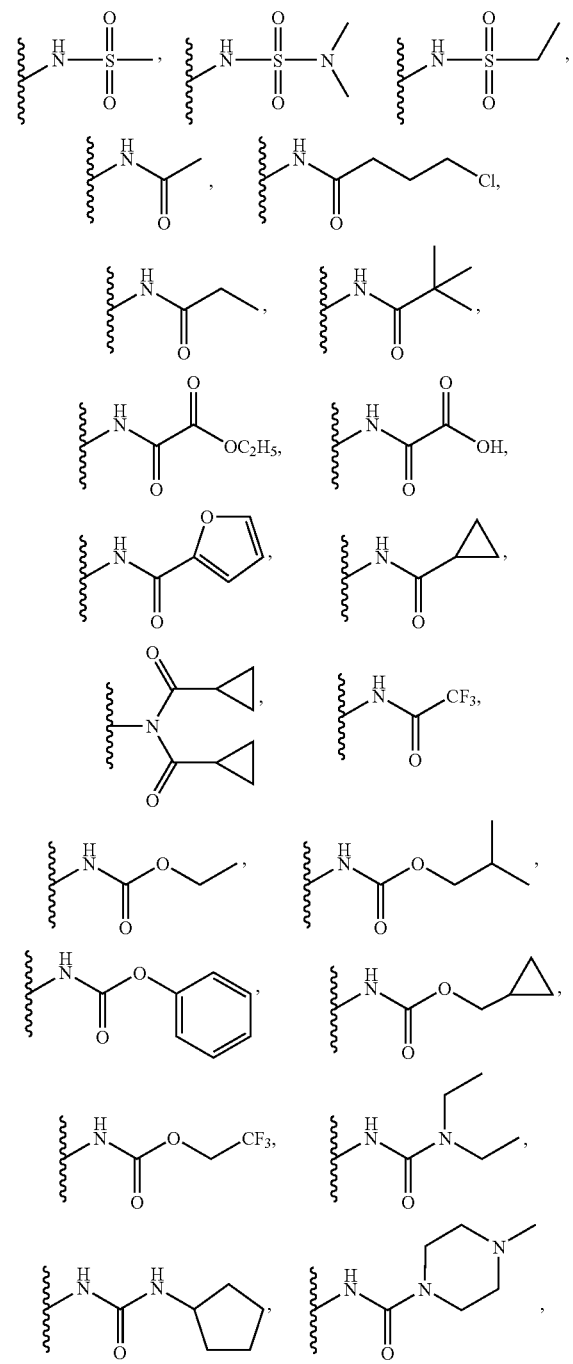

-continued

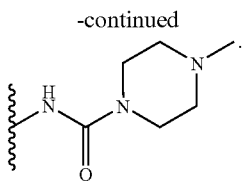

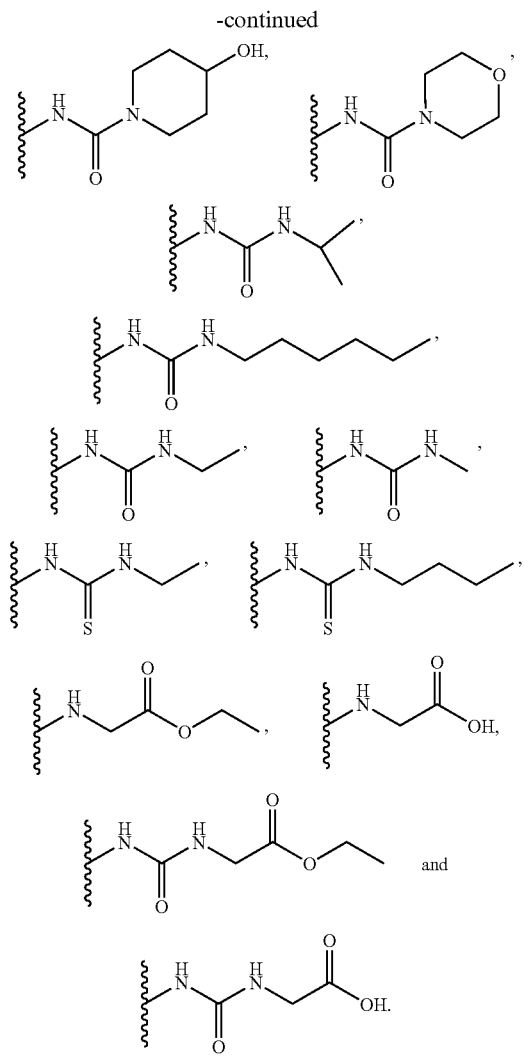

16. The compound according to claim 15 wherein R⁴ selected from the group consisting of

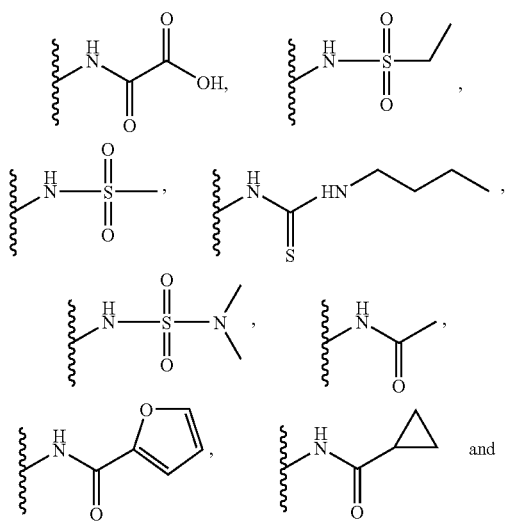

17. A compound according to claim 1, wherein the compound is N-(3,5-dichloropyrid-4-yl)-4-methoxy-8-methanesulfonamido-dibenzo[b,d]furan-1-carboxamide or a pharmaceutically acceptable salt thereof.

18. A compound according to claim 1, wherein the compound is N-(3,5-dichloropyrid-4-yl)-4-methoxy-8-(N,N-dimethylaminosulphonamido)-dibenzo[b,d]furan-1-carboxamide or a pharmaceutically acceptable salt thereof.

19. A compound according to claim 1, wherein the compound is N-(3,5-dichloropyrid-4-yl)-4-methoxy-8-(ethanesulphonamido)-dibenzo[b,d]furan-1-carboxamide or a pharmaceutically acceptable salt thereof.

20. A compound according to claim 1, wherein the compound is N-(3,5-dichloropyrid-4-yl)-4-methoxy-8-acetamido-dibenzo[b,d]furan-1-carboxamide or a pharmaceutically acceptable salt thereof.

21. A compound according to claim 1, wherein the compound is N-(3,5-dichloropyrid-4-yl)-4-methoxy-8-(3-chloropropylcarboxamido)-dibenzo[b,d]furan-1-carboxamide or a pharmaceutically acceptable salt thereof.

22. A compound according to claim 1, wherein the compound is N-(3,5-dichloropyrid-4-yl)-4-methoxy-8-ethylcarboxamido-dibenzo[b,d]furan-1-carboxamide or a pharmaceutically acceptable salt thereof.

23. A compound according to claim 1, wherein the compound is N-(3,5-dichloropyrid-4-yl)-4-methoxy-8-t-butylcarboxamido-dibenzo[b,d]furan-1-carboxamide or a pharmaceutically acceptable salt thereof.

24. A compound according to claim 1, wherein the compound is N-(3,5-dichloropyrid-4-yl)-4-methoxy-8-ethoxycarbonylcarboxamido-dibenzo[b,d]furan-1-carboxamide or a pharmaceutically acceptable salt thereof.

25. A compound according to claim 1, wherein the compound is N-(3,5-dichloropyrid-4-yl)-4-methoxy-8-hydroxycarbonylcarboxamido-dibenzo[b,d]furan-1-carboxamide or a pharmaceutically acceptable salt thereof.

26. A compound according to claim 1, wherein the compound is N-(3,5-dichloropyrid-4-yl)-4-methoxy-8-hydroxycarbonylcarboxamido-dibenzo[b,d]furan-1-carboxamide sodium salt.

27. A compound according to claim 1, wherein the compound is N-(3,5-dichloropyrid-4-yl)-4-methoxy-8-(fur-2-yl-carboxamido)-dibenzo[b,d]furan-1-carboxamide or a pharmaceutically acceptable salt thereof.

28. A compound according to claim 1, wherein the compound is N-(3,5-dichloropyrid-4-yl)-4-methoxy-8-(cyclopropylcarbonylamino)-dibenzo[b,d]furan-1-carboxamide or a pharmaceutically acceptable salt thereof.

29. A compound according to claim 1, wherein the compound is N-(3,5-dichloropyrid-4-yl)-4-methoxy-8-(N,N-dicyclopropylcarbonylamino)-dibenzo[b,d]furan-1-carboxamide or a pharmaceutically acceptable salt thereof.

30. A compound according to claim 1, wherein the compound is N-(3,5-dichloropyrid-4-yl)-4-methoxy-8-trifluoroacetamido-dibenzo[b,d]furan-1-carboxamide or a pharmaceutically acceptable salt thereof.

31. A compound according to claim 1, wherein the compound is N-(3,5-dichloropyrid-4-yl)-4-methoxy-8-ethoxycarboxamido-dibenzo[b,d]furan-1-carboxamide or a pharmaceutically acceptable salt thereof.

32. A compound according to claim 1, wherein the compound is N-(3,5-dichloropyrid-4-yl)-4-methoxy-8-isobutyloxycarboxamido-dibenzo[b,d]furan-1-carboxamide or a pharmaceutically acceptable salt thereof.

33. A compound according to claim 1, wherein the compound is N-(3,5-dichloropyrid-4-yl)-4-methoxy-8-phenoxycarboxamido-dibenzo[b,d]furan-1-carboxamide or a pharmaceutically acceptable salt thereof.

34. A compound according to claim 1, wherein the compound is N-(3,5-dichloropyrid-4-yl)-4-methoxy-8-cyclopropylmethoxycarboxamido-dibenzo[b,d]furan-1-carboxamide or a pharmaceutically acceptable salt thereof.

35. A compound according to claim 1, wherein the compound is N-(3,5-dichloropyrid-4-yl)-4-methoxy-8-trifluoromethylmethoxycarboxamido-dibenzo[b,d]furan-1-carboxamide or a pharmaceutically acceptable salt thereof.

36. A compound according to claim 1, wherein the compound is N-(3,5-dichloropyrid-4-yl)-4-methoxy-8-N,N-diethylaminocarboxamido-dibenzo[b,d]furan-1-carboxamide or a pharmaceutically acceptable salt thereof.

37. A compound according to claim 1, wherein the compound is N-(3,5-dichloropyrid-4-yl)-4-methoxy-8-cyclopentylaminocarboxamido-dibenzo[b,d]furan-1-carboxamide or a pharmaceutically acceptable salt thereof.

38. A compound according to claim 1, wherein the compound is N-(3,5-dichloropyrid-4-yl)-4-methoxy-8-(N-methylpiperazin-4-yl carboxamido)-dibenzo[b,d]furan-1-carboxamide or a pharmaceutically acceptable salt thereof.

39. A compound according to claim 1, wherein the compound is N-(3,5-dichloropyrid-4-yl)-4-methoxy-8-(N-methylpiperazin-4-yl carboxamido)-dibenzo[b,d]furan-1-carboxamide hydrochloride.

40. A compound according to claim 1, wherein the compound is N-(3,5-dichloropyrid-4-yl)-4-methoxy-8-(4-hydroxypiperidin-1-yl carboxamido)-dibenzo[b,d]furan-1-carboxamide or a pharmaceutically acceptable salt thereof.

41. A compound according to claim 1, wherein the compound is N-(3,5-dichloropyrid-4-yl)-4-methoxy-8-(morphol-4-yl carboxamido)-dibenzo[b,d]furan-1-carboxamide or a pharmaceutically acceptable salt thereof.

42. A compound according to claim 1, wherein the compound is N-(3,5-dichloropyrid-4-yl)-4-methoxy-8-isopropylamino carboxamido-dibenzo[b,d]furan-1-carboxamide or a pharmaceutically acceptable salt thereof.

43. A compound according to claim 1, wherein the compound is N-(3,5-dichloropyrid-4-yl)-4-methoxy-8-n-hexylamino carboxamido-dibenzo[b,d]furan-1-carboxamide or a pharmaceutically acceptable salt thereof.

44. A compound according to claim 1, wherein the compound is N-(3,5-dichloropyrid-4-yl)-4-methoxy-8-ethylamino carboxamido-dibenzo[b,d]furan-1-carboxamide or a pharmaceutically acceptable salt thereof.

45. A compound according to claim 1, wherein the compound is N-(3,5-dichloropyrid-4-yl)-4-methoxy-8-methylamino carboxamido-dibenzo[b,d]furan-1-carboxamide or a pharmaceutically acceptable salt thereof.

46. N-(3,5-dichloropyrid-4-yl)-4-difluoromethoxy-8-methanesulfonamido-dibenzo[b,d]furan-1-carboxamide or a pharmaceutically acceptable salt thereof.

47. N-(3,5-dichloropyrid-4-yl)-4-difluoromethoxy-8-methanesulfonamido-dibenzo[b,d]furan-1-carboxamide sodium salt.

48. A compound according to claim 1, wherein the compound is N-(3,5-dichloropyrid-4-yl)-4-difluoromethoxy-8-ethanesulfonamido-dibenzo[b,d]furan-1-carboxamide or a pharmaceutically acceptable salt thereof.

49. A compound according to claim 1, wherein the compound is N-(3,5-dichloropyrid-4-yl)-4-difluoromethoxy-8-N,N-dimethylaminosulfonamido-dibenzo[b,d]furan-1-carboxamide or a pharmaceutically acceptable salt thereof.

50. A compound according to claim 1, wherein the compound is N-(3,5-dichloropyrid-4-yl)-4-difluoromethoxy-8-acetamido-dibenzo[b,d]furan-1-carboxamide or a pharmaceutically acceptable salt thereof.

51. A compound according to claim 1, wherein the compound is N-(3,5-dichloropyrid-4-yl)-4-difluoromethoxy-8-(1-chloropropylcarboxamido)-dibenzo[b,d]furan-1-carboxamide or a pharmaceutically acceptable salt thereof.

52. A compound according to claim 1, wherein the compound is N-(3,5-dichloropyrid-4-yl)-4-difluoromethoxy-8-cyclopropylcarboxamido-dibenzo[b,d]furan-1-carboxamide or a pharmaceutically acceptable salt thereof.

53. A compound according to claim 1, wherein the compound is N-(3,5-dichloropyrid-4-yl)-4-difluoromethoxy-8-ethoxycarbonylcarboxamido-dibenzo[b,d]furan-1-carboxamide or a pharmaceutically acceptable salt thereof.

54. A compound according to claim 1, wherein the compound is N-(3,5-dichloropyrid-4-yl)-4-difluoromethoxy-8-hydroxycarbonylcarboxamido-dibenzo[b,d]furan-1-carboxamide or a pharmaceutically acceptable salt thereof.

55. A compound according to claim 1, wherein the compound is N-(3,5-dichloropyrid-4-yl)-4-difluoromethoxy-8-hydroxycarbonylcarboxamido-dibenzo[b,d]furan-1-carboxamide di sodium salt.

56. A compound according to claim 1, wherein the compound is N-(3,5-dichloropyrid-4-yl)-4-difluoromethoxy-8-fur-2-ylcarboxamido-dibenzo[b,d]furan-1-carboxamide or a pharmaceutically acceptable salt thereof.

57. A compound according to claim 1, wherein the compound is N1-phenyl-4-methoxy-8-acetamido-dibenzo[b,d]furan-1-carboxamide or a pharmaceutically acceptable salt thereof.

58. A compound according to claim 1, wherein the compound is N1-(4-methoxyphenyl)-4-methoxy-8-acetamido-dibenzo[b,d]furan-1-carboxamide or a pharmaceutically acceptable salt thereof.

59. A compound according to claim 1, wherein the compound is N-(3,5-dichloropyrid-4-yl)-4-methoxy-8-(ethylaminothiocarboxamido)-dibenzo[b,d]furan-1-carboxamide or a pharmaceutically acceptable salt thereof.

60. A compound according to claim 1, wherein the compound is N-(3,5-dichloropyrid-4-yl)-4-methoxy-8-(n-butylaminothiocarboxamido)-dibenzo[b,d]furan-1-carboxamide or a pharmaceutically acceptable salt thereof.

61. A compound according to claim 1, wherein the compound is N1-(pyrid-3-yl)-4-methoxy-8-acetamido-dibenzo[b,d]furan-1-carboxamide or a pharmaceutically acceptable salt thereof.

62. A compound according to claim 1, wherein the compound is N-(3,5-dichloropyrid-4-yl)-4-methoxy-8-acetamido-dibenzo[b,d]furan-1-carboxamide-N-oxide or a pharmaceutically acceptable salt thereof.

63. A compound according to claim 1, wherein the compound is N-(3,5-dichloropyrid-4-yl)-4-methoxy-8- methanesulfonamido-dibenzo[b,d]furan-1-carboxamide-N-oxide or a pharmaceutically acceptable salt thereof.

64. A compound according to claim 1, wherein the compound is N-(pyrid-4-yl)-4-methoxy-8-acetamido-dibenzo[b,d]furan-1-carboxamide or a pharmaceutically acceptable salt thereof.

65. A compound according to claim 1, wherein the compound is N-(3,5-dichloropyrid-4-yl)-4-methoxy-8-(2-ethoxy-2-oxo-ethylaminocarbonylamino)-dibenzo[b,d]furan-1-carboxamide or a pharmaceutically acceptable salt thereof.

66. A compound according to claim 1, wherein the compound is N-(3,5-dichloropyrid-4-yl)-4-methoxy-8-(2-hydroxy-2-oxo-ethylaminocarbonylamino)-dibenzo[b,d]furan-1-carboxamide or a pharmaceutically acceptable salt thereof.

67. A compound according to claim 1, wherein the compound is N-(3,5-dichloropyrid-4-yl)-4-methoxy-8-(2-ethoxy-2-oxo-ethylamino)-dibenzo[b,d]furan-1-carboxamide or a pharmaceutically acceptable salt thereof.

68. A compound according to claim 1, wherein the compound is N-(3,5-dichloropyrid-4-yl)-4-methoxy-8-(2-hydroxy-2-oxo-ethylamino)-dibenzo[b,d]furan-1-carboxamide or a pharmaceutically acceptable salt thereof.

69. A compound according to claim 1, wherein the compound is N-(3,5-dichloropyrid-4-yl)-4-difluoromethoxy-8-methanesulfonamido-dibenzo[b,d]furan-1-carboxamide disodium salt.

70. A compound according to claim 1, wherein the compound is N-(3,5-dichloropyrid-4-yl)-1-methoxy-6-acetamido-dibenzo[b,d]thiophene-4-carboxamide or a pharmaceutically acceptable salt thereof.

71. A N-(3,5-dichloropyrid-4-yl)-4-difluoromethoxy-8-acetamido-dibenzo[b,d]furan-1-carboxamide sodium salt.

72. A N-(3,5-dichloropyrid-4-yl)-4-difluoromethoxy-8-fur-2-ylcarboxamido-dibenzo[b,d]furan-1-carboxamide sodium salt.

73. N-(3,5-dichloropyrid-4-yl)-4-difluoromethoxy-8-methane sulfonamido-dibenzo[d,b]furan-1-carboxamide-N-oxide or a pharmaceutically acceptable salt thereof.

74. N-(3,5-dichloropyrid-4-yl)-4-difluoromethoxy-8-methanesulfonamido-dibenzo[b,d]furan-1-carboxamide monosodium salt.

75. A pharmaceutical composition comprising a compound of claim 1 and a pharmaceutically acceptable carrier or diluent.

76. A pharmaceutical composition comprising a compound of claim 46 and a pharmaceutically acceptable carrier or diluent.

77. A pharmaceutical composition comprising a compound of claim 74 and a pharmaceutically acceptable carrier or diluent.

* * * * *